United States Patent
Stream et al.

(10) Patent No.: US 8,002,837 B2
(45) Date of Patent: Aug. 23, 2011

(54) SPINAL STABILIZATION DEVICE AND METHODS

(75) Inventors: Katie Stream, Ishpeming, MI (US); Adam Paltzer, Neguanee, MI (US); Weston Pernsteiner, Marquette, MI (US); Brian P. Janowski, Marquette, MI (US); Douglas B. Moreland, Buffalo, NY (US); Domagoj Coric, Charlotte, NC (US)

(73) Assignee: Pioneer Surgical Technology, Marquette, MI (US)

( * ) Notice: Subject to any disclaimer, the term of this patent is extended or adjusted under 35 U.S.C. 154(b) by 913 days.

(21) Appl. No.: 11/750,612

(22) Filed: May 18, 2007

(65) Prior Publication Data
US 2007/0282441 A1 Dec. 6, 2007

Related U.S. Application Data

(60) Provisional application No. 60/802,038, filed on May 19, 2006.

(51) Int. Cl.
*A61F 2/44* (2006.01)
(52) U.S. Cl. .................... 623/17.16; 623/17.11
(58) Field of Classification Search .... 623/17.11–17.16; 606/249
See application file for complete search history.

(56) References Cited

U.S. PATENT DOCUMENTS

| | | | |
|---|---|---|---|
| 4,349,921 A | 9/1982 | Kuntz | |
| 4,834,757 A | 5/1989 | Brantigan | |
| 4,865,603 A * | 9/1989 | Noiles | 623/23.5 |
| 5,425,772 A | 6/1995 | Brantigan | |
| 5,443,514 A | 8/1995 | Steffee | |
| 5,609,635 A | 3/1997 | Michelson | |
| 5,645,598 A | 7/1997 | Brosnahan, III | |
| 5,653,762 A | 8/1997 | Pisharodi | |
| 5,716,415 A | 2/1998 | Steffee | |
| 5,860,973 A | 1/1999 | Michelson | |
| 5,888,224 A | 3/1999 | Beckers et al. | |
| 5,984,967 A * | 11/1999 | Zdeblick et al. | 623/17.16 |
| 6,080,158 A | 6/2000 | Lin | |
| 6,143,033 A * | 11/2000 | Paul et al. | 623/17.11 |
| 6,290,724 B1 | 9/2001 | Marino | |
| 6,537,320 B1 | 3/2003 | Michelson | |
| 6,579,318 B2 | 6/2003 | Varga et al. | |
| 6,610,089 B1 | 8/2003 | Liu et al. | |
| 6,719,794 B2 | 4/2004 | Gerber et al. | |
| 6,942,698 B1 | 9/2005 | Jackson | |
| 2002/0065560 A1 | 5/2002 | Varga et al. | |
| 2002/0143400 A1* | 10/2002 | Biscup | 623/17.11 |
| 2003/0023306 A1 | 1/2003 | Liu et al. | |
| 2003/0073998 A1* | 4/2003 | Pagliuca et al. | 606/61 |

(Continued)

FOREIGN PATENT DOCUMENTS

CA 1146301 5/1983
(Continued)

*Primary Examiner* — Thomas C Barrett
*Assistant Examiner* — Christian Sevilla
(74) *Attorney, Agent, or Firm* — Fitch, Even, Tabin & Flannery

(57) ABSTRACT

Implant devices in the form of a vertebral body replacement for implantation within an intervertebral space between adjacent vertebrae is disclosed for immobilization and support of the adjacent vertebrae in a desired spatial relationship and for promotion of fusion by the adjacent vertebrae. Instruments for insertion and implantation of the implant devices and of fusion material such as bone graft material are disclosed. Methods are disclosed for implantation of the implant devices.

9 Claims, 51 Drawing Sheets

U.S. PATENT DOCUMENTS

| | | |
|---|---|---|
| 2003/0135275 A1 | 7/2003 | Garcia et al. |
| 2003/0149483 A1 | 8/2003 | Michelson |
| 2004/0127990 A1 | 7/2004 | Bartish |
| 2004/0167538 A1 | 8/2004 | Gerber et al. |
| 2004/0199251 A1 | 10/2004 | McCombe et al. |
| 2004/0243239 A1 | 12/2004 | Taylor |
| 2005/0010292 A1 | 1/2005 | Carrasco |
| 2005/0021030 A1 | 1/2005 | Pagliuca et al. |
| 2005/0027360 A1 | 2/2005 | Webb et al. |
| 2005/0096745 A1 | 5/2005 | Andre |
| 2005/0125062 A1 | 6/2005 | Biedermann et al. |
| 2006/0195190 A1 | 8/2006 | Lechmann |

FOREIGN PATENT DOCUMENTS

| | | |
|---|---|---|
| EP | 0042271 | 9/1984 |
| EP | 0834295 | 9/1997 |
| EP | 1346695 | 12/2005 |
| FR | 2703580 | 10/1994 |
| FR | 2754170 | 4/1998 |
| WO | 9000037 | 1/1990 |
| WO | 9428824 | 12/1994 |
| WO | 2004000177 | 12/2003 |

* cited by examiner

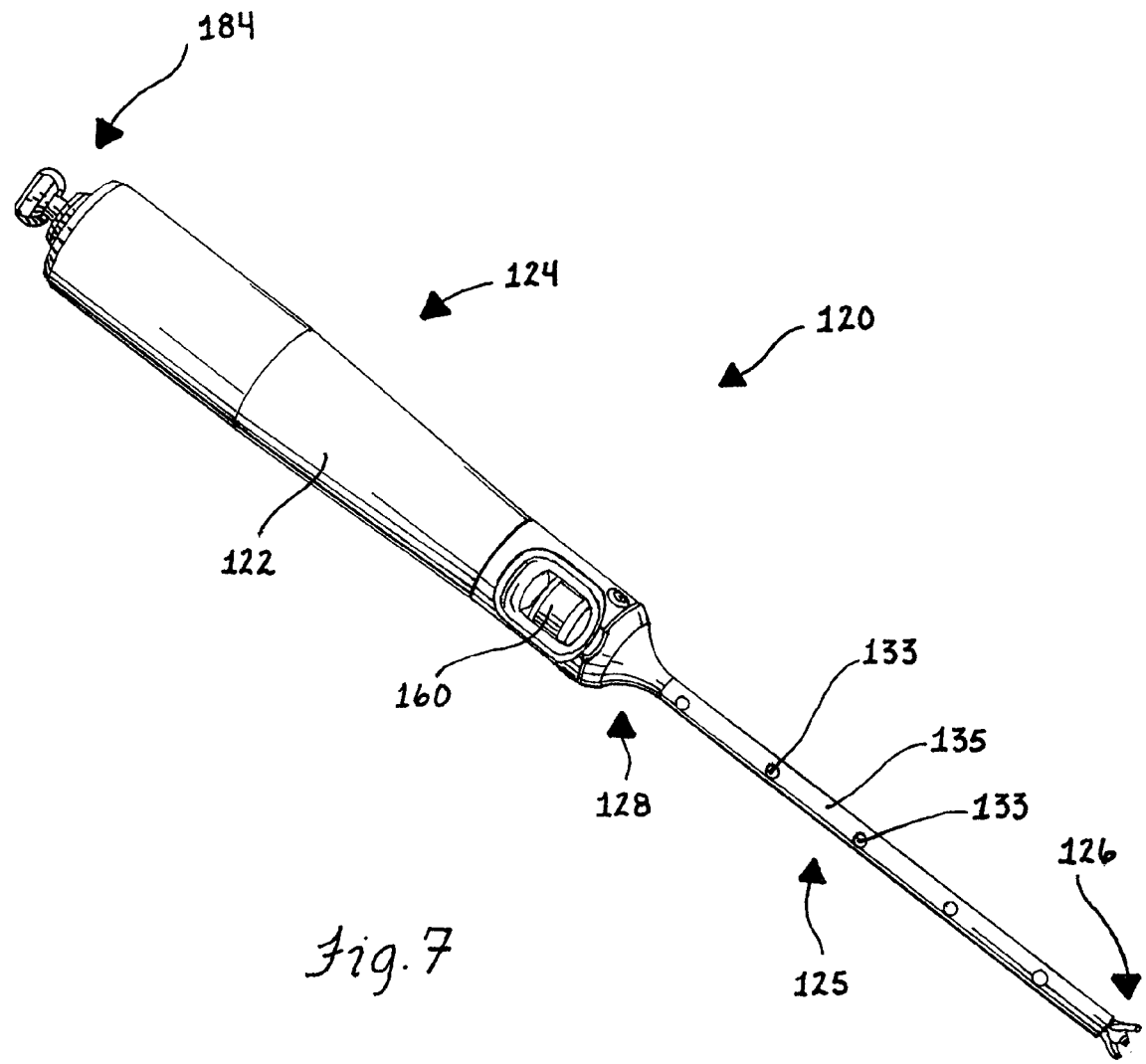

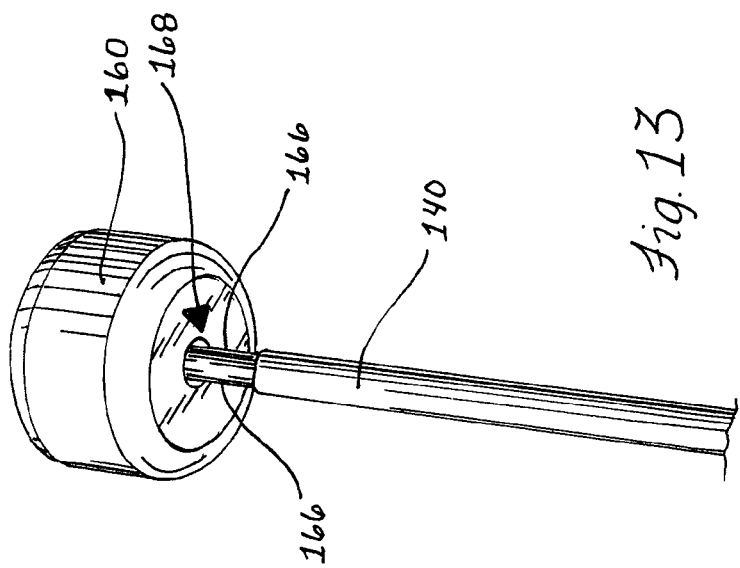
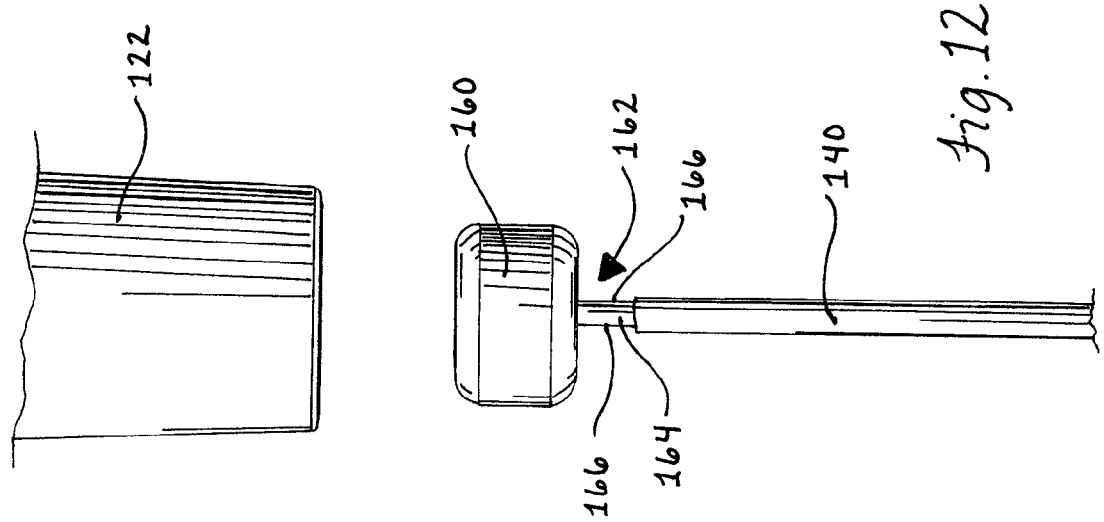

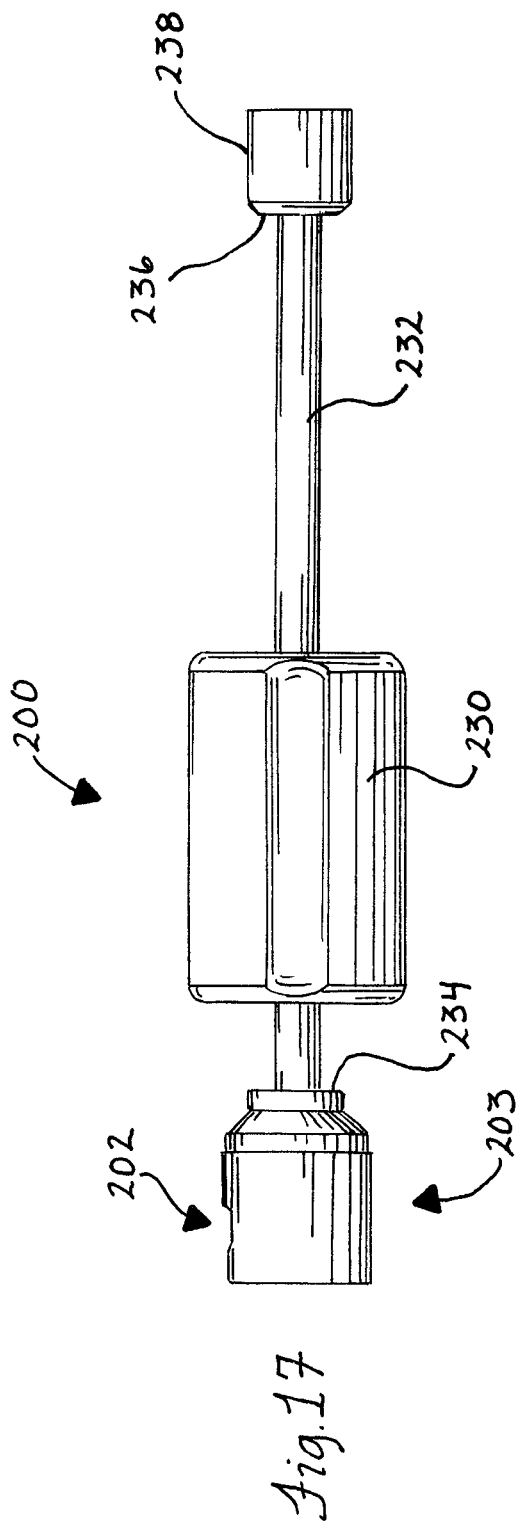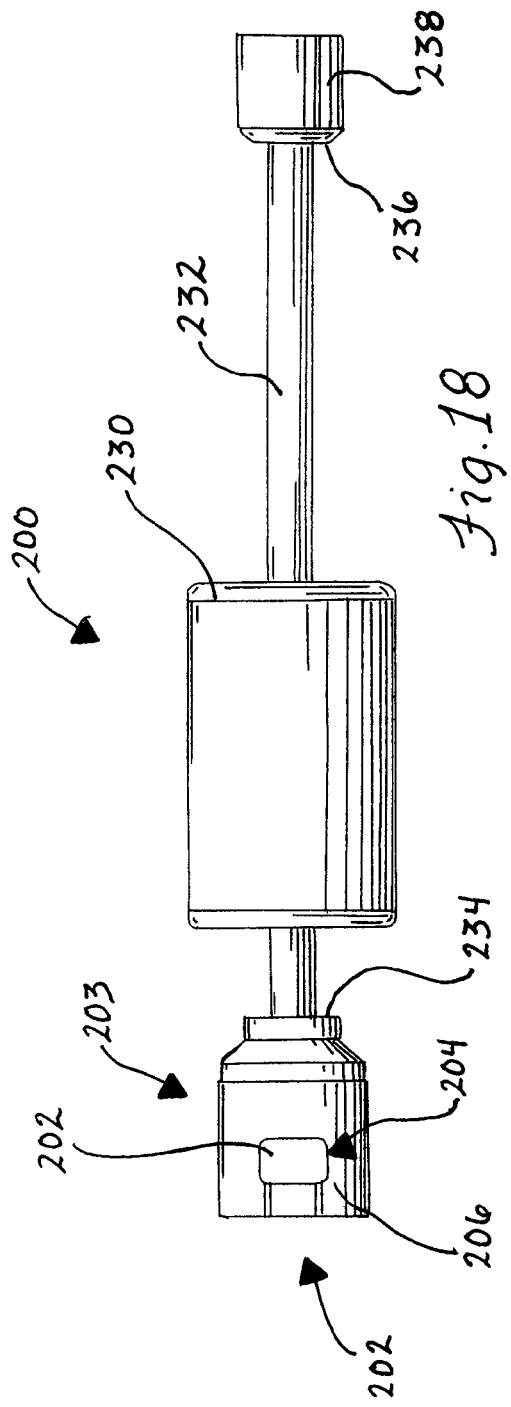

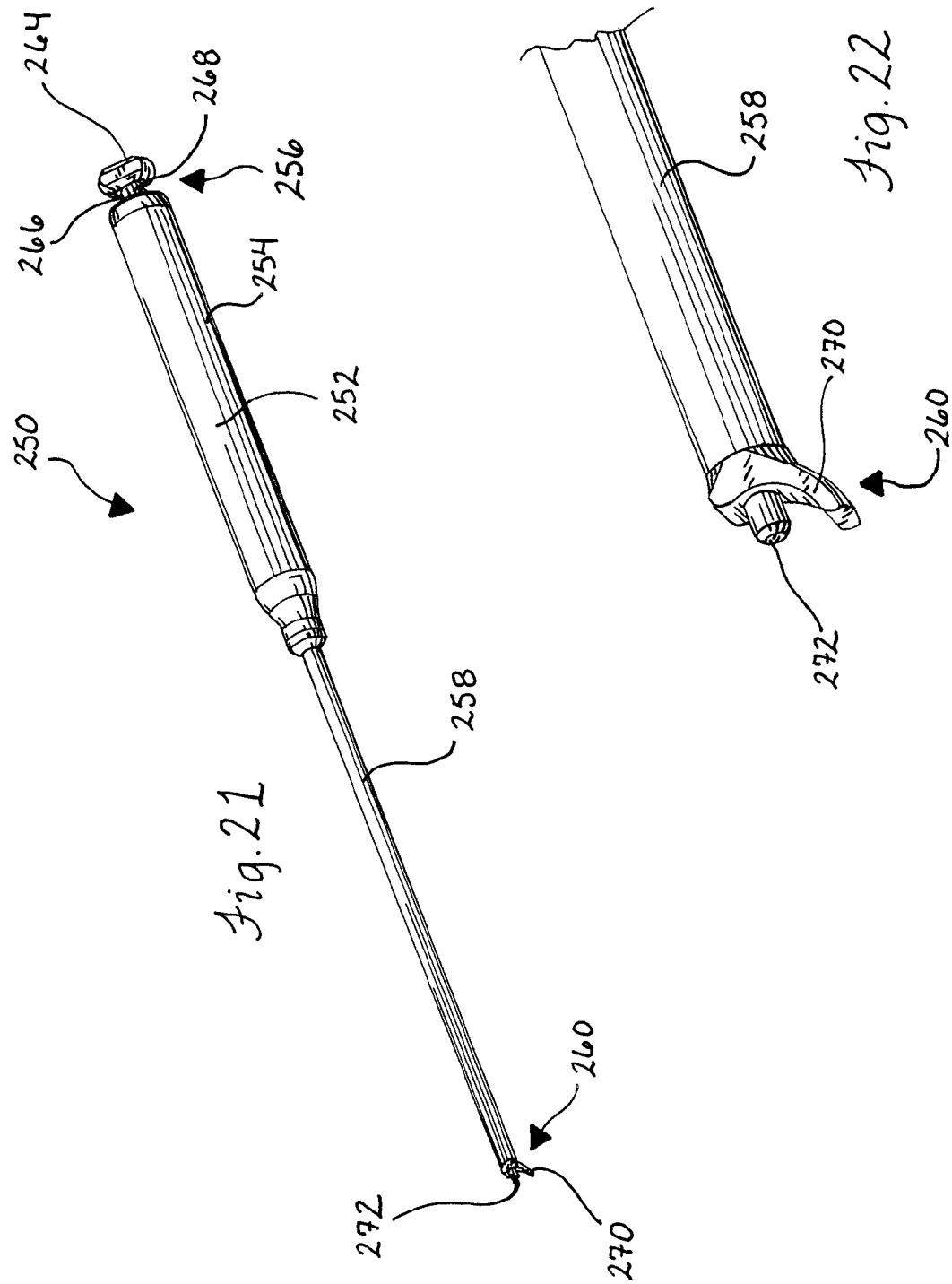

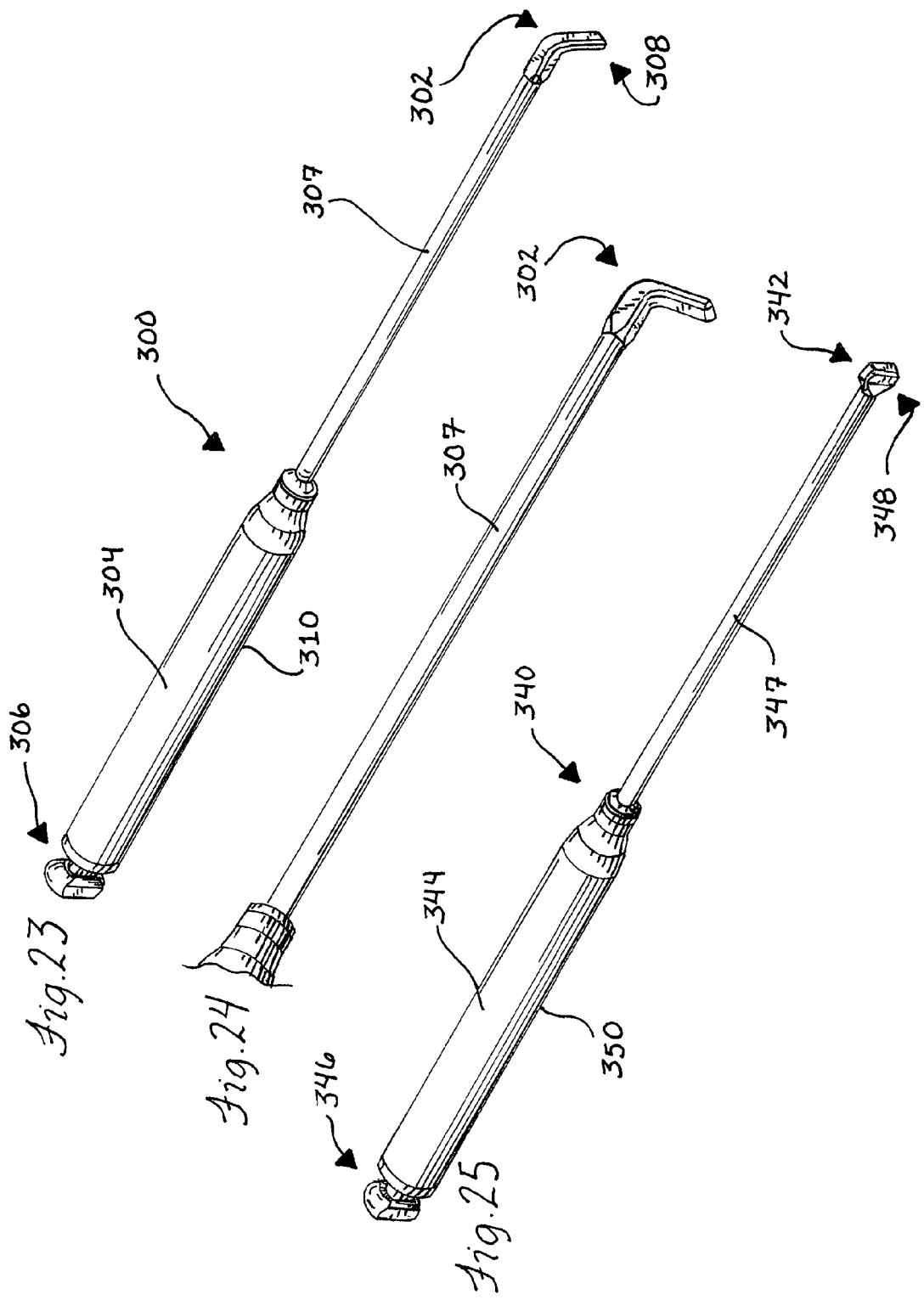

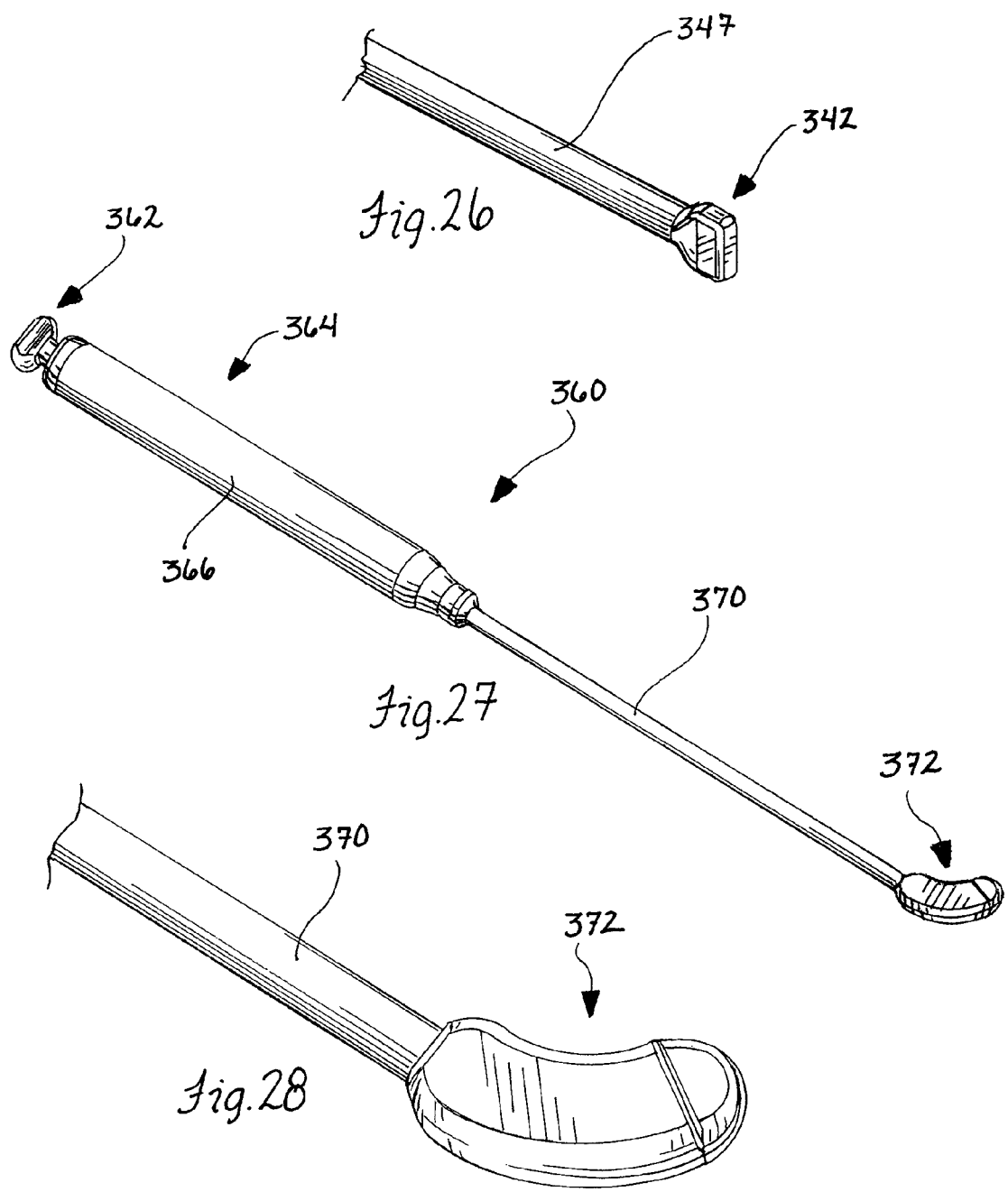

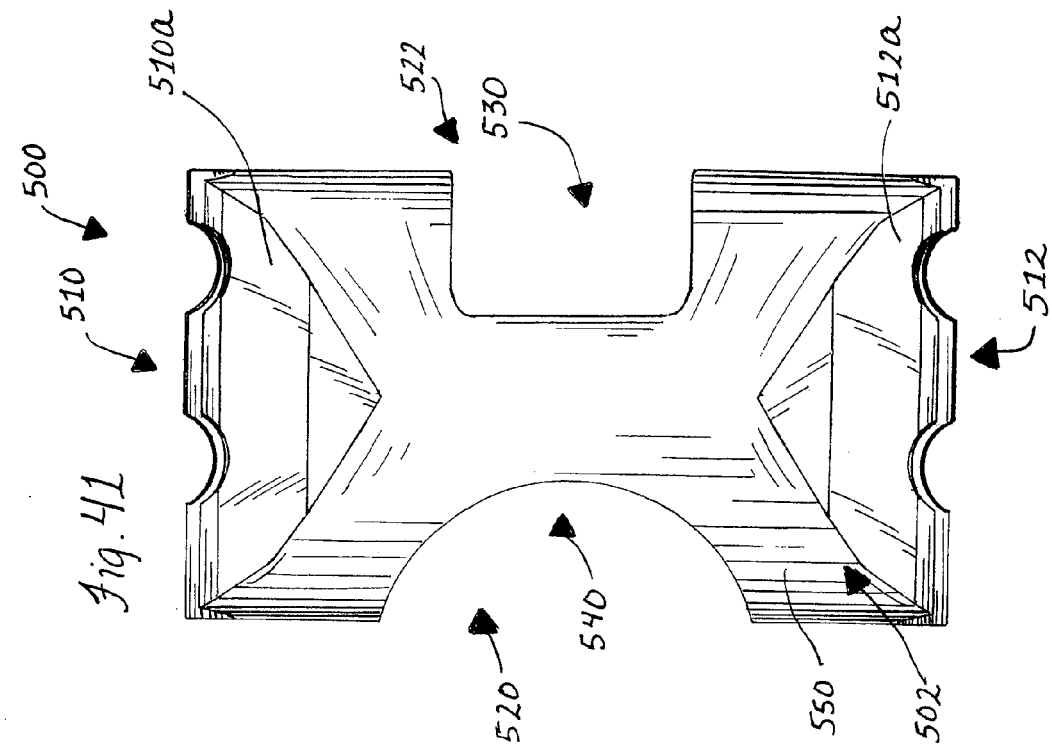
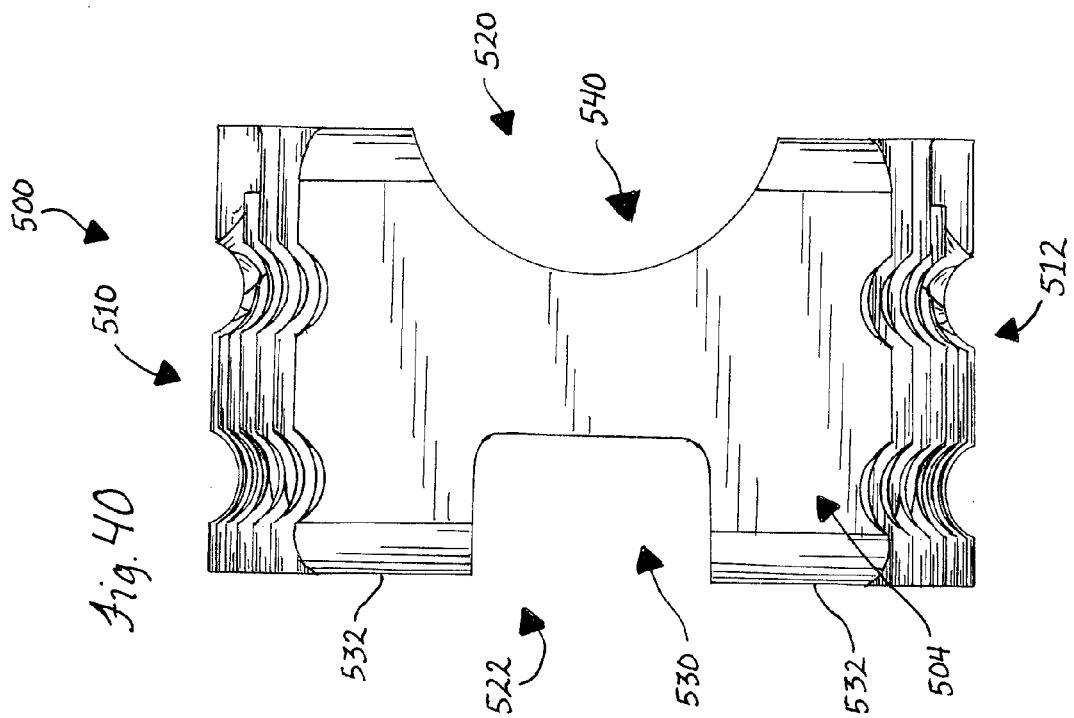

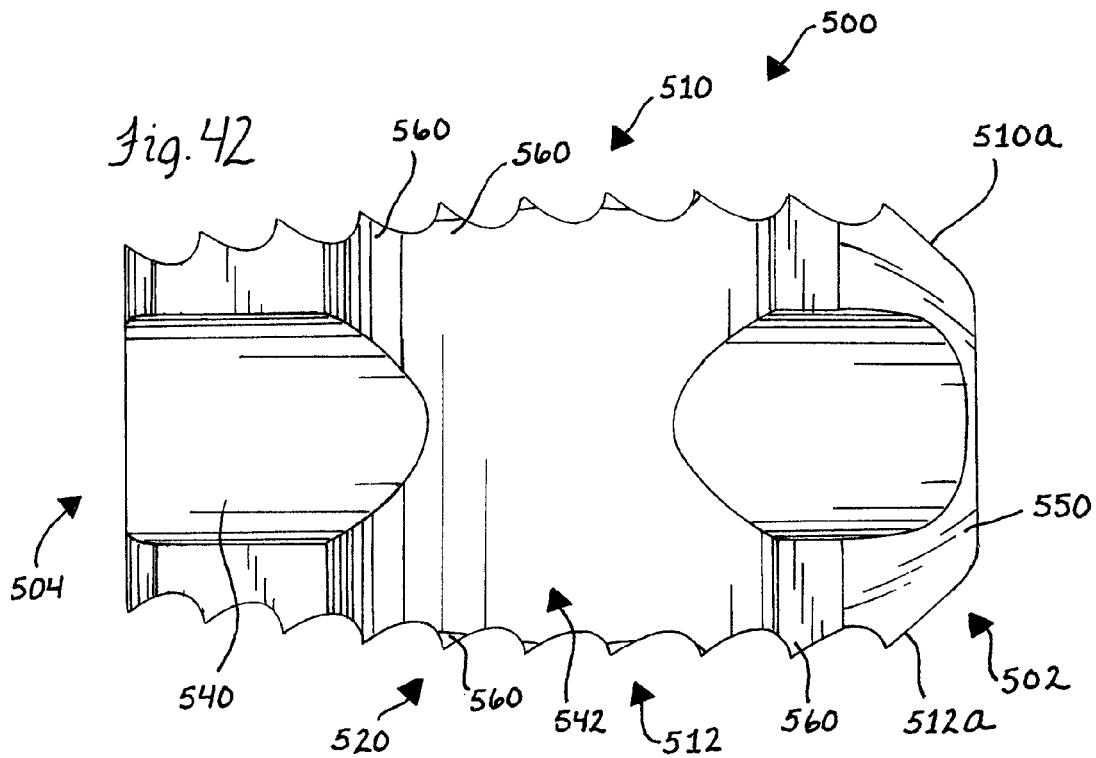
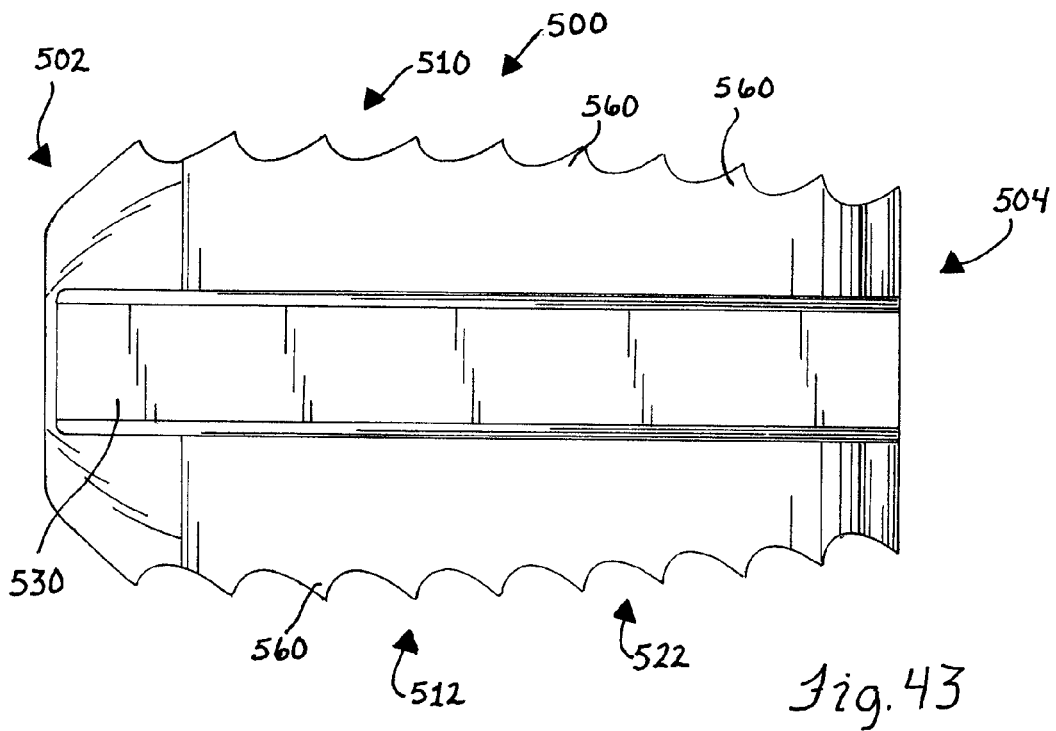

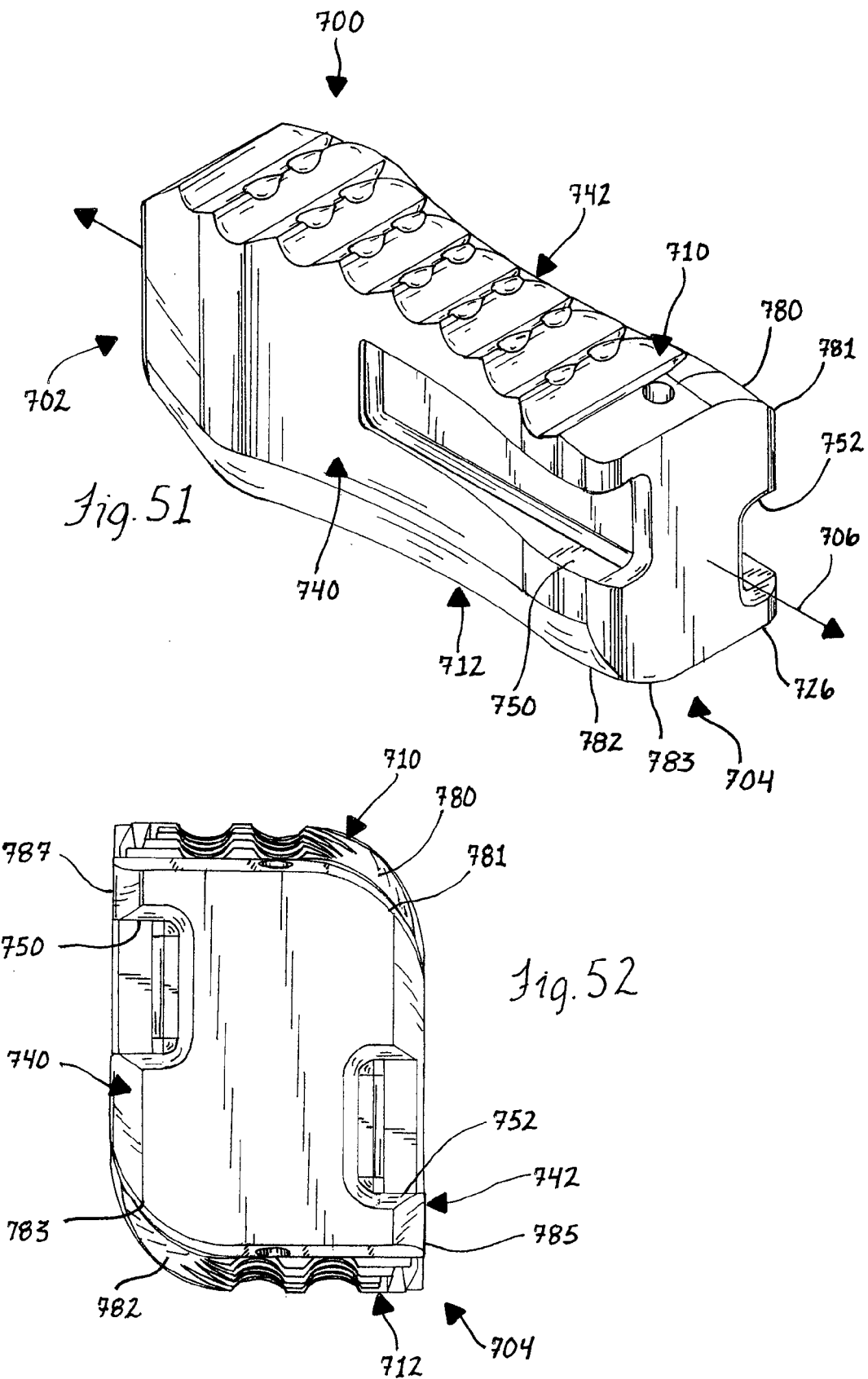

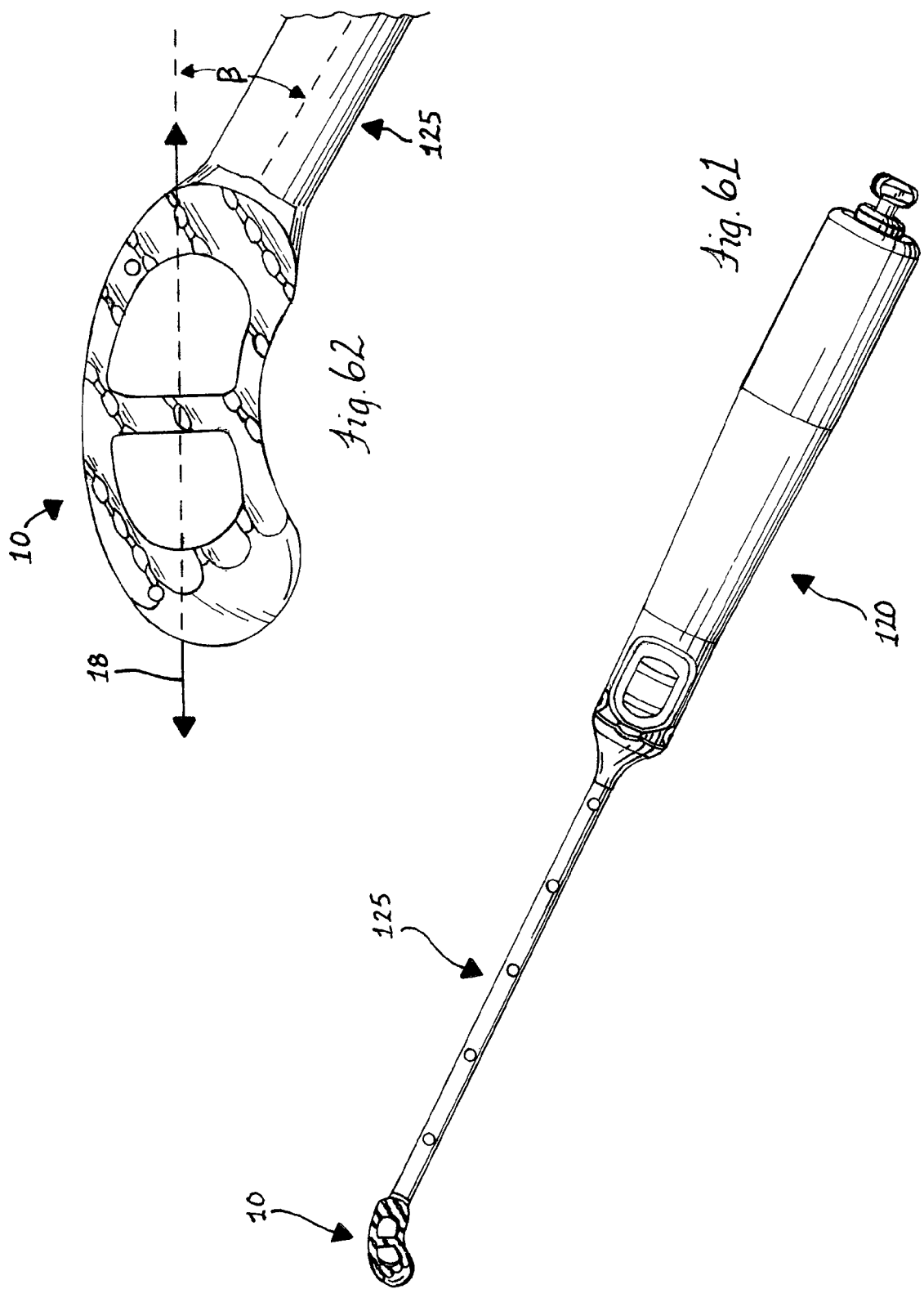

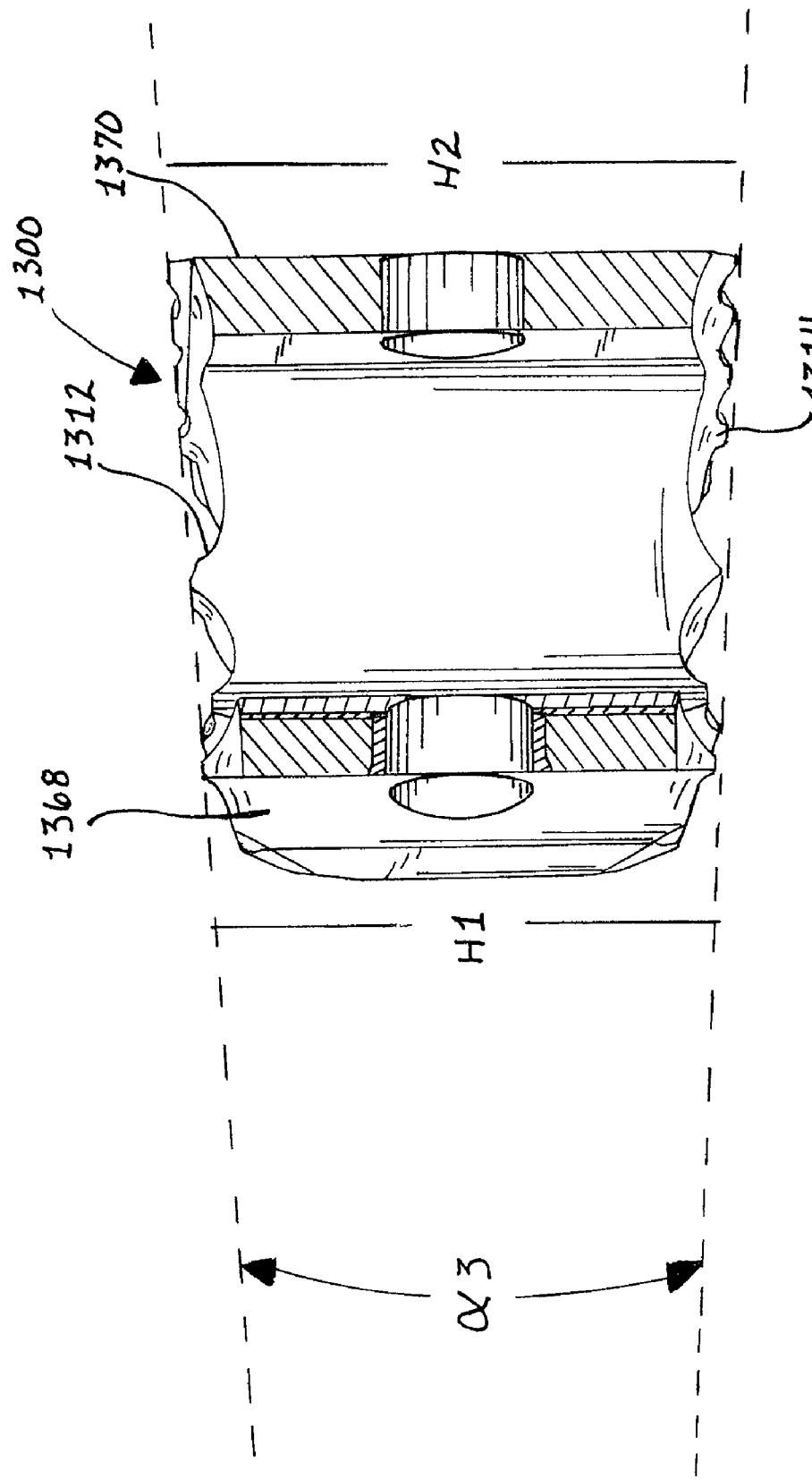

SPINAL STABILIZATION DEVICE AND METHODS

CROSS REFERENCE TO RELATED APPLICATIONS

This application claims the benefit of the filing date of U.S. Provisional Application 60/802,038 which is hereby incorporated in its entirety herein.

FIELD OF THE INVENTION

The invention relates to spinal stabilization devices and methods and, in particular, to devices for implantation in an intervertebral disc space for immobilization and fusion of adjacent vertebrae, to methods for the implantation of such devices, and to instruments for performing the implantation.

BACKGROUND OF THE INVENTION

A variety of spinal conditions result in a person experiencing pain or limited physical activity and ability. More specifically, damage to vertebrae composing the spine and spinal discs between the vertebrae may occur as a result of trauma, deformity, disease, or other degenerative conditions. Some of these conditions can be life-threatening, while others cause impingement on the spinal cord resulting in pain and a lack of mobility. Removing the impingement, thus reducing swelling or pressure from the damaged or diseased tissue against the spinal cord, can relieve the pain and often promotes healing and return of normal nervous system functioning. However, the absence of proper medical care may lead to further damage and degeneration of spinal health and to permanent spinal cord damage.

The spine principally includes a series of vertebrae and spinal discs located in a space between adjacent vertebrae. The vertebrae are formed of hard bone while the discs comprise a comparatively soft annulus and nucleus. The discs support the vertebrae in proper position and enable the torso to be rotated and to bend laterally and anteriorly-posteriorly. The discs also act as shock absorbers or cushions when the spine is experiencing shock, such as when a person jogs.

Damage to the spine often results in a reduced physiological capability. For instance, damage to the disc may allow the annulus to bulge, commonly referred to as a herniated disc. In more severe cases, the damage may allow the nucleus to leak from the annulus. These same results may be brought about by a damaged or fractured vertebra. In any event, such damage often causes the vertebrae to shift closer or compress, and often causes a portion of the disc to press against the spinal cord.

One manner of treating these conditions is through immobilization of the vertebrae in a portion of the spine, such as two or more adjacent vertebrae. The conditions often lead to degeneration and a loss of disc support, and immobilization is often beneficial in reducing or eliminating pain. Immobilization and/or fusion have been performed via a number of techniques and devices, and the type of injury often suggests a preferred treatment regime.

One of these treatments is known as spinal fusion surgery. For this, two or more adjacent or consecutive vertebrae are initially immobilized relative to each other and, over time, become fused in a desired spatial relationship. The vertebrae are relatively immobilized at the proper intervertebral distance which replicates the support characteristics of the spine. This prescription sacrifices the rotation or flexion between the affected vertebrae, such that some loss of movement and flexibility is experienced. However, the compression on the spinal cord due to the injury or damage is reduced or eliminated, and the fused vertebrae protect the spine and spinal cord from injury. Overall, the non-fused portions of the spine are largely able to compensate for most normal movement expected by a patient.

Currently, a number of vertebral body replacement devices (VBRs) for immobilizing and fusing adjacent vertebrae are known. During an implantation procedure, the intervertebral space is initially excavated to provide a volume for locating a VBR therein. Once excavated, the adjacent vertebrae have a tendency to shift toward each other a small amount, thereby compressing the space or volume. Additionally, many VBRs have surface features such as prongs or teeth which extend away from upper and lower surfaces of the VBR for being embedded into the adjacent vertebrae. In order to locate the device within the intervertebral space, instruments may be used to spread the vertebrae apart. During such a procedure, care must be taken not to damage the spinal cord. The VBRs may then be inserted into the intervertebral space in an orientation where the surfaces with teeth thereon face the adjacent vertebral surfaces. However, if the vertebrae are not sufficiently distracted, VBR insertion can be difficult due to resistance generated when the teeth engage the vertebrae, particularly if the implant needs to be redirected or turned in the intervertebral space to an implantation orientation that is offset from the insertion orientation thereof.

Accordingly, it has been disclosed that the VBR may be inserted initially into the intervertebral space in a first orientation where the upper and lower surfaces and the teeth thereon face laterally outward and then be rotated secondarily so that the teeth are brought into engagement with and embed into endplates of the vertebrae. This allows distraction of the adjacent vertebrae to be kept to a minimum. Stability of the spine benefits from the VBR having a contour or shape that generally follows the surface shape of the endplates. As the endplates are generally slightly concave, the surface portions of the VBR including the gripping teeth often have a corresponding contour. In this configuration, the spacing between the side surfaces of the VBR will generally be less than between the toothed surfaces for maintaining the vertical distraction required prior to VBR insertion.

Accordingly, rotation of the VBR in the intervertebral space may result in significant stress upon the VBR since the rotation may require forcing the vertebrae apart a small amount. Because the VBR typically has a body of relatively small size for fitting in the intervertebral space and particularly if cavities are formed therein for graft material, VBR rotation can generate undesirably high compressive force on the VBR.

A number of solutions have been attempted for addressing these compressive forces due to the rotation. The trend in the field is that device manufactures are reducing the size of VBRs to such a degree so that rotation thereof requires less separation of the vertebrae. However, this solution comes at the expense of having the VBR securely positioned in the intervertebral space with the teeth securely gripping the adjacent vertebral surfaces. Another trend is to form the VBRs with a strong material, such as PEEK, and avoid the use of natural bone or artificial bone materials such as hydroxyapatite or allograft.

Unfortunately, these stronger materials are not bio-resorbable. The purpose of the fusion procedure is to develop a lattice, matrix, or solid mass of bone joined with and extending between the adjacent vertebrae and through the intervertebral space. Eventually, the formed or developed bone and the vertebrae are joined to provide a somewhat unitary, incompressible structure that maintains the proper pre-fusion spatial relationship for the size to reduce or eliminate the impingement on the spinal cord. The VBR formed of these stronger materials is unable to transubstantiate into bone, join with bone, or be absorbed by the body for replacement by bone growth. This results in a boundary interface between the implant device and any resultant bone growth. Again, this is often addressed by reducing the size of the VBR so that more graft material may often be packed into the intervertebral space around the VBR. However, as mentioned, this is done at the cost of having secure implantation of the VBR.

As noted, the intervertebral space receives the VBR or implant device as well as an amount of graft material. The graft material may be in a number of forms, such as cancellous bone chips, which are packed into the intervertebral space and around the VBR. For VBRs with internal cavities opening on at least one side to the intervertebral space, graft material is also placed within the cavities so that bone may grow through the VBR device and join with bone formation throughout the intervertebral space.

However, as these bone chips are loose and oftentimes fragile, migration of the bone chips from the intervertebral space presents an issue. While implanting more bone graft material promotes faster bone formation throughout the intervertebral space, the loose bone chips or graft material portions tend to separate from each other, a tendency which is exacerbated by being more tightly packed. Full fusion may take upwards of two years, during which time a patient's movement may contribute to the graft material explanting from the intervertebral site. In general, previous solutions to this problem have consisted of sewing the intervertebral site closed, such as by retaining and re-closing the natural damaged annulus, or by providing the cavities within a VBR.

Another issue confronted with the implantation of the VBR is in situ adjustments or positioning. Once rotated, the teeth are engaged with the endplates thereby making adjustment difficult. If extensive adjustments are made in situ, the teeth may erode or carve out additional space which reduces the distance between the vertebrae. If a minimal proper distance is not maintained, the spinal cord may still be impinged. Often such impingement is difficult to recognize until after the fusion has progressed to a point where revision surgery is difficult and complicated.

Accordingly, there has been a need for improved spinal fusion systems and for improved methods for performing spinal fusion surgery.

SUMMARY OF THE INVENTION

Thus, in accordance with one aspect of the invention, an implant device is provided for implantation within an intervertebral space between adjacent vertebrae. The implant device comprises an implant body having an insertion end, a trailing end, and a longitudinal axis extending generally between the insertion end and the trailing end, an upper surface and a lower surface of the body, a plurality of vertebral gripping members formed on at least a portion of both the upper and lower surfaces for engaging the adjacent vertebrae, and one or more rows of gripping members, with each row having the gripping members spaced from each other in the row, the rows having a predetermined orientation relative to the longitudinal axis to extend transverse thereto so that the rows of gripping members guide the implant body during insertion from an insertion orientation with the longitudinal axis extending in a generally anterior-posterior direction to be turned toward an implantation orientation in the intervertebral space via the gripping members engaging the adjacent vertebrae and the predetermined orientation of the rows thereof causing the implant body to be frictionally biased toward the implantation orientation from the insertion orientation.

According to another aspect of the invention, an implant device is provided for implantation within an intervertebral space between adjacent vertebrae, which comprises an implant body having opposite end portions and a longitudinal axis extending between the end portions, opposite side slots in the body for turning the body in a predetermined rotary direction about the longitudinal axis to implant the body between the vertebrae, upper and lower surfaces including gripping structure for securing the implant body between adjacent vertebrae upon turning of the implant body in the predetermined rotary direction in the intervertebral space, and diagonally-opposed corner portions, the corner portions having an arcuate configuration and being arranged on the implant body so that with the implant body inserted between the adjacent vertebrae, turning the implant body in the predetermined rotary direction shifts the arcuate corner portions generally laterally inward in the intervertebral space with the arcuate configuration of the corner portions minimizing damage to the adjacent vertebrae during the turning of the implant body.

According to yet another aspect of the invention, an implant device is provided for implantation within an intervertebral space between adjacent vertebrae, which comprises an implant body having insertion and trailing end portions, an intermediate concave surface portion of the implant body, a first recessed engagement portion at the trailing end portion, and a second recessed engagement portion at the insertion end portion, the first and second recessed engagement portions oriented to receive a portion of an insertion tool therein and the concave surface portion and the first and second recessed portions cooperating to provide a large size space for receipt of graft material.

BRIEF DESCRIPTION OF THE DRAWINGS

FIG. 7 is a perspective view of an insertion tool for implanting the VBR device of FIG. 1 showing a handle for manipulating the insertion tool, a sheath secured with the handle, and an engagement end formed on a distal end of the handle for coupling the insertion tool with the tool-engagement end of the VBR device;

FIG. 12 is a side elevation view of the insertion tool as shown in FIG. 10 with a portion of the handle removed to show a proximal end of the rod having side flats for being received with a knob to prevent relative rotation therebetween;

FIG. 13 is a perspective view of the proximal end of the rod received within a throughbore of the knob;

FIGS. 17 and 18 are side elevation views rotated ninety-degrees relative to each other showing the hammer member positioned between a shoulder formed proximate a connection end for securing the hammer instrument with the insertion tool of FIG. 15, and a shoulder on a proximal end opposite the connection end, the hammer member impacting the respective shoulders for providing forces in opposite directions, the forces transmitted through the insertion tool;

FIG. 21 is a perspective view of a tamp device for adjusting the position of the VBR device in the intervertebral space, the tamp device having a tamp end and a connection end for securing with the hammer instrument of FIG. 16, the connection end including a connector having a head and a shank similar to the insertion tool head and shank as shown in FIG. 15;

FIG. 22 is an enlarged perspective view of the tamp end of the tamp device of FIG. 21 showing a C-shaped arm portion and a pin portion respectively receivable in the socket and the threaded bore of the VBR device of FIG. 1;

FIG. 23 is a perspective view of a tamp device having a tamp end for packing graft material into an intervertebral space having a VBR device located therein, and having a connection end for securing with the hammer instrument of FIG. 16, the connection end including a connector having a head and a shank similar to the insertion tool head and shank of FIG. 15;

FIG. 24 is an enlarged perspective view of the tamp end of the tamp device of FIG. 23 showing a L-shaped portion for pressing bone graft material into an intervertebral space and around a VBR device located therein;

FIG. 25 is a perspective view of an alternative tamp device having a tamp end for packing graft material into an intervertebral space having a VBR device located therein, and having a connection end for securing with the hammer instrument of FIG. 16, the connection end including a connector having a head and a shank similar to the insertion tool head and shank of FIG. 15;

FIG. 26 is an enlarged perspective view of the tamp end of the tamp device of FIG. 25 showing a widened blade portion for pressing bone graft material into an intervertebral space and around a VBR device located therein;

FIG. 27 is a perspective view of a trial device for identifying a desired VBR device having a spacer end and a connection end for securing with the hammer instrument of FIG. 16, the connection end including a connector having a head and a shank similar to the insertion tool head and shank of FIG. 15;

FIG. 28 is an enlarged perspective view of the spacer end of the trial device of FIG. 27, the spacer end including a spacer portion sized and shaped to correspond to a size and shape of the VBR device of FIG. 1 without the VBR teeth;

FIG. 40 is an end elevation view of the trailing end of the VBR device of FIG. 36 showing one of the channels having a generally rectangular shape, and one of the channels having a generally curved shape;

FIG. 41 is an end elevation view of the insertion end of the VBR device of FIG. 36 showing the channels;

FIGS. 42 and 43 are side elevation views of the VBR device of FIG. 36 showing gripping members formed on upper and lower surfaces of a body, the upper and lower surfaces having an arcuate outwardly bowed configuration to follow the contour of the vertebral endplates;

FIG. 51 is a perspective view of an alternative configuration of the VBR device of FIG. 44 with offset channels formed on the lateral side surfaces and extending to the trailing end for engaging an insertion tool and for receiving bone graft therein;

FIG. 52 an end elevation view of the trailing end of the VBR device of FIG. 51 showing the offset channels;

FIG. 61 is a perspective view of the insertion tool of FIG. 7 engaging the VBR device of FIG. 1;

FIG. 62 is an enlarged perspective view of the insertion tool of FIG. 7 engaging the VBR device of FIG. 1;

FIG. 76 is a cross-section view of the VBR device of FIG. 74 taken along the line 76-76 of FIG. 74.

DETAILED DESCRIPTION OF THE PREFERRED EMBODIMENTS

Figure 1:
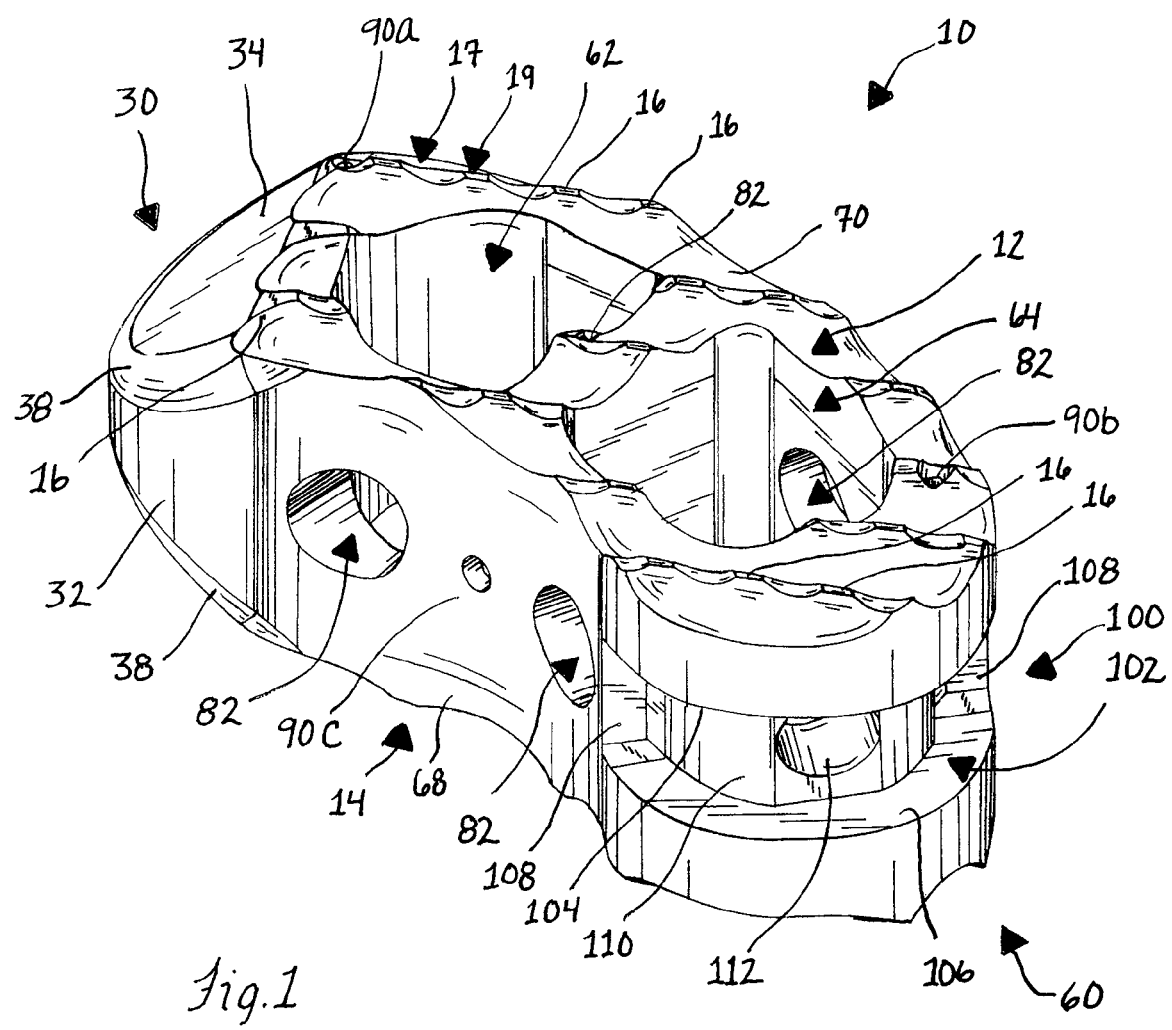
FIG. 1 is a perspective view of a vertebral body replacement (VBR) device of the present invention showing an implant body configured for promoting insertion of the VBR within an intervertebral space, and a socket formed in the body for cooperating with an insertion tool.
Figure 2:
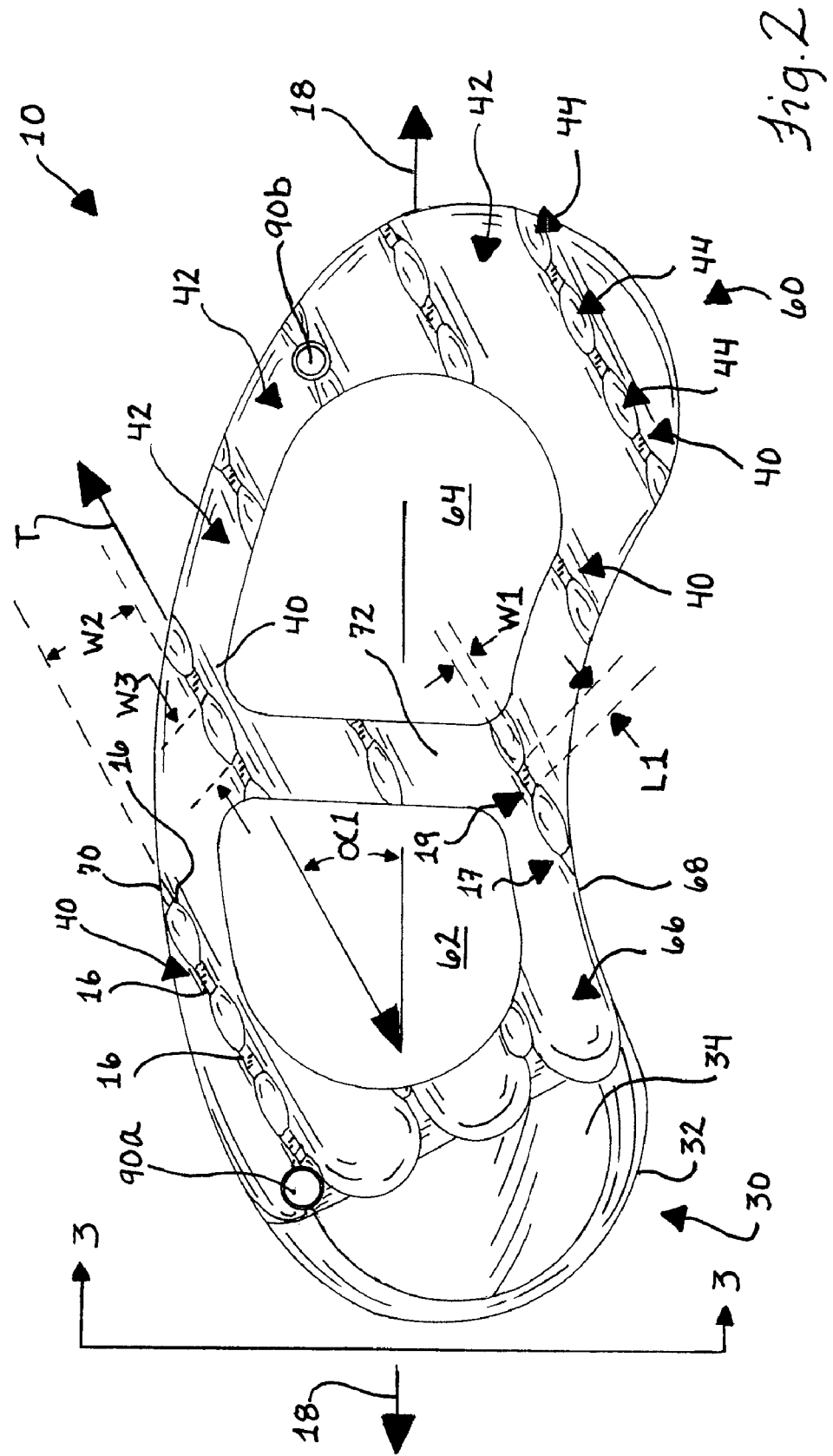
FIG. 2 is a plan view of the VBR device of FIG. 1 showing a curved shape of the implant body, gripping members aligned in rows at a predetermined angle relative to the longitudinal axis of the implant body, walls defining cavities for receiving bone graft material, and vertical radiographic markers for identifying the position and location of the VBR.
Figure 58:
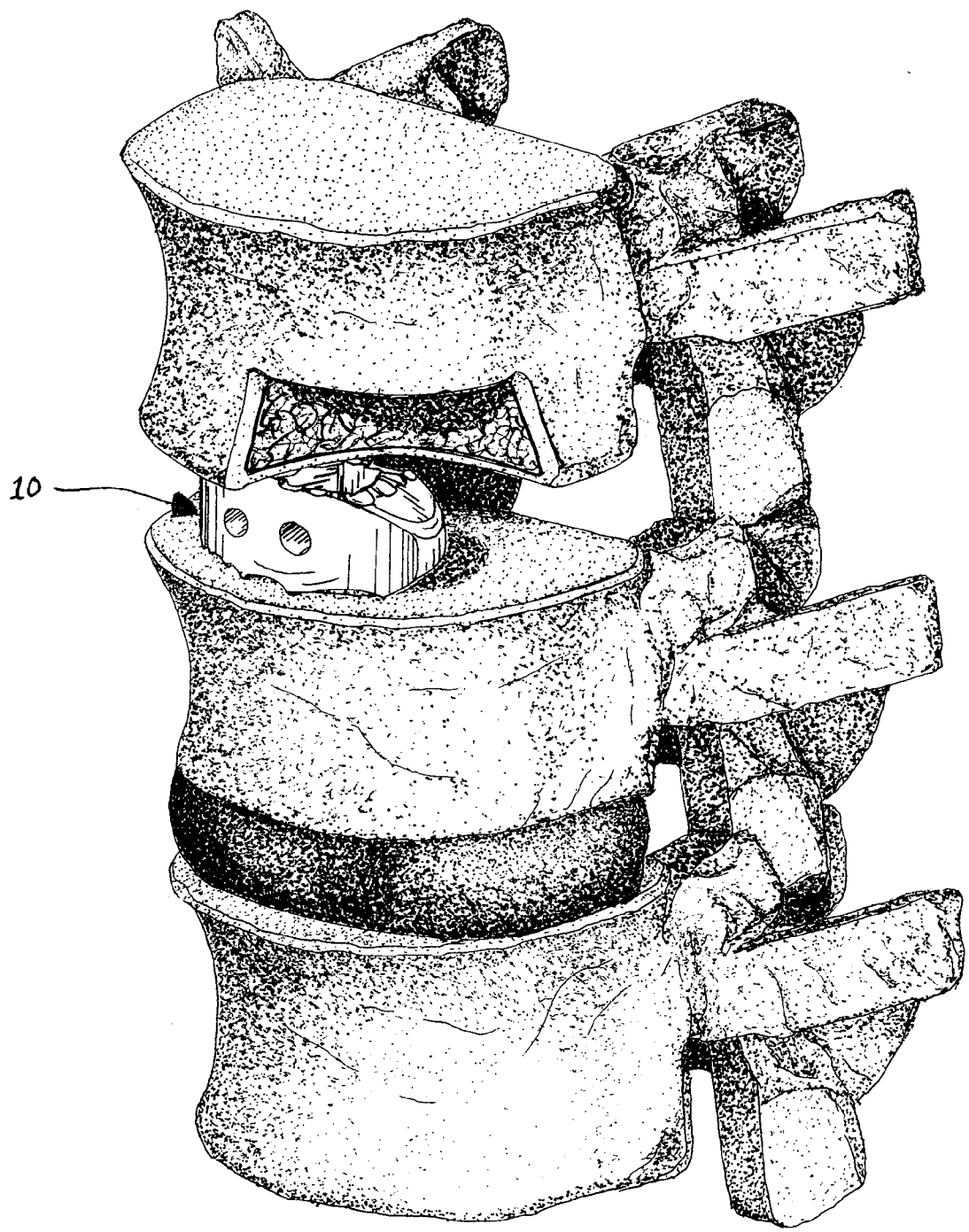
FIG. 58 is a representational view showing the VBR device of FIG. 1 inserted between adjacent vertebrae with a portion of the vertebrae cut-away for visibility.

Referring initially to FIG. 1, an implant device in the form of a vertebral body replacement device (VBR) 10 for spinal fusion surgery is illustrated for implantation within an intervertebral space between adjacent vertebrae. The VBR 10 enables the fusion surgery to be completed with a single VBR 10. As best seen in FIG. 2, the VBR 10 has a generally concavo-convex configuration along a longitudinal axis 18 of the VBR. As illustrated in FIG. 58, once implanted, the longitudinal axis 18 of the VBR extends generally laterally, that is, perpendicular to the anterior-posterior axis of the spine. Accordingly, the VBR 10 is curved so as to have a shape similar to that of a natural spinal disc. Thus, the VBR 10 is able to provide support to the spinal column across a large area.

The VBR 10 includes a number of features for promoting insertion within the intervertebral space, one of which is the shape of an insertion end 30 formed on an end of a body portion 26. During implantation, it is desired to minimize the risks associated with distracting the adjacent vertebrae. The insertion end 30 is shaped to assist in distracting the vertebrae during the insertion of the VBR 10. The insertion end 30 includes a rounded or curved surface 32. The curved surface 32 has a radius of curvature which is generally parallel to the superior-inferior axis of the spine. The insertion end 30 further includes an upper slanted surface 34 slanted downward from an upper gripping surface 12 formed on the body portion 26, and a lower slanted surface 36 slanted upward from a lower gripping surface 14 formed on the body portion 26. The upper and lower slanted surfaces 34, 36 intersect with the curved surface 32 at an intersection 38 which may be beveled or rounded.

The upper and lower slanted surfaces 34, 36 provide a wedge-like shape to the insertion end 30. When force is applied to a trailing end 60, as discussed below, the combination of the slanted surfaces 34, 36 and the curved surface 32 sufficiently distracts the adjacent vertebrae so that the VBR 10 may be inserted therebetween.

The upper and lower gripping surfaces 12, 14 promote a general direction for insertion of the VBR 10 into the intervertebral space. Each of the upper and lower gripping surfaces 12, 14 includes a plurality of gripping members such as teeth 16 for engaging with and into the adjacent vertebrae. The shape of the teeth 16 additionally promotes the arcuate or multi-directional insertion path of the VBR 10 into the intervertebral space.

As best seen in FIGS. 1 and 2, the teeth 16 are arrayed in one or more rows 40, each of which is parallel to the other rows 40 and parallel to a direction T. The rows 40 of teeth 16 are separated by a groove, cut, or channel 42, while adjacent teeth 16 of the same row 40 are separated by a comparatively small depression 44. Preferably, the channels 42 are significantly deeper and wider than the depressions 44. Thus, the rows 40 of teeth 16 form a kind of a saw-toothed ridge. As a result, for any particular row 40 of teeth 16 moving across the vertebral surface, a first tooth 16 will reduce the resistance experienced by a subsequent tooth 16 of that particular row 40. In contrast, portions of the vertebrae are received in the channels 42 due to the cutting and embedding nature of the rows 40 of teeth 16. These portions of the vertebrae impede the movement of the VBR 10 in a direction along the vertebral surface other than along direction T.

The direction T is selected to promote insertion of the VBR 10 into the intervertebral space in a desired orientation. As can further be seen in FIG. 2, the rows 40 are generally parallel to the direction T, which is positioned with respect to the longitudinal axis 18 by an angle α1. Each tooth 16 rises, crest-like, from the body portion 26 to a tip 48 and has a length L1 and a width W1. A side surface 17 extends along each row formed by the channels therebetween. These large side surfaces 17 generally face the insertion end 30 of the body 26 and include upper portions 19 associated with each tooth 16 that extends along the length L1 of the tooth 16 parallel to the direction T.

Due to the anatomy of a patient, it is common and desirable to implant intervertebral fusion devices from an anterior or posterior-lateral direction, that is, from a direction offset from the lateral or anterior-posterior sides. The implant is inserted into the intervertebral space from this direction, and then the implant is manipulated into the desired orientation during insertion of the implant into the intervertebral space.

With the present VBR 10, the described configuration for the teeth 16 allows one to apply force to the VBR 10 (for example, in a direction parallel to the longitudinal axis 18 of the VBR) from a lateral direction of the intervertebral space. The application of insertion force parallel to the longitudinal axis 18 is generally required due to the configuration and rigidity of the connection provided between the implant body 26 and an insertion tool 120 as described hereafter. The insertion end 30 is initially guided into the intervertebral space so that the leading surfaces 17 of the teeth 16 engage the vertebral surfaces. When force is directed parallel to the longitudinal axis 18 and the teeth 16 engage the vertebral surfaces, the body 26 receives the least resistance to movement in the direction parallel to the leading surfaces 17 and to the direction T. Thus, the side surface 17 serve as camming surfaces causing the VBR 10 to move at the angle α1 between the direction T and the longitudinal axis 18. In one form, the angle α1 is approximately thirty degrees.

The rows 40 may be positioned a distance from each other to increase resistance in a direction other than along direction T. That is, the channels 42 between the rows 40 have a width W2 greater than a width W3 of the depressions 44. The simplest manufacturing technique for the VBR 10 results in teeth 16 being formed so that each generally aligns with teeth 16 of adjacent rows 40. Specifically, forming the teeth 16 may be done by providing the VBR body 26 without the teeth 16, drawing a cutting tool in parallel lines across the VBR body 26 to cut the channels 42 therein, and drawing a cutting tool in parallel lines across the VBR body 26 to cut the depressions 44 therein.

As discussed above, aligning the teeth 16 in the rows 40 allows the teeth 16 to cut into the surface of the vertebrae. However, the large distance between the rows 40 (width W2) reduces or eliminates the tendency for the teeth 16 spanning from one row 40 to another row 40 to form a cutting ridge. By spacing the rows 40 as described, resistance to motion in a direction transverse to the rows 40 is significantly greater than along the rows 40.

The configuration of individual teeth 16 additionally assists in steering the VBR 10 into the desired position within the intervertebral space. As noted above, during insertion of the VBR 10, the teeth 16 form grooves in the vertebral surfaces, which helps prevent the VBR 10 from moving in a direction other than the along direction T. Once the leading portion of the VBR 10 is within the intervertebral space, the implant will typically need to be rotated as it moves ahead. If the teeth 16 are too large or formed in a continuous ridge, as shown for example, in U.S. Patent Application Publication No. 2003/0073998, then the rotation of the VBR 10 becomes more difficult, because the trailing ridges have to bluntly scrape across the vertebral surfaces when turning into position toward the desired implantation orientation.

With the present VBR 10, the rows 40 are not continuous ridges. Teeth 16 are interrupted by depressions 44 as well as much larger cavities 62, 64. These interruptions reduce the continuity of the rows 40 thereby reducing the force needed to rotate the VBR 10 against the grooves formed in the vertebral surfaces. In one form, the interruptions are directed generally parallel to the turning path of the VBR 10.

Prior to implantation, surgical procedures are performed to prepare the intervertebral space between the adjacent vertebrae. More specifically, the spinal disc includes an annulus and a nucleus positioned between and secured with the adjacent superior and inferior vertebrae. The nucleus and the annulus may be substantially removed, or a portion of the annulus may be retained to assist in retaining bone graft material which will be discussed below.

The vertebral endplates may be prepared with scraper or rasp. The endplates are naturally cup-like having a natural concavity in both the lateral direction and the anterior-posterior direction. Preparation of the endplates may include providing a desired contour to the vertebral surfaces within the intervertebral space and roughening and violating the vertebral surfaces to induce bleeding. Once the VBR 10 and graft material are implanted within the intervertebral space, closely-matched contours between upper and lower gripping surfaces 12, 14 reduce the likelihood of bone subsidence around the VBR 10 by distributing compressive forces across the upper and lower gripping surfaces 12, 14. Violation of the vertebral surfaces promotes purchase by or embedding of the teeth 16 within the vertebral surfaces. Inducing vertebral bleeding promotes bone growth from the vertebrae and between the bone graft material and the vertebrae.

Figure 3:
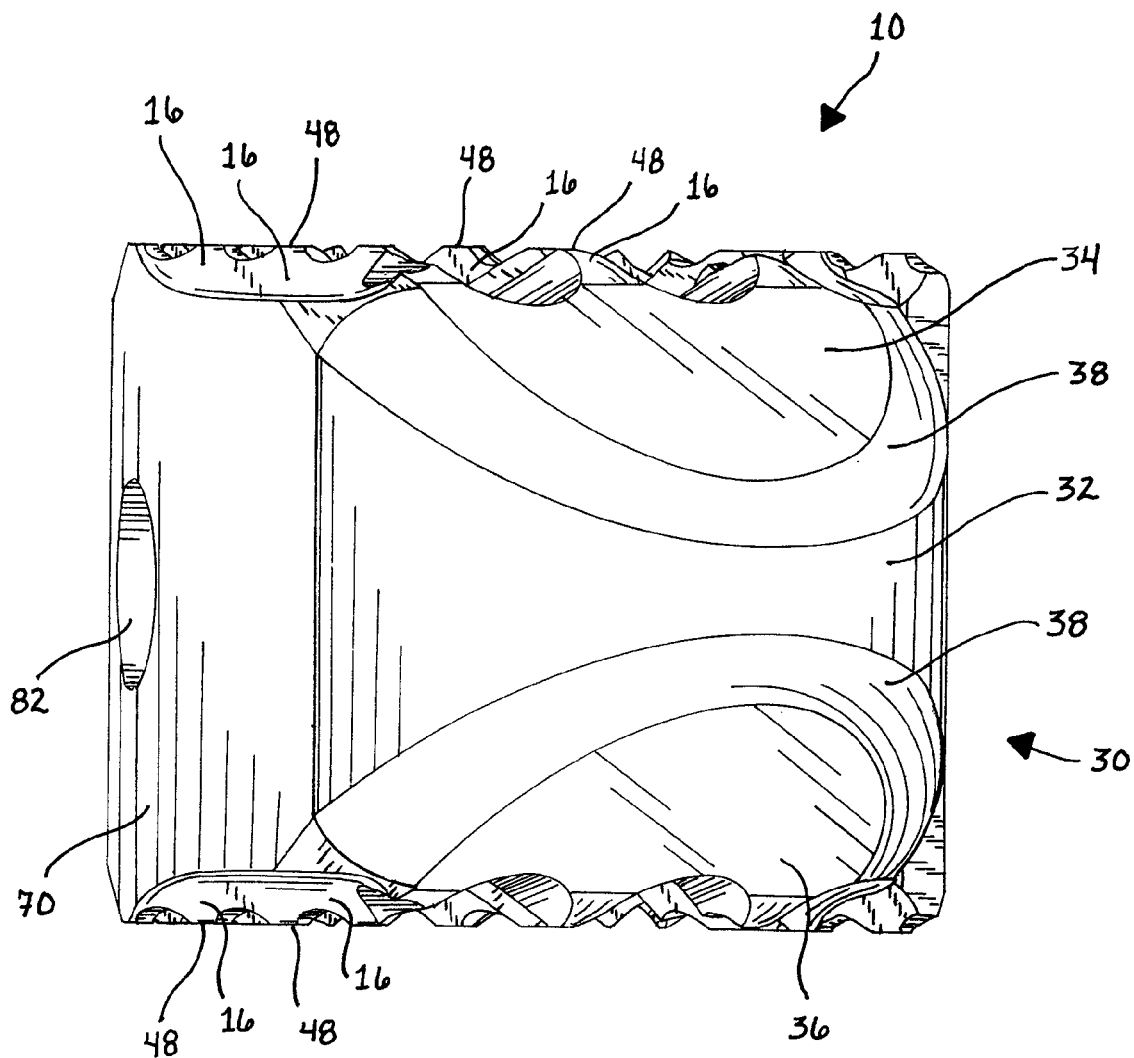
FIG. 3 is a elevational view of the VBR device of FIG. 1 taken along the line 3-3 of FIG. 2 showing a leading insertion end of the implant body having a wedge shaped configuration for ease of insertion into the intervertebral space.
Figure 4:
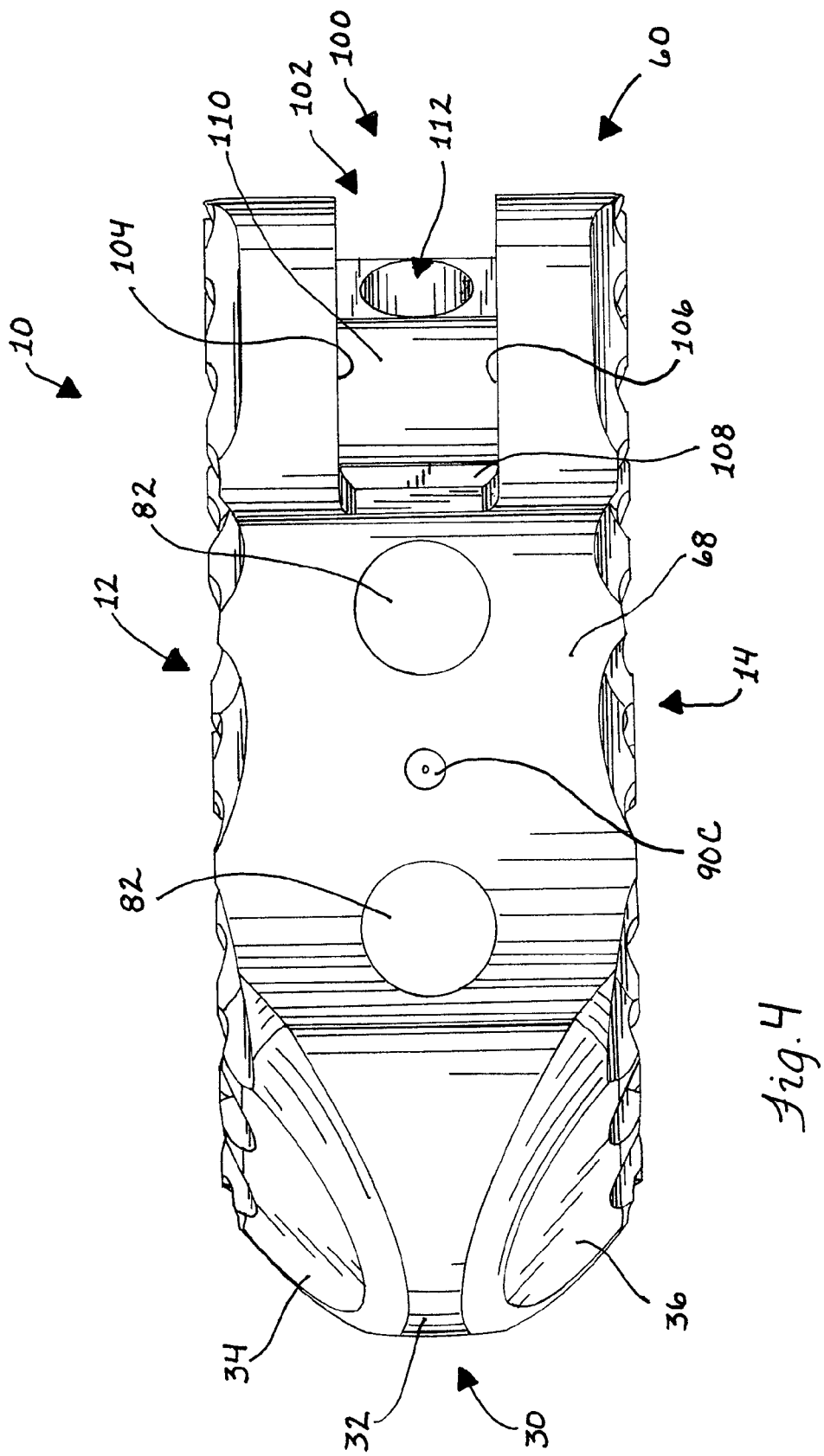
FIGS. 4 and 5 are side elevation views of the VBR device of FIG. 1 showing throughbores in the walls for allowing bone growth through the VBR device and into the cavities, the orientation of the insertion end and the trailing end with respect to the longitudinal axis of the VBR device, and a horizontal radiographic marker.
Figure 5:
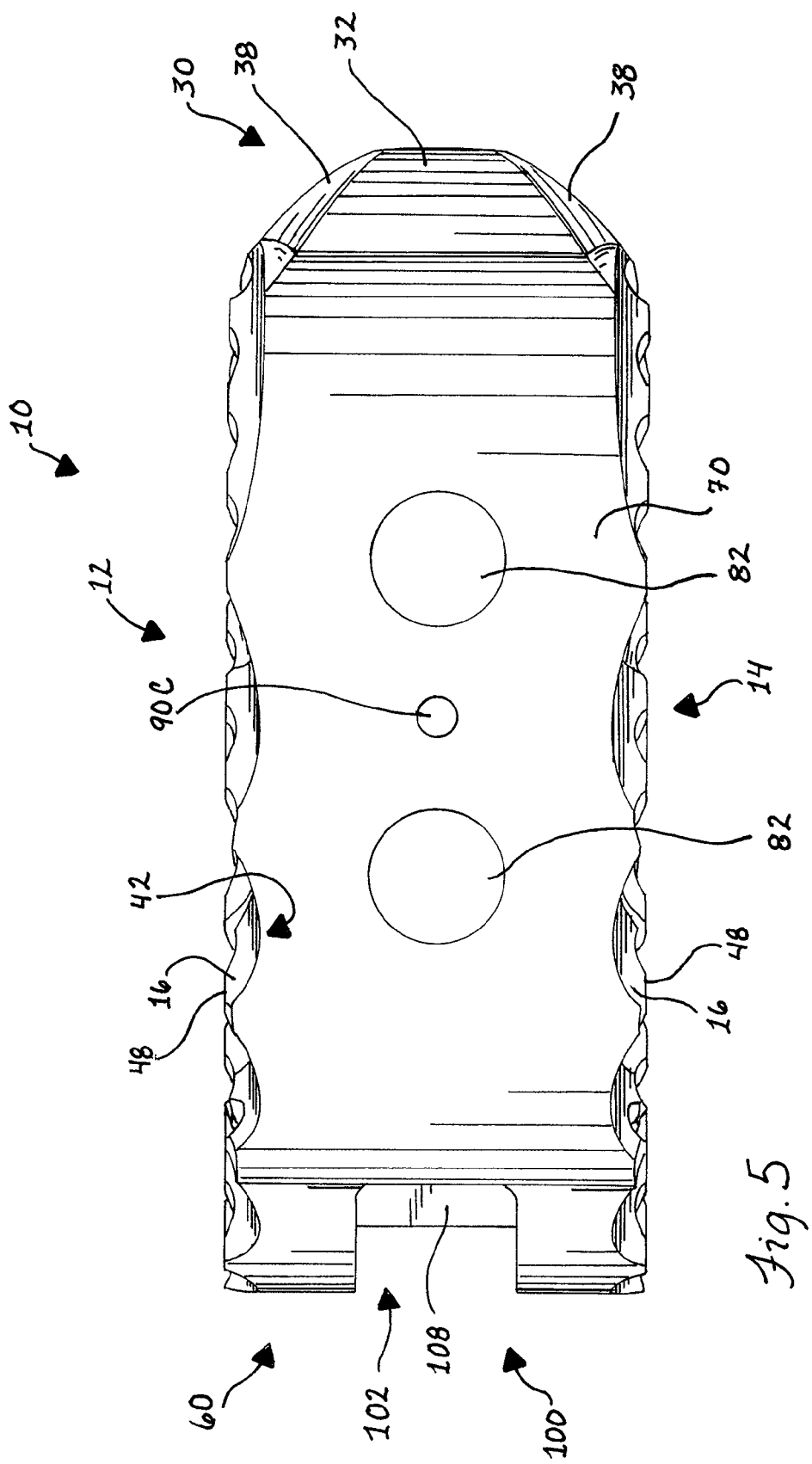

As can be seen in FIGS. 3-5, the upper and lower gripping surfaces 12, 14 are generally level, as opposed to concave or convex. The teeth 16 extend from or, alternatively, are cut from the VBR body portion 26. The teeth 16 terminate at the tip 48, and each tooth 16 extends from the body portion 26 to its tip 48 generally in equal measure. Relative to the tooth tips 48, the depth of each depression 44 is generally equal in measure, as is the depth of each channel 42. With this shape, the preparation of the vertebral endplates preferably includes flattening so that the teeth 16 each embed approximately an equal amount into the vertebrae, and the risk of bone subsidence around the VBR 10 is minimized.

As best seen in FIGS. 1 and 2, the VBR 10 includes a pair of cavities 62, 64 for receiving bone graft material therein. The bone graft material allows bone growth and formation between the vertebrae such that the vertebrae are fused. The cavities 62, 64 allow the bone formation to extend through and around the VBR 10. The body portion 26 extends from the insertion end 30 and through the trailing end 60 with the upper and lower gripping surfaces 12, 14 formed thereon. The cavities 62, 64 are defined by the body portion 26 which includes a leading portion 66 adjacently located to the insertion end 30, a curved inner wall 68, a curved outer wall 70, and a septum 72. As noted above, the VBR 10 spans across large area of the intervertebral space, and the cavities 62, 64 may also be sized accordingly for accommodating a large amount of bone graft material. The septum 72 provides additional support to the vertebrae to resist bone subsidence. Preferably, the cavities 62, 64 are packed with bone graft material prior to complete insertion within the intervertebral space. The cavities 62, 64 are open towards the superior and inferior vertebrae so that the bone graft material in each cavity 62, 64 fuses not only with itself but also with each of the adjacent vertebrae.

The VBR 10 further includes throughbores 82 for promoting fusion and bone growth therethrough. The inner and outer walls 68, 70 each include two throughbores 82 communicating with respective cavities 62, 64. Bone graft material is packed around the implanted VBR 10, and the throughbores 82 allow fusion to occur therethrough so that the material around the VBR 10 may fuse with the material within the cavities 62, 64.

Figure 6:
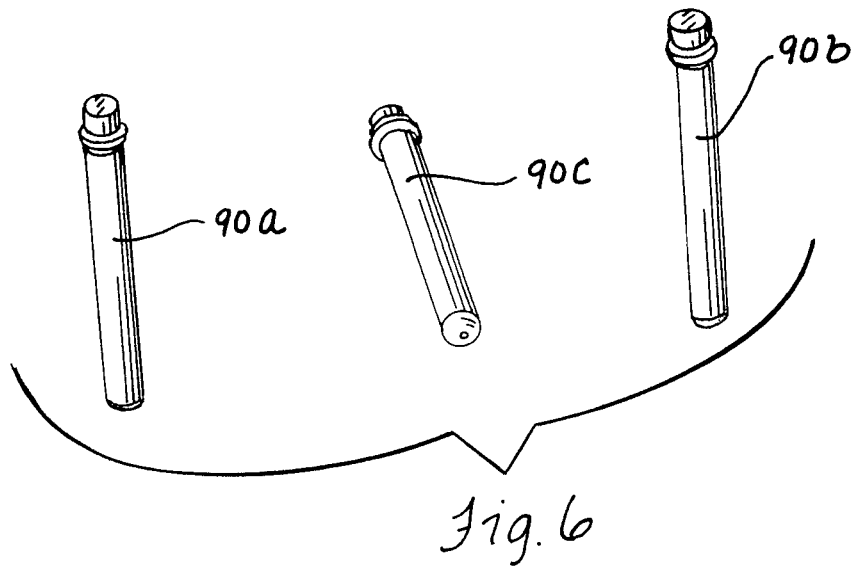
FIG. 6 is a perspective view of a relative position and orientation of the radiographic markers.

The VBR 10 includes radiographic markers 90 embedded in the body portion 26. These markers 90 allow a surgeon to use radiographic equipment to identify the location and orientation of the VBR 10 within the intervertebral space, including identifying the height, length, and width of the VBR 10. As can be seen in FIG. 2, two markers 90a and 90b are oriented generally vertically. A third marker 90c is oriented in a generally horizontal manner, as shown in FIG. 4, for instance. With specific reference to FIG. 6, the relative orientation of the markers 90a, 90b, 90c is shown. The markers 90 are preferably formed of tantalum but may be formed of any suitable radiographic material.

The VBR trailing end 60 includes a socket 100 cooperable with a number of instruments to allow a surgeon to implant and manipulate the VBR 10, such as an insertion tool 120 depicted in FIGS. 7-15. The socket 100 is generally symmetrical in the horizontal direction, though it may alternatively be asymmetrical so that a particular relative orientation is required for coupling the VBR 10 and the insertion tool 120.

The insertion tool 120 is used to insert the VBR 10 within the intervertebral space, and may be used for manipulation of the VBR 10 within the intervertebral space. To enable this, a distal end 126 of the insertion tool 120 and the VBR 10 are coupled in a releasable fixed orientation. The insertion tool distal end 126 and the VBR socket 100 are coupled so that a surgeon may apply force to the insertion tool 120 without the VBR 10 separating therefrom.

As shown in FIGS. 61 and 62, when the insertion tool 120 and the VBR 10 are coupled, the longitudinal axis 18 of the VBR 10 is transverse to a shaft portion 125 of the insertion tool 120. More, specifically, the longitudinal axis 18 of the VBR is offset from the shaft portion 125 by an angle β. In the illustrated form, the angle β is approximately 30°. The angle between the VBR 10 and the shaft portion 125 permits angled insertion of the VBR 10 such as the in the situation, described above, where the VBR is inserted from an anterior or posterior-lateral direction.

Figure 59:
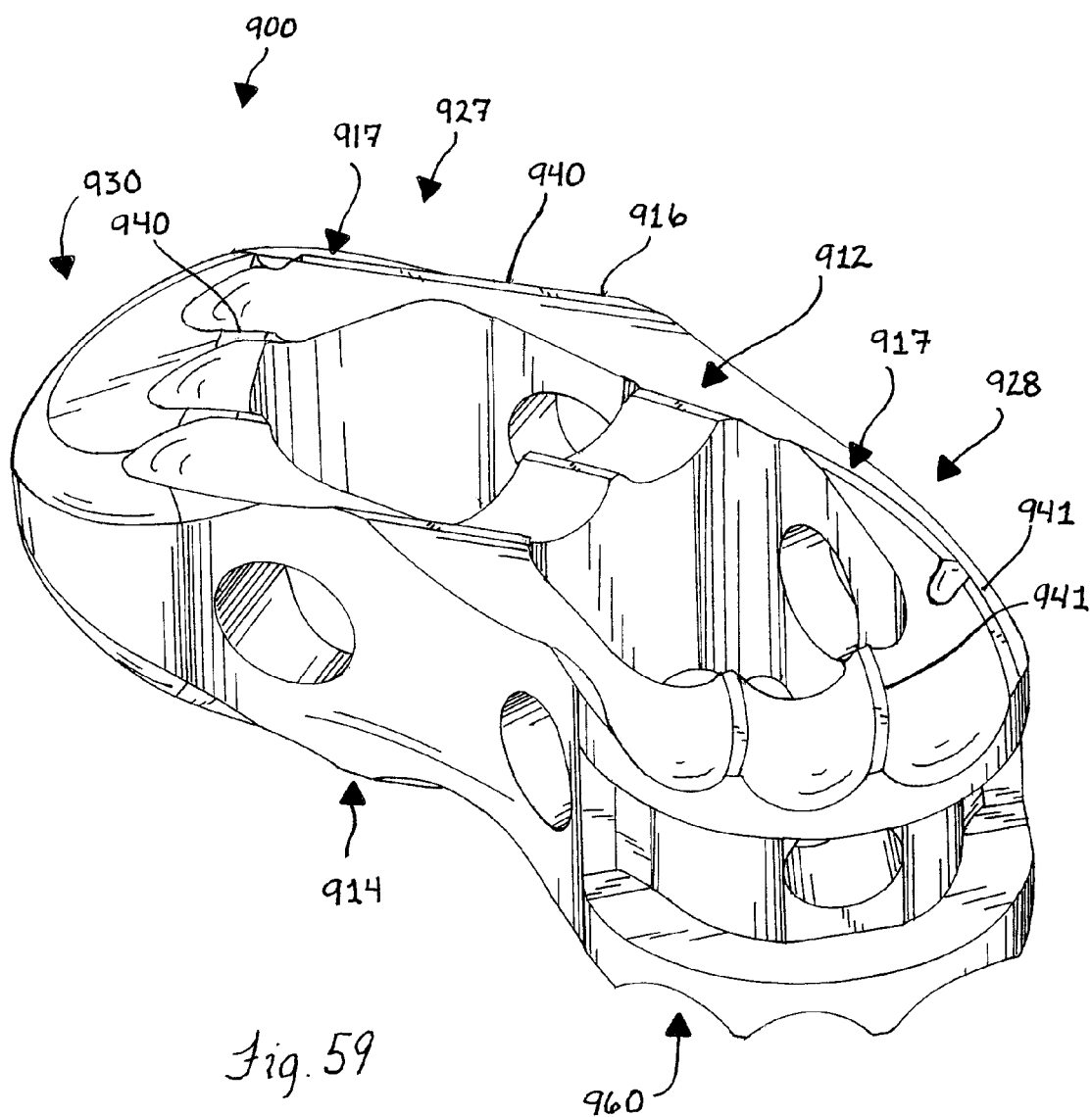
FIG. 59 is a perspective view of an alternative configuration of the VBR device of FIG. 1 having rows of gripping members at the trailing end portion of the VBR device having an arcuate configuration.
Figure 60:
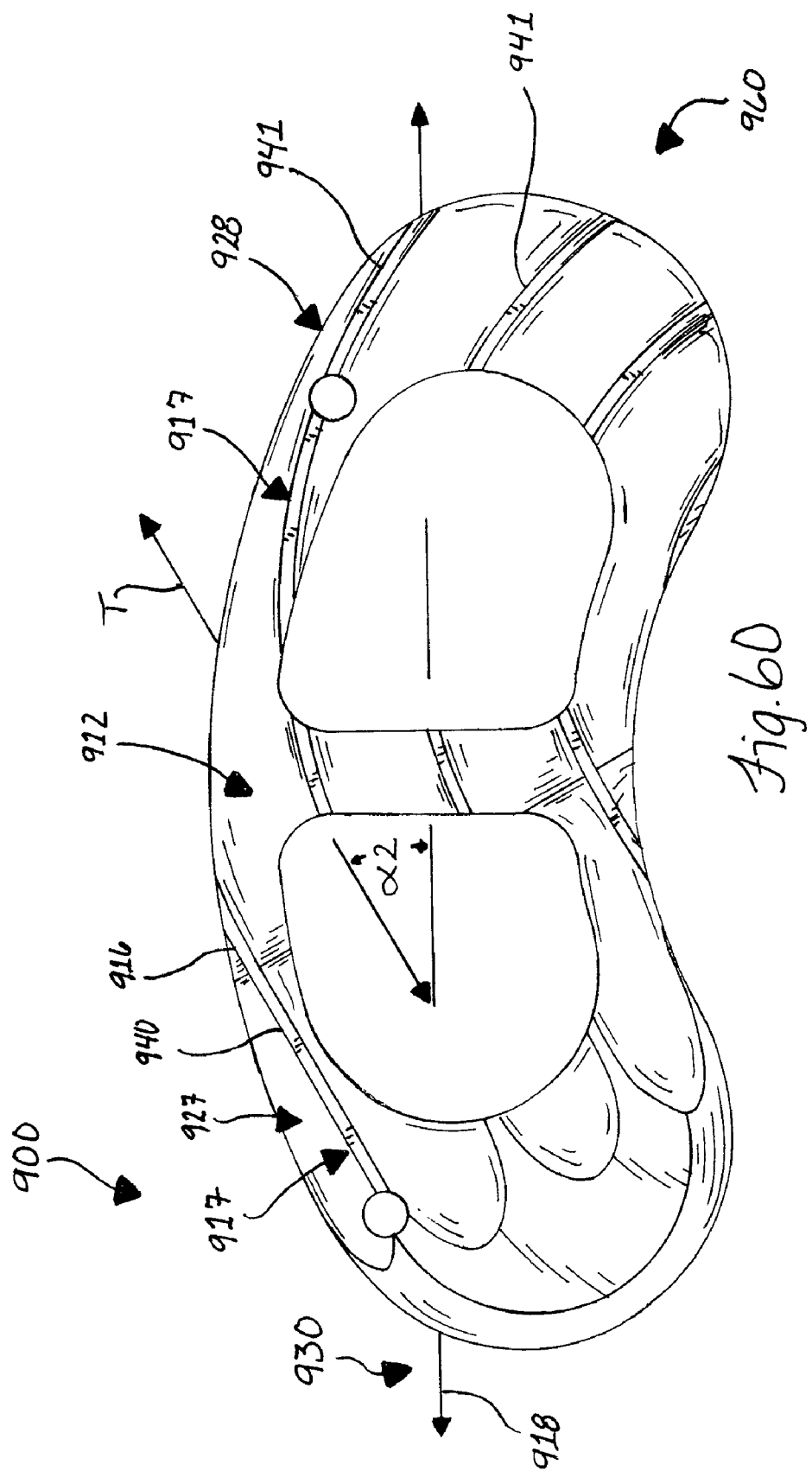
FIG. 60 is a plan view of the VBR device of FIG. 59.

Referring to FIGS. 59 and 60, an alternative configuration of the VBR 10 is shown. VBR 900 includes the features described herein with respect to VBR 10, including, but not limited to, a body 926 having an insertion end 930, a trailing end 960, a generally concavo-convex configuration along a longitudinal axis 918, and upper and lower gripping surfaces 912, 914 having a plurality of gripping members for engaging with and into the adjacent vertebrae. The gripping members 916 of the VBR 900 may include spaced teeth like the teeth 16 of the VBR 10. Alternatively, as illustrated in FIGS. 59 and 60, the VBR may include rows of gripping members 916 that do not have depressions separating individual adjacent teeth. In either case, the gripping members 916 of the VBR 900 are arranged on the implant body 926 differently than teeth 16 of the VBR 10.

Specifically, the VBR 900 includes a first set of rows 927 of gripping members 916 near the insertion end of the VBR 900 and a second set of rows 928 of gripping members 916 near the trailing end of the VBR 900. The first set of rows 927 are arrayed in one or more rows 940 similar to rows 40 of VBR 10. Like rows 40, rows 940 are positioned parallel to one another and parallel to a direction T. A side surface 917 extends along each row formed by the channels parallel to the direction T. The large side surfaces 917 generally face the insertion end 130 of the body 926.

The direction T, which is positioned with respect to a longitudinal axis 918 of the VBR 900 by an angle α2, is selected to promote insertion of the VBR 900 into the intervertebral space at a desired insertion direction. Thus, as the VBR 900 is inserted into the intervertebral space, the leading surface of the gripping members 916 in rows 940 engage the vertebral surfaces and serve as camming surfaces to guide the VBR into the intervertebral space. When force is directed parallel to the longitudinal axis 918, the rows 940 of gripping members 916 engaged with the vertebral surfaces frictionally bias the VBR 900 to move into the intervertebral space at the angle α between the direction T and the longitudinal axis 918. In one form, the angle α2 is approximately 30°.

The second set of rows 928 of gripping members 916 are arrayed in one or more rows 941. Rows 941 are aligned generally parallel to one another but generally transverse to rows 940. In one form, the rows 941 have an arcuate or curved configuration such that the curvature of the rows 941 is generally aligned with the desired turning path of the VBR 900. Thus, rather that being parallel to the direction T, the side surfaces 917 of the gripping members 916 in the rows 941 are generally aligned with the desired turning path of the VBR 900. Accordingly, the rows 941 of gripping members 916 frictionally bias the VBR towards its final predetermined implantation orientation within the intervertebral space and reduce the force needed to rotate the VBR 900 against the grooves formed in the vertebral surfaces.

As shown in FIGS. 59 and 60, rows 940 and 941 of gripping members 916 are separated by channels similar to the channels 42 described above with respect to the VBR 10. Although not shown, spaced teeth may also be separated by depressions, similar to the depressions 44 described with respect to the VBR 10.

With reference to FIGS. 73-76, another alternative embodiment of the VBR 10 is shown. VBR 1300 includes the features described herein with respect to the VBR 10, including a body 1336 having an insertion end 1330, a trailing end 1360, a curved inner wall 1368, a curved outer wall 1370, and upper and lower gripping surfaces 1312, 1314.

Figure 75:
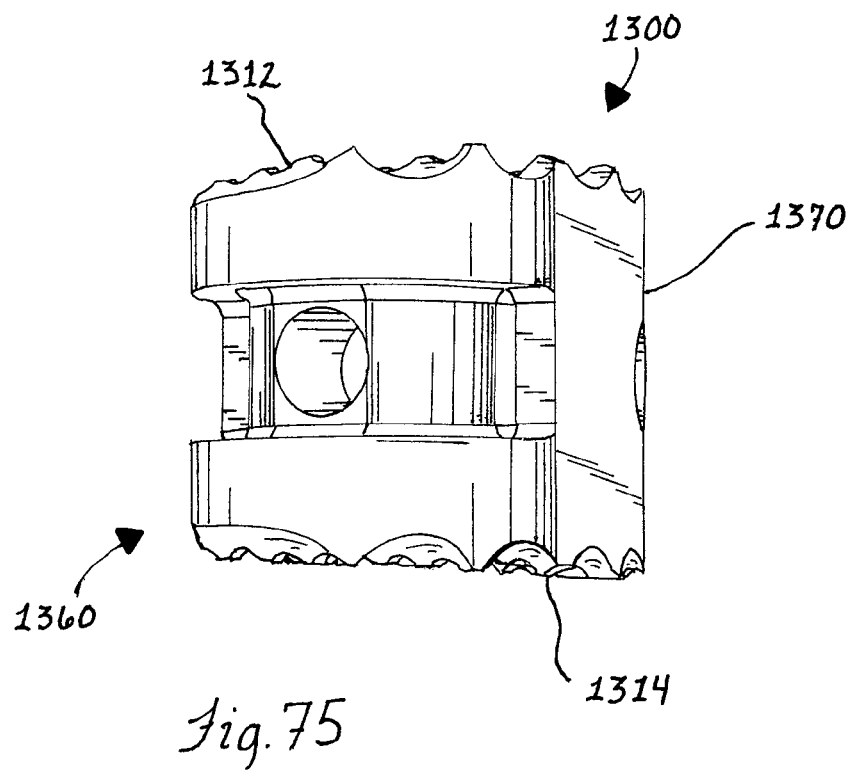
FIG. 75 is a side elevation view of the VBR device of FIG. 73.

As shown in FIGS. 75-76, the VBR 1300 has a variable height extending between the upper and lower gripping surfaces 1312, 1314. More specifically, the upper and lower gripping surfaces 1312, 1314 are slanted with respect to one another such that the VBR 1300 has a first height H1 at the center of the curved inner wall 1368 and a second height H2 at the center of the curved outer wall 1370 that is greater than the first height H1. Thus, the upper and lower gripping surfaces 1312, 1314 are disposed at an angle $\alpha 3$ to one another. The angle $\alpha 3$ is preferably selected to provide the body 1326 a degree of lordosis generally corresponding to the natural lordosis of the spine. In one form, the angle $\alpha 3$ is approximately six degrees.

Figure 8:
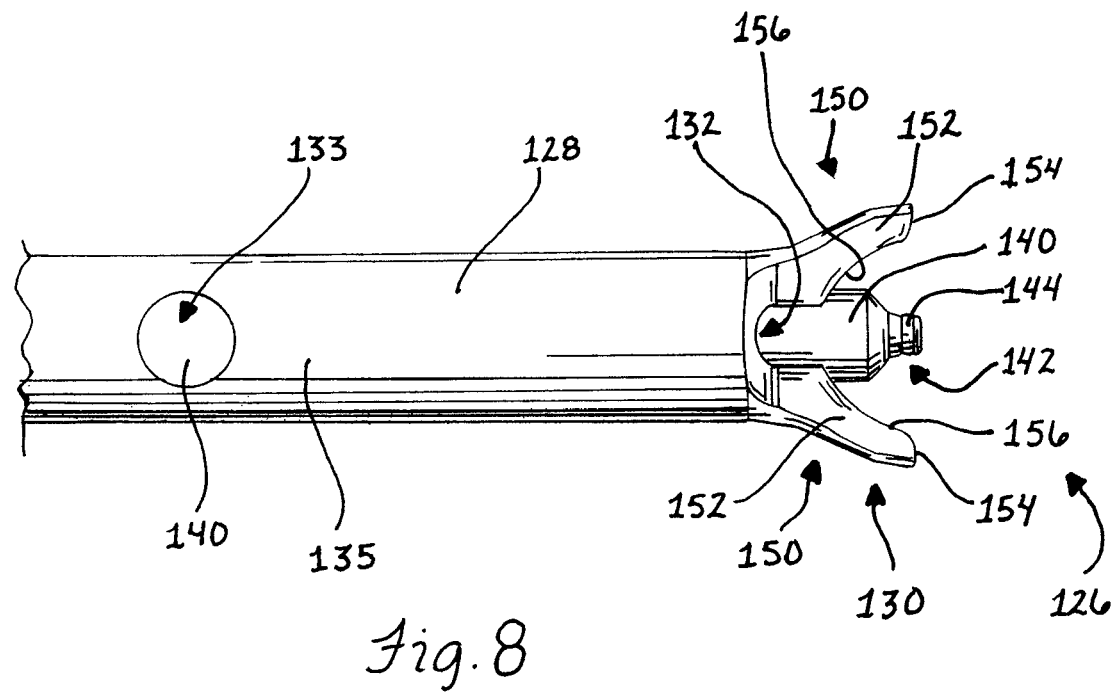
FIG. 8 is a fragmentary side elevation view of the engagement end of the insertion tool of FIG. 7 showing a pair of C-shaped arms formed on the outer sheath, the arms being receivable within the socket of the tool-engagement end of the implant body, and a rod generally located within a central longitudinal throughbore of the sheath and having a threaded end received within a threaded bore of the socket for securing the VBR device with the engagement end of the insertion tool.
Figure 9:
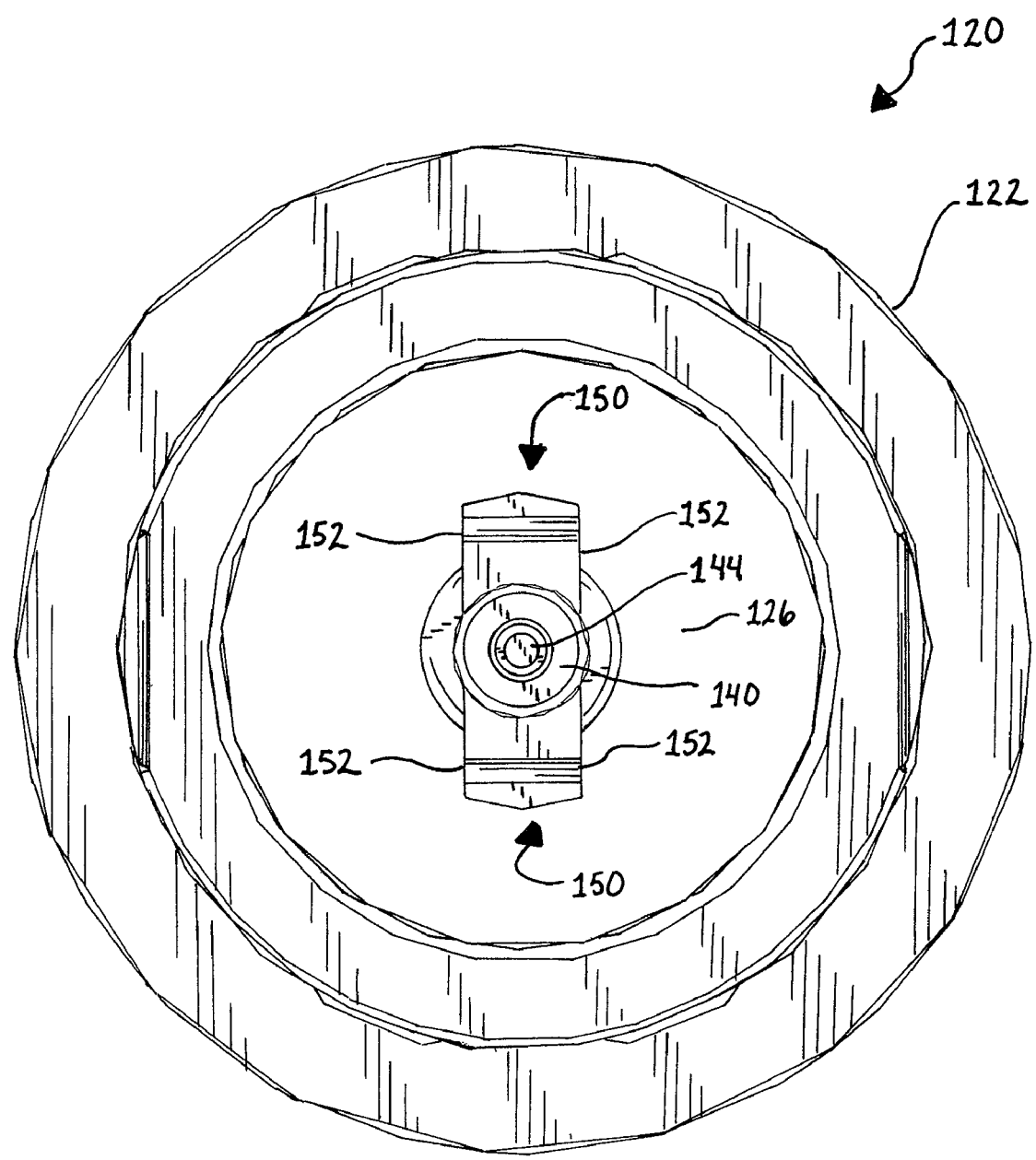
FIG. 9 is a side elevation view of the engagement end of the insertion tool of FIG. 7 showing generally flat sides on the arms for closely fitting within the socket in the implant body.

Referring to FIGS. 7 and 8, the insertion tool 120 has a handle portion 124 with an outer grip portion 122 allowing a surgeon to manipulate the coupled VBR 10 and insertion tool 120. Extending from the handle portion 124 is the shaft portion 125 including a sheath portion 128 with a distal end 130 engageable with a portion of the VBR socket 100. The sheath portion 128 includes a longitudinal throughbore 132 in which a rod 140 is received. The rod 140 has an outer diameter sized to permit the rod 140 to easily rotate or reciprocate within the throughbore 132, and a distal end 142 with a threaded portion 144. As some material may enter the insertion tool 120 between the rod 140 and the sheath portion 128, within the throughbore 132, a series of ports 133 extending from an outer surface 135 to the throughbore 132 are formed in the sheath portion 128 to allow cleaning and sterilization of the insertion tool 120, such as by autoclaving.

The insertion tool distal end 122 is coupled with the VBR 10 by engaging the rod threaded portion 144 and the sheath portion distal end 130 in the socket 100. The sheath portion distal end 130 includes a pair of curved arms 150 extending outward from the sheath portion 128 forming a crescent-like structure. As best seen in FIG. 1, the socket 100 includes an arcuate recess 102 formed in the trailing end 60 in which the curved arms 150 and rod threaded portion 144 are received.

The socket arcuate recess 102 and insertion tool curved arms 150 are closely matched in shape so that, when the VBR 10 and insertion tool 120 are coupled, a number of surfaces and sides are in close abutment. The curved arms 150 have flat sides 152 (FIG. 9) which are closely received within and against upper and lower recess surfaces 104 and 106 formed in the socket 100 (FIG. 4). Each curved arm 150 each has a flat terminal surface 154 (FIG. 8) which abuts a respective vertical recess surface 108 spanning between the upper and lower recess surfaces 104, 106 in the socket 100 (FIG. 1). The curved arms 150 also have arcuate inner surfaces 156 (FIG. 8) for engaging with a curved inner surface 110 of the socket 100 (FIG. 1). The close fit of the socket 100 and the curved arms 150 allows the VBR 10 to be easily manipulated by the insertion tool 120.

As noted, the rod threaded portion 144 also engages in the socket 100. The socket 100 includes a threaded bore 112 (FIGS. 1 and 4) into which the threaded portion 144 is directed. As the threaded portion 144 advances into the bore 112, the curved arms 150 are drawn into the socket recess 102. Thus, tightening of the rod threaded portion 144 in the threaded bore 112 presses the curved arms 150 into the socket recess 102, and the threaded cooperation generally inhibits separation of the VBR 10 from the insertion tool 120.

As noted above, the rod 140 is permitted to rotate and reciprocate within the sheath portion throughbore 132. With reference to FIGS. 10-13, the rod 140 is adjusted via a knob 160. As best seen in FIGS. 12 and 13, the rod 140 has a proximal end 162 having a connection portion 164 including flats 166 formed thereon. The connection portion 164 is received within an opening 168 formed in the knob 160 so that the knob 160 and the rod 140 co-rotate. By rotating the knob 160, the rod threaded portion 144 is threaded into or out of the threaded bore 112 of the VBR socket 100. As this occurs, the engagement between VBR socket 100 and the curved arms 150 of the sheath portion distal end 130 prevent rotation of the sheath portion 128 relative to the VBR 10 so that the rod 140 is required to shift longitudinally relative to the sheath portion 128.

Figure 10:
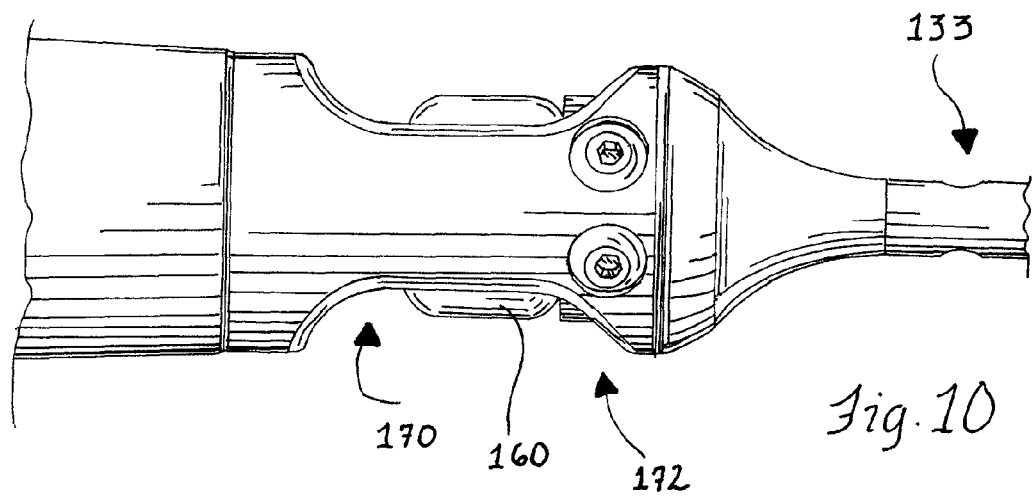
FIG. 10 is a fragmentary side elevation view of the insertion tool of FIG. 7 showing a knob secured with the rod for rotation thereof, and a window formed in the handle of the insertion tool allowing manual access to the knob.
Figure 11:
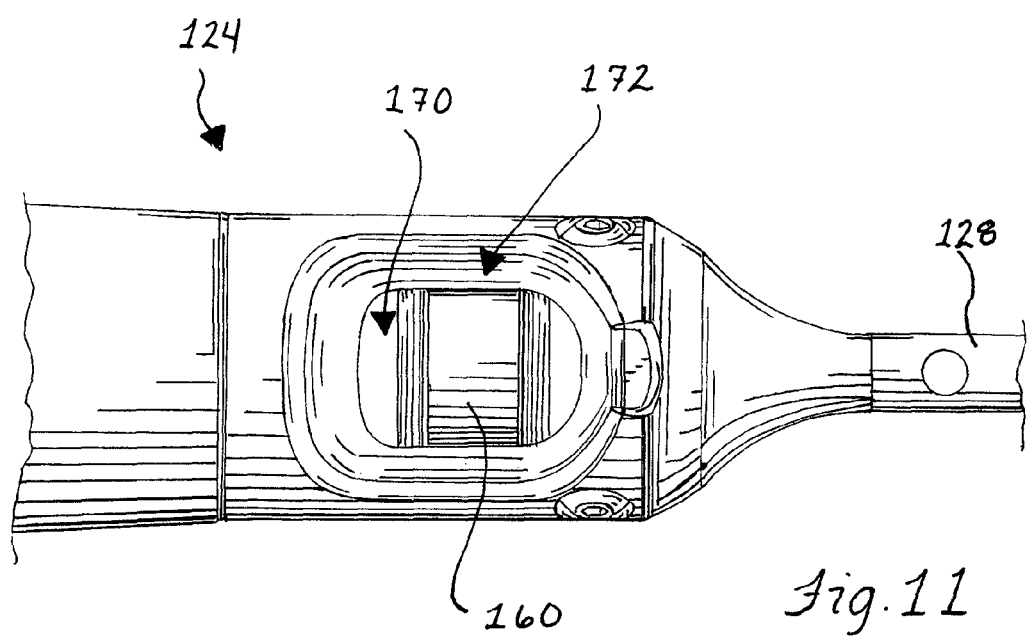
FIG. 11 is a side elevation view of the insertion tool as shown in FIG. 10 rotated ninety-degrees showing a cavity formed in the handle for receiving the knob therein and permitting the knob to be longitudinally adjusted relative to the handle and sheath.

As can be seen in FIGS. 10 and 11, the handle portion 124 includes a cavity 170 in which the knob 160 is located. One or more windows 172 are formed in the handle portion 124 allowing manual access to the knob 160, which protrudes from the cavity 170 and through the windows 172, best seen in FIG. 10. The cavity 170 is larger in the longitudinal direction than the knob 160, and the size difference accommodates the longitudinal shifting of the knob 160 within the cavity 170.

Figure 14:
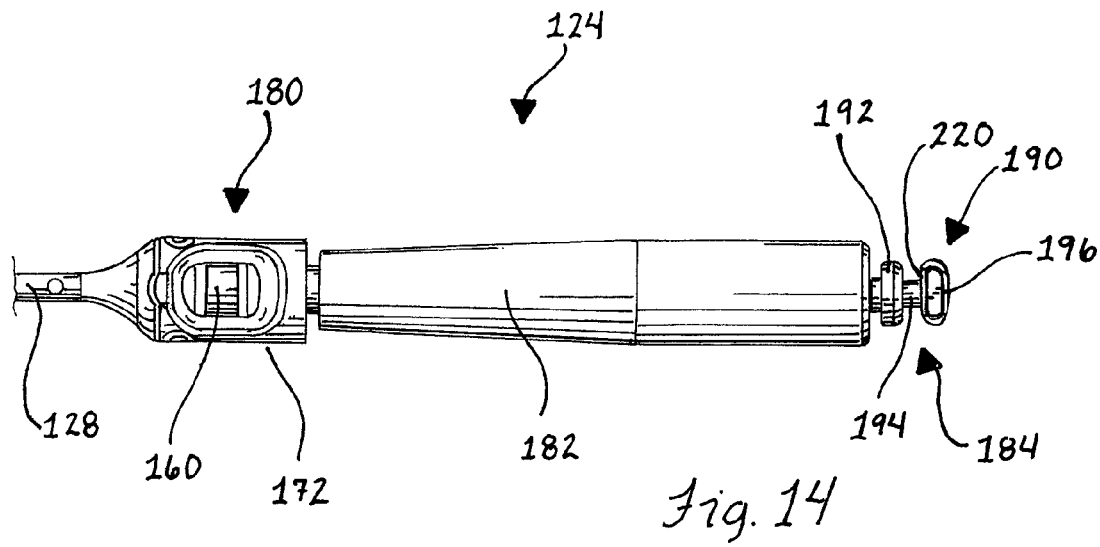
FIG. 14 is a fragmentary side elevation view of the insertion tool of FIG. 7 with a grip portion of the handle removed to show a solid central portion of the handle extending between the window and a connection end formed on a proximal end of the insertion tool, the connection end securable with a hammer instrument for directing a VBR device connected with the insertion tool into an intervertebral space.

Referring now to FIG. 14, the handle portion 124 of the insertion tool 120 is shown with the grip portion 122 removed. The handle portion 124 includes a distal portion 180 including the cavity 170 and windows 172 for operating the knob 160 and rod 140. The distal portion 180 is secured with the sheath portion 128 and with a handle body portion 182, which in turn is secured with a connection end 184. Each of the sheath portion 128, distal portion 180, handle body portion 182, and connection end 184 is generally rigid so that force applied to the handle portion 124 is transmitted through to a VBR 10 coupled with the insertion tool distal end 126.

Figure 16:
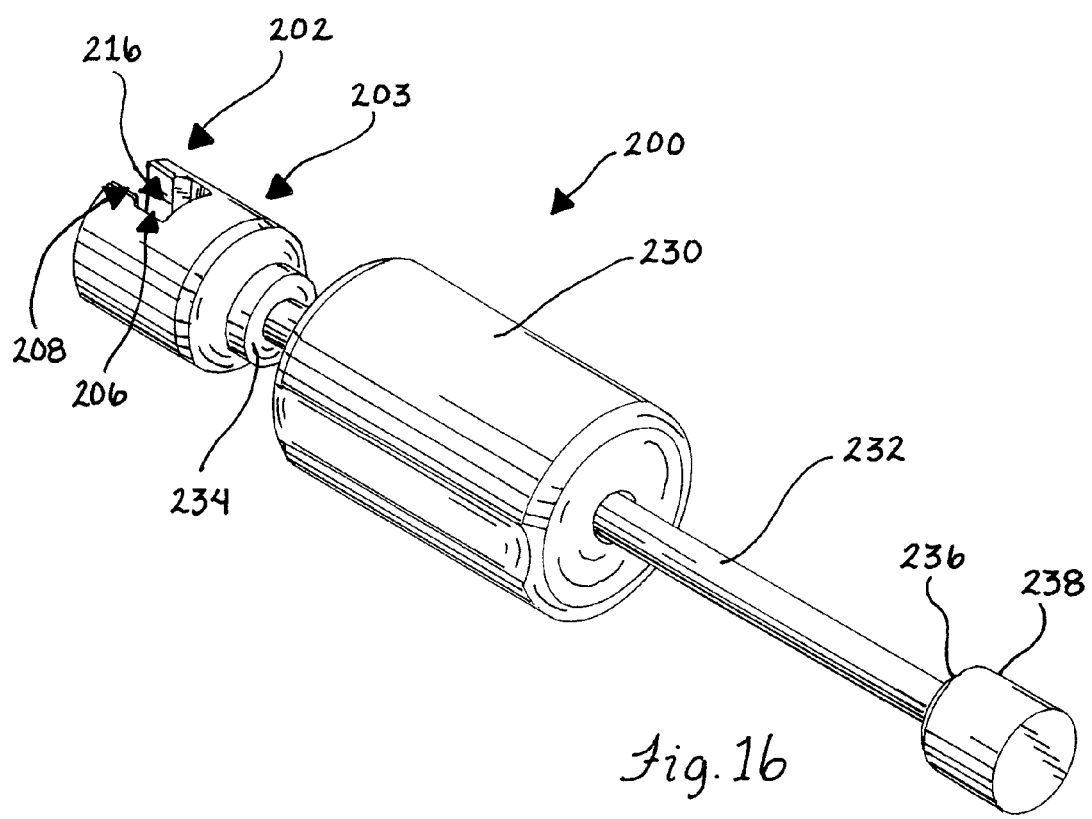
FIG. 16 is a perspective view of a hammer instrument for providing force to the insertion tool for manipulating a VBR device into or within an intervertebral space, the hammer instrument having a hammer member reciprocable along a shaft for guiding an impact of the hammer member.

More specifically, the connection end 184 allows a driving instrument such as a hammer instrument 200, depicted in FIG. 16, to be secured with the insertion tool 120. The generally rigid structure of the insertion tool 120 allows force applied by the hammer instrument 200 against the connection end 184 to be transmitted to the VBR 10 for manipulating its position. Preferably, the hammer instrument 200 is a slap-hammer-type device such that the impact force can be easily controlled, as will be discussed below.

Figure 19:
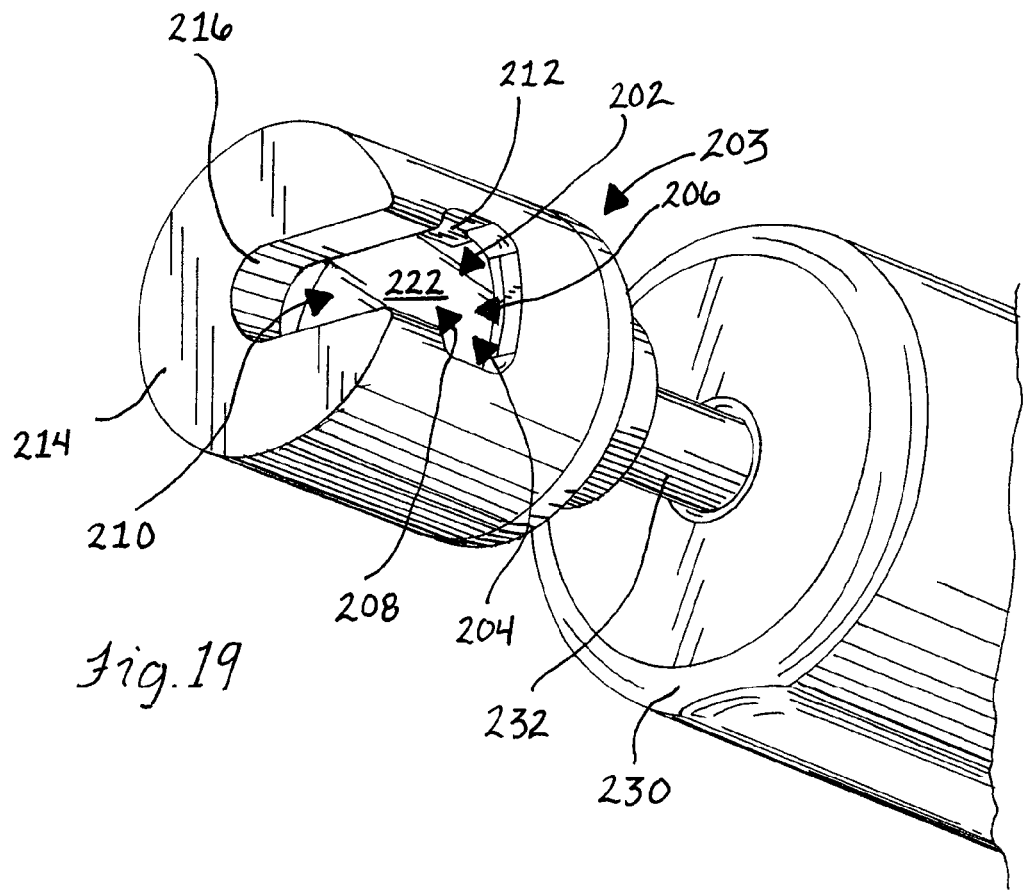
FIG. 19 is an enlarged perspective view of the connection end of the hammer instrument showing a side keyhole opening having a slot and enlarged portions respectively permitting the shank and head of the insertion tool connector to be inserted therethrough, and showing an inner cavity for receiving the head, the cavity defined by a cylindrical wall and an end wall.
Figure 20:
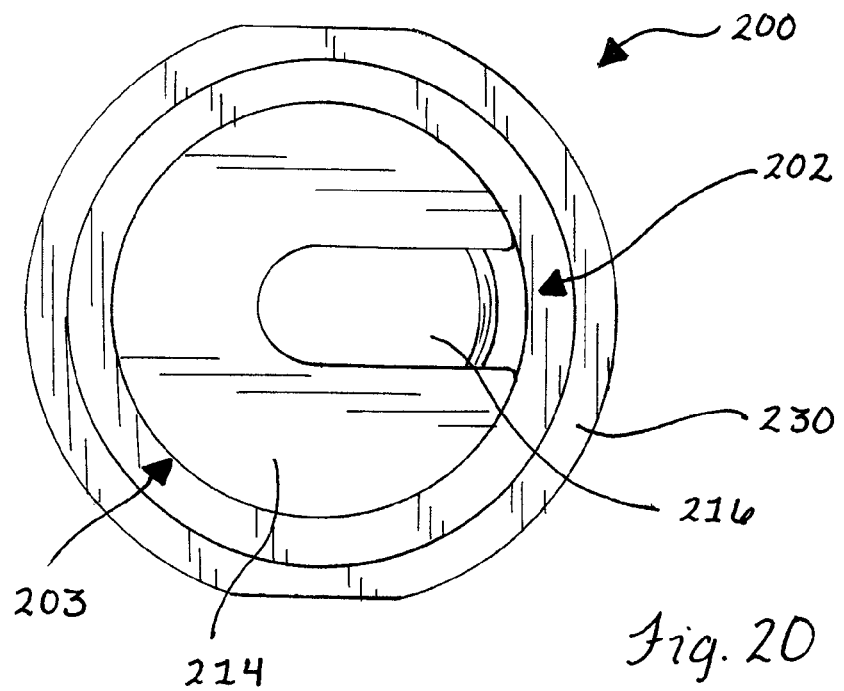
FIG. 20 is a side elevation view of the connection end of the hammer instrument showing a channel formed in the end wall sized to allow the insertion tool shank to pass therealong while preventing the insertion tool head to pass therethrough.

The insertion tool connection end 184 includes a connector 190 received within a socket 202 of the hammer instrument 200 (FIG. 16). The connector 190 includes a base 192 secured around a shank 194, and an enlarged head 196 at a proximal end of the connector 190. The socket 202 of the hammer instrument 200 is formed in a hammer connection end 203 and includes a longitudinally oriented keyhole opening 204. The keyhole opening 204 has a lower enlarged portion 206 for allowing the connector head 196 to pass therethrough, and an upper slot portion 208 which permits passage of the connector shank 194. The socket 202 further includes an internal cavity 210 formed in the hammer connection end 203 and defined by an outer cylindrical wall 212 and a distal end wall 214, best seen in FIGS. 19 and 20. A channel 216 is formed in the end wall 214 so that, as the insertion tool connector 190 advances through the keyhole opening 204 and into the cavity 210, the shank 194 advances through the channel 216.

Figure 15:
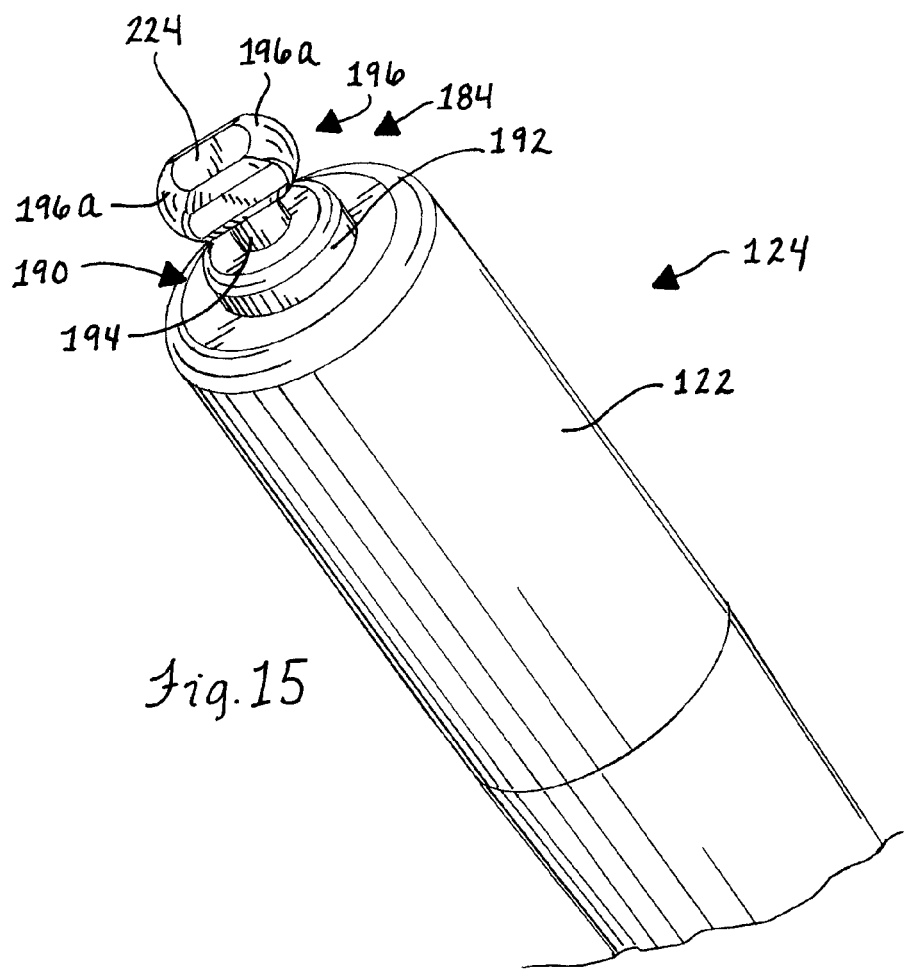
FIG. 15 is a perspective view of the connection end of the insertion tool of FIG. 10 showing a connector having a head and a shank for securing with a hammer instrument.

As can be seen in FIG. 15, the head 196 is enlarged relative to the shank 194. More specifically, the head 196 is somewhat elongate so that it has longitudinal ends 196a having a major dimension and side portions 196b having a smaller, minor dimension. During insertion of the head 196 into the hammer socket 202, the longitudinal ends 196a are aligned with the channel 216. Once the head 196 is received fully into the cavity 210, the respective connection ends 184 and 203 are rotated relative to each other. This shifts the longitudinal ends 196a to a position where they are somewhat captured by the end wall 214.

Preferably, the cavity 210, shank 194, and head 196 are sized so that, when the longitudinal ends 196a are captured by the end wall 214, the hammer instrument 200 and the connector 190 are relatively secured with each other. More specifically, it is preferred that a bottom surface 220 of the head 196 (FIG. 14) is positioned from the base 192 a distance equal to the thickness of the end wall 214 of the hammer instrument 200. The cavity 210 is further defined by an interior top wall 222, and a top surface 224 of the head 196 is positioned thereagainst. These features generally inhibit pivoting of the hammer instrument 200 relative to the insertion tool 120. Additionally, the major dimension of the longitudinal ends 196a of the head 196 may be sized to abut the outer wall 212 of the cavity 210 to frictionally inhibit rotation of the hammer instrument 200 and the insertion tool 120.

The force received from the hammer instrument 200 coupled with the connector 190 is transmitted from the hammer instrument 200 to the base 192, which in turn transmits the force to the shank 194. The shank 194 extends into the grip portion 122 and is secured with the rigid handle body portion 182 so that the force is eventually transmitted through to the insertion tool 120.

The hammer instrument 200 allows a surgeon to direct a desired amount of force in a controlled manner to the insertion tool 120. To do so, the hammer instrument 200 includes a mass in the form of a hammer member 230 slidably located on a shaft 232. The shaft 232 extends between and is secured with a driving anvil surface 234 on the hammer connection end 203 and a withdrawal anvil surface 236 formed on rear anvil 238. To provide driving force, the hammer member 230 may be drawn away from the driving anvil surface 234 and then directed into the driving anvil surface 234, either by gravity or by manual acceleration. The hammer member 230 slides along the shaft 232 and strikes the driving anvil surface 234, thereby imparting an impulse or impact force to the connection end 203, the force then being transmitted through the insertion tool 120, as has been described. This allows a controlled tapping of the insertion tool 120 and the VBR 10 into the intervertebral space, as opposed to a manually provided force which, once standing friction is overcome, may be excessive and may cause damage to portions of the spine. If an amount of withdrawal is desired, the hammer member 230 may be directed into the withdrawal anvil surface 236 formed on the rear anvil 238.

Once the surgeon believes the VBR 10 is in a suitable position within the intervertebral space, the insertion tool 120 may be disconnected and withdrawn. Utilizing the radiographic markers 90, a determination can be made as to whether adjustments to the position of the VBR 10 are necessary or desirable. If only slight adjustments are desired, a VBR tamp device 250, shown in FIGS. 21 and 22, may be used. Furthermore, the VBR tamp device 250 may be used if packing of graft material into the intervertebral space inadvertently shifts the VBR 10 from the desired position.

The VBR tamp device 250 has a handle portion 252 for holding and manipulating the device 250. The handle portion 252 may be constructed similarly to the handle portion 124 of the insertion tool 120 so that it has an outer grip portion 254 and an inner body portion (not shown) that is generally rigid and secured with a proximal connector end 256 and with an elongate shaft 258 having a distally located engagement end 260. The connector end 256 has a connector 262 including an enlarged head 264, base 266, and shank 268 and is substantially identical to the connector end 184 of the insertion device 120 as has been described above. The connector end 256 may be coupled or secured with the hammer instrument 200, as has also been described above.

The distal engagement end 260 is received in the VBR socket 100, though in a different manner than the insertion device 120. For the VBR tamp device 250, a single curved arm 270, substantially identical to the curved arm 150 of the insertion tool 120, extends from the elongate shaft 258 for being received in the socket recess 102. Furthermore, a non-threaded pin 272 extends from the engagement end 260 in the longitudinal direction. The pin 272 is merely inserted into the threaded socket bore 112, and may be loosely received therein. This construction allows the engagement end 260 to be quickly and easily inserted and removed from the VBR socket 100.

Further forms of tamp devices are depicted in FIGS. 23-27. Specifically, FIGS. 23 and 24 illustrate a form of a tamp device 300 having an L-shaped head 302, and FIGS. 25 and 25 illustrate a tamp device 340 have a blunt blade head 342. Each of the tamp devices 300, 340 includes respective handle portions 304, 344 secured with and extending between respective connection ends 306, 346 and elongate shafts 307, 347 having distally positioned tamp ends 308, 348, which respectively include the L-shaped head 302 and the blunt blade head 342. The handle portions 304, 344 may include outer grip portions 310, 350, and rigid inner portions (not shown), these features having been described above. The tamp devices 300, 302 may be used manually, or may be secured or coupled with the hammer instrument 200, for instance, to adjust the graft material, as well as to adjust the position of the VBR 10, as a surgeon desires.

A trial spacer device 360 is illustrated in FIGS. 27 and 28 for determining a proper or desired size VBR 10. A series of trial spacer devices 360 may be provided, which correspond to a series of sizes for the VBR 10. The trial spacer device 360 includes a connector end 362 substantially identical to the connector end 184 of the insertion tool 120 for coupling with the hammer instrument 200, for instance. The connector end 362 is rigidly secured with a handle portion 364, which preferably has an outer grip portion 366 and an inner rigid body portion (not shown), as has been described above. Extending from the handle portion 364 is an elongate shaft portion 370 having a distally located trial spacer portion 372. As can be seen, the trial spacer portion 372 has a geometry and shape corresponding to the VBR 10, though the trial spacer portion 372 has the teeth 16 omitted so that it may be more easily inserted into and removed from the intervertebral space.

A surgeon may utilize one or more trial spacer devices 360, with trial spacer portions 372 corresponding to various sizes of VBRs 10. Because the actual VBR 10 includes the gripping surfaces 12, 14, insertion and removal of several different sizes of the VBR 10 may cause significant damage to the vertebral surfaces. Once the intervertebral space has been prepared, the surgeon selects a first trial spacer device 360 with a particular size trial spacer portion 372 and attempts to insert the trial spacer portion 372 in the intervertebral space. If successful, the surgeon then determines whether the trial spacer portion 372 provides the desired fit within the intervertebral space. In other words, the trial spacer devices 360 are used in a trial-and-error method to select the best fit for the intervertebral space of the specific patient. The trial spacer devices 360 may be color-coded with the VBRs 10 so that identification of the proper VBR 10 based on the determination of a best-fit trial spacer device 360 is facilitated.

Turning now to FIGS. 29-35, a further implant device in the form of a spinal fusion vertebral replacement body (VBR) 400 is illustrated for implantation within an intervertebral space between adjacent vertebrae. Like the VBR 10, the VBR 400 has a generally curved, concavo-convex shape along a longitudinal axis 402 of the VBR.

In one form, the longitudinal axis 402 of the implanted VBR 400 may extend laterally, or perpendicular to the anterior-posterior axis of the patient's spine. The VBR 400 has a shape similar to a natural spinal disc and extends across a large area of the vertebral surfaces for providing support to the vertebral column and spine. As a result, a single VBR 400 may be used for fusion surgery between adjacent vertebrae. In contrast to the VBR 10, the VBR 400 is generally solid and does not include any internal cavities or throughbores for bone ingrowth therein. In another form, discussed below, a pair of VBRs 400 may be implanted in the intervertebral space, in which case, the longitudinal axes 402 of the VBRs 400 extend along the anterior-posterior axis of the patient's spine or at an angle relative thereto.

Figure 30:
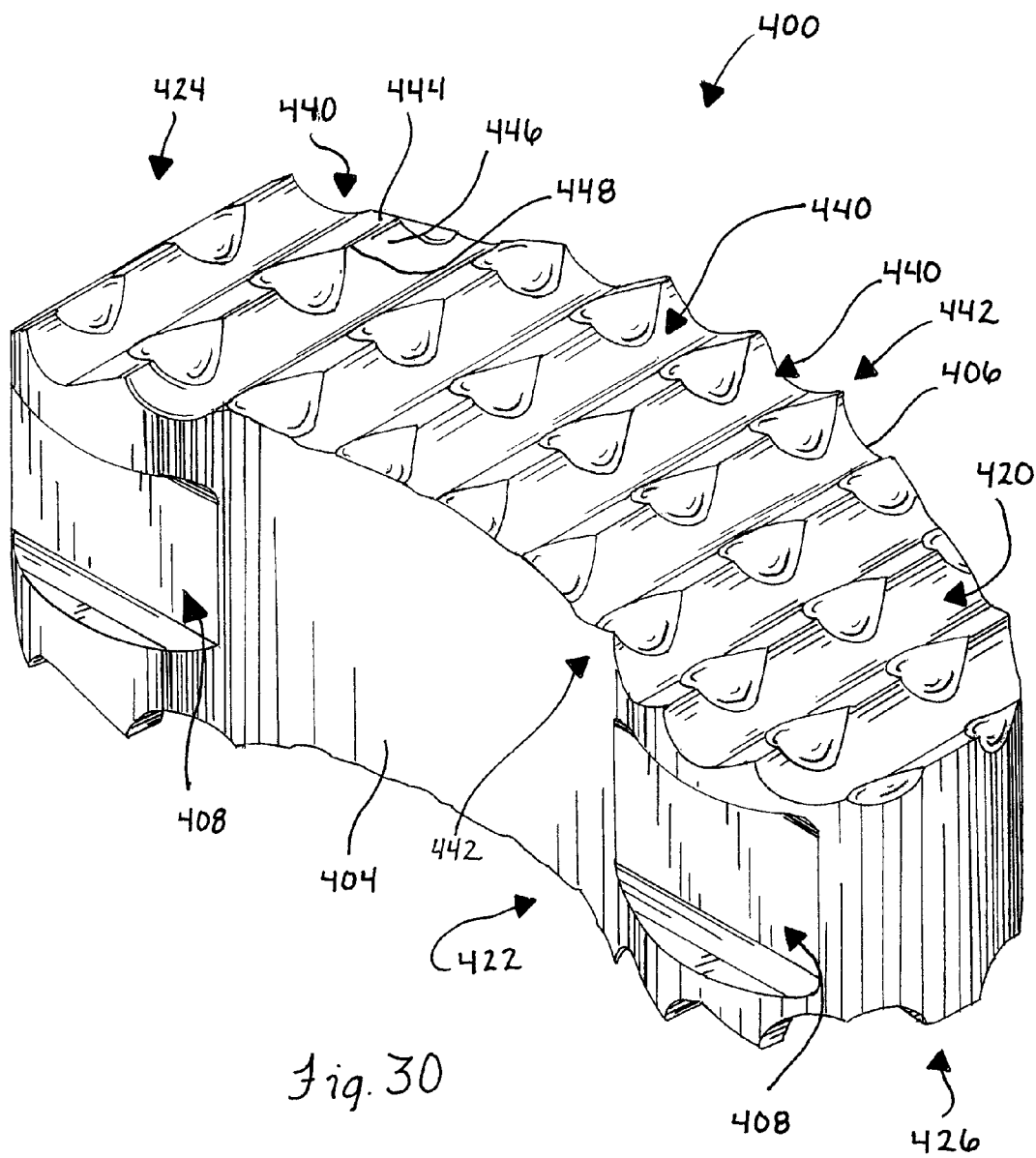
FIGS. 30 and 31 are perspective views of the VBR device of FIG. 29 showing a trailing end and channels formed on the lateral sides and extending to the trailing end for receiving an insertion tool.
Figure 31:
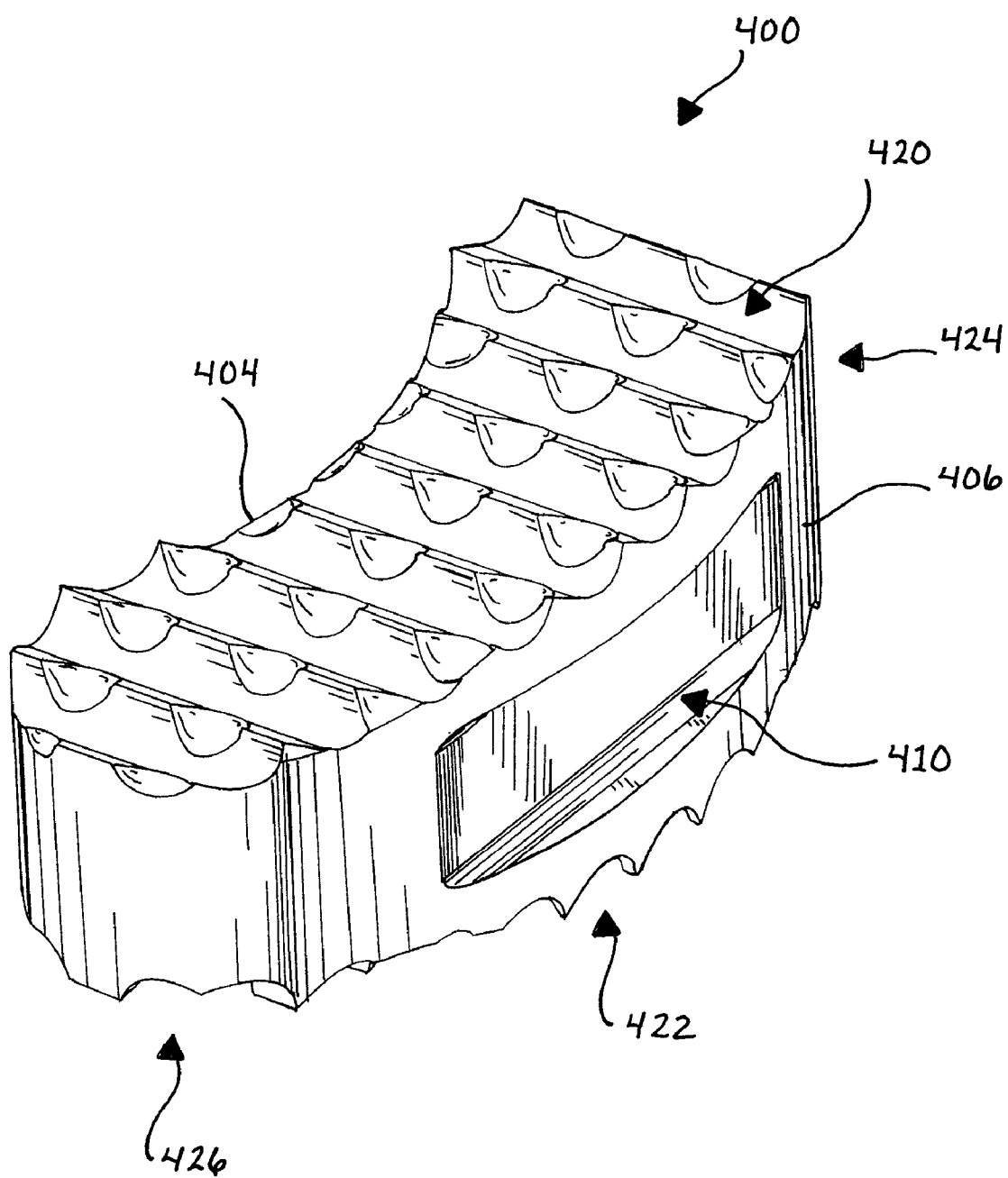
Figure 34:
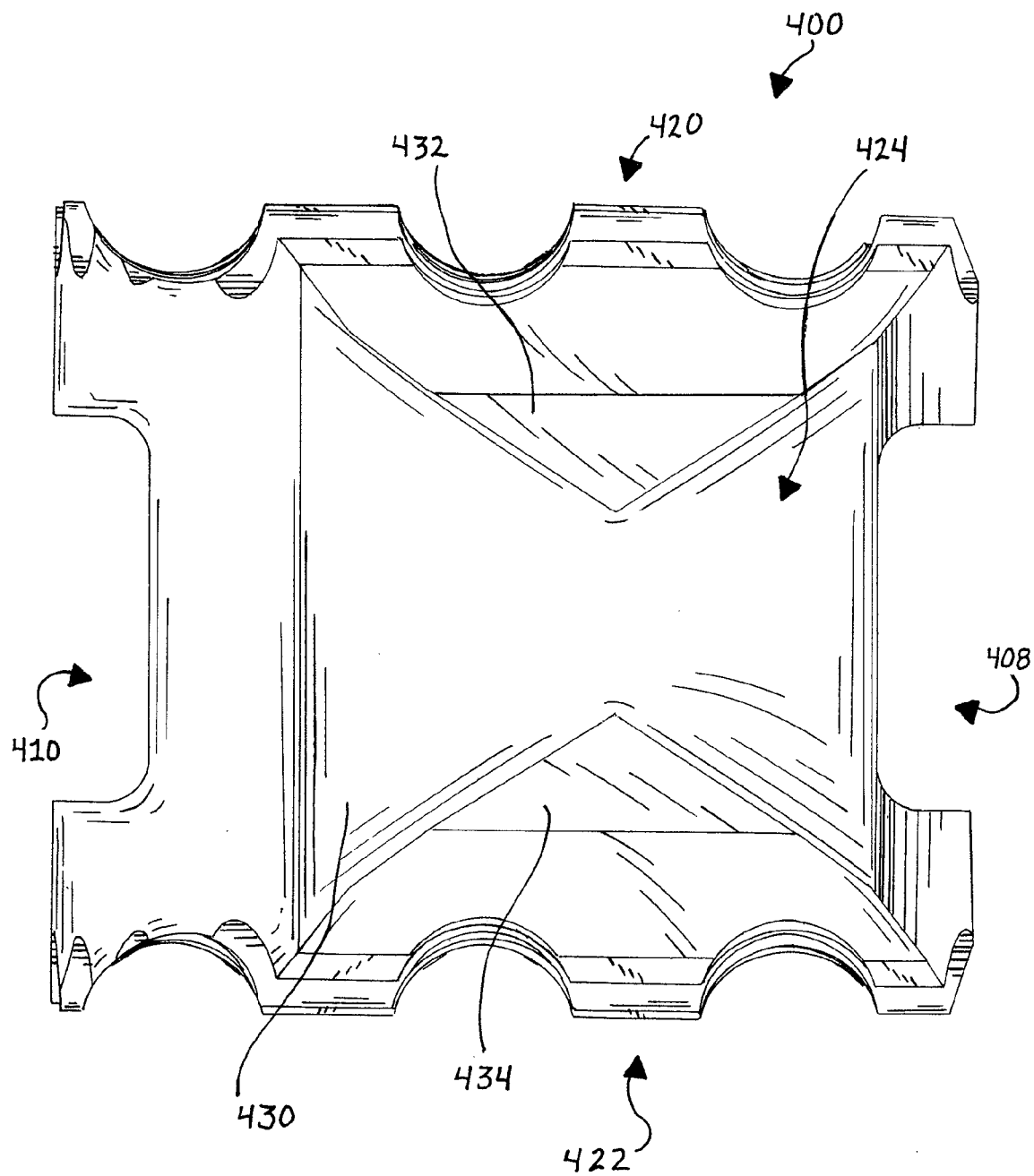
FIG. 34 is a side elevation view of the insertion end of the VBR device of FIG. 29 taken along the line 34-34 of FIG. 33.
Figure 35:
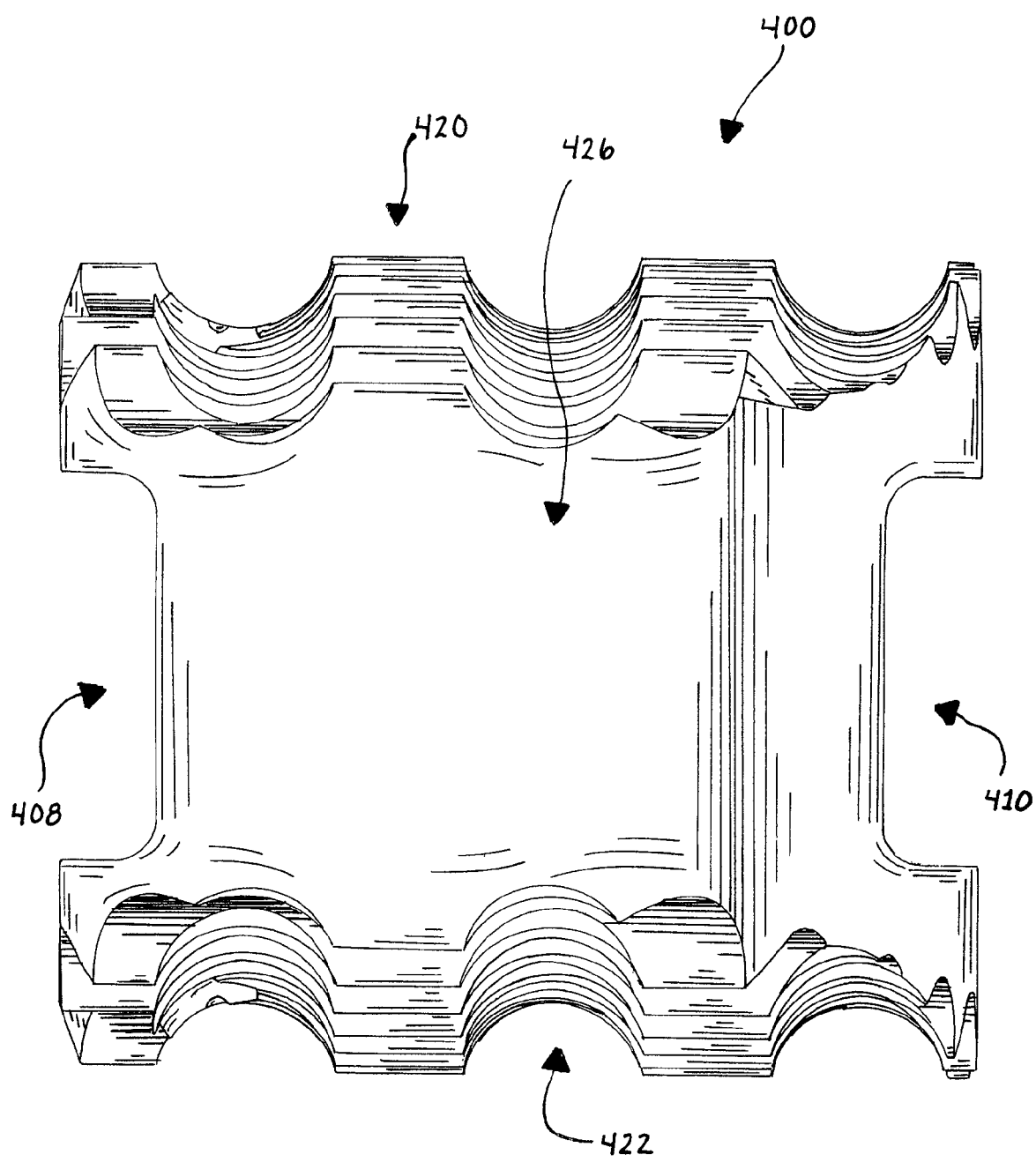
FIG. 35 is a side elevation view of the trailing end of the VBR device of FIG. 29 taken along the line 35-35 of FIG. 33.
Figure 63:
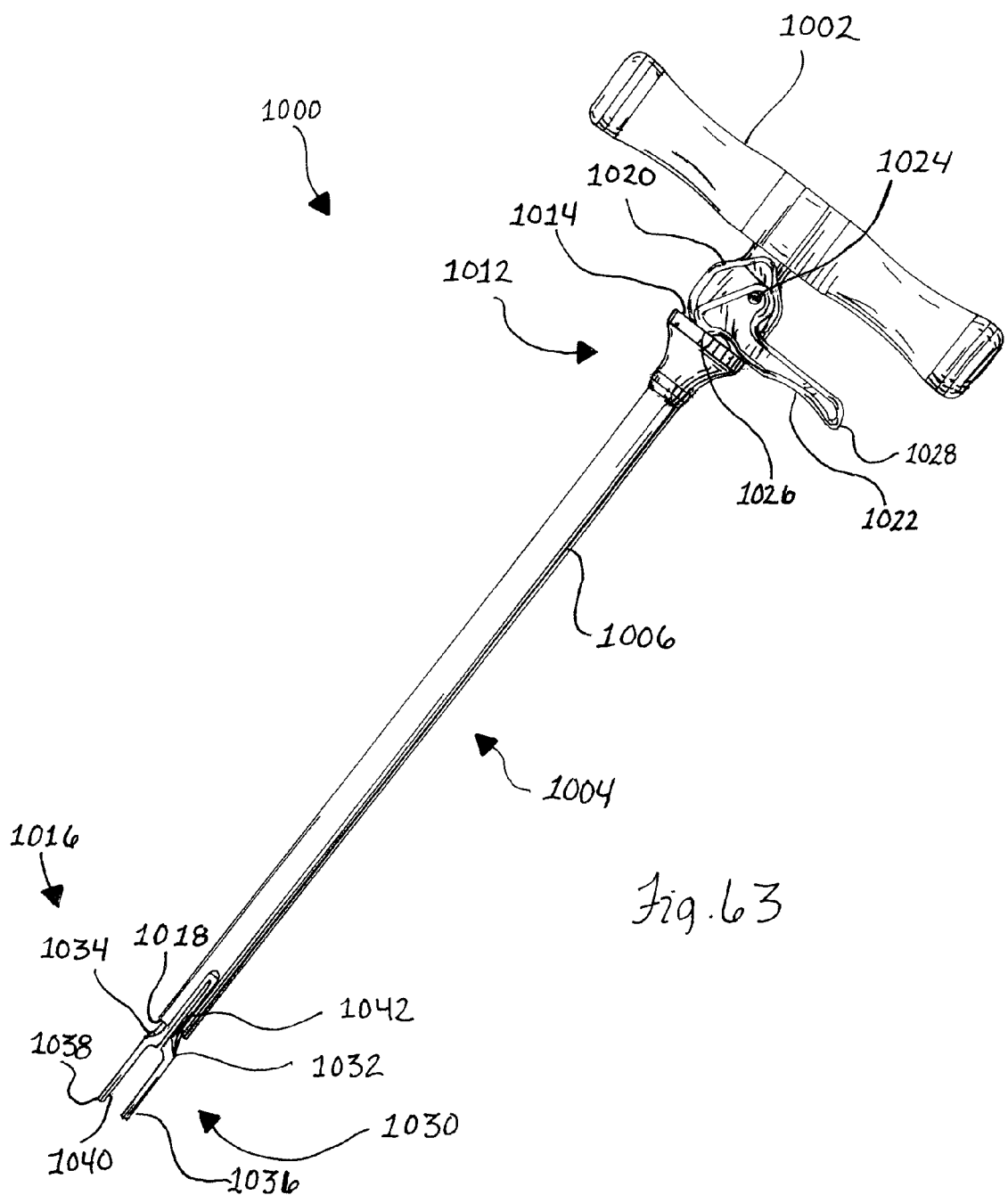
FIG. 63 is a perspective view of an insertion tool for implanting any of the VBR devices shown in FIGS. 29, 36, 44, 51, 55, and 68.
Figure 64:
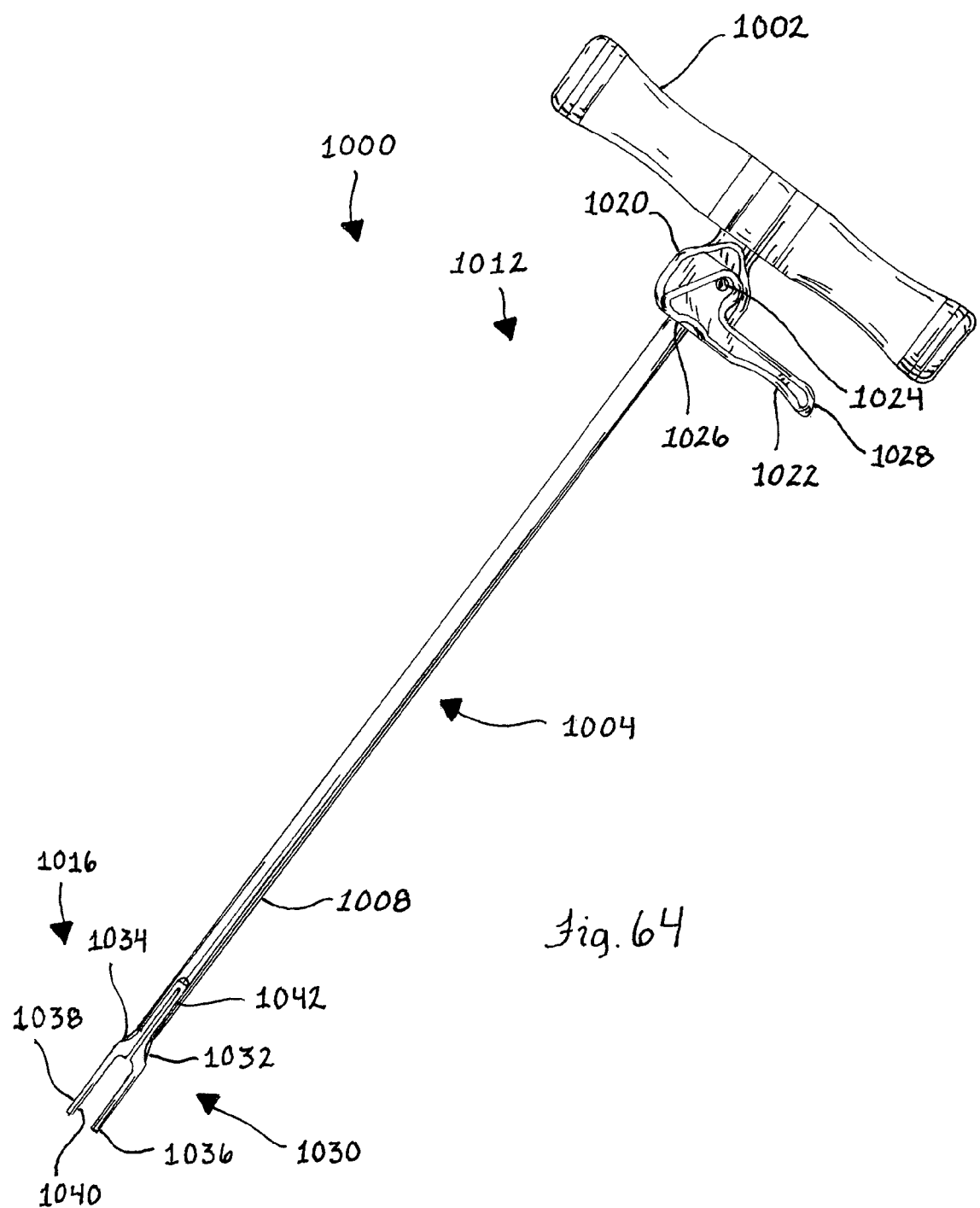
FIG. 64 is a perspective view of the insertion tool of FIG. 64 shown with the outer shaft removed.

With specific reference to FIGS. 30 and 31, the VBR 400 includes surface structure for being grasped and manipulated by an inserter device (such as, for example, the insertion tool 1000 shown in FIGS. 63 and 64). The inserter device may include a pair of linear or straight arms or prongs that engage the lateral side surfaces of the VBR 400. More specifically, the VBR 400 includes a concave side 404 and a convex side 406. The concave side 404 has a pair of channels 408 that are aligned with and parallel to the longitudinal axis 402 for receiving a first linear inserter arm. The convex side 406 includes a single channel 410 for receiving a second of the linear inserter arms. The arms grasp the VBR 400 via these channels 408, 410. The channels 408, 410 are approximately rectangular in shape, as can be seen in FIG. 34, and the arms are closely mated within the channels so that the movement of the inserter device results in a similar motion by the VBR 400. It should be noted that the trailing end 426 may include a receptacle or socket (not shown) for receiving a portion of the inserter device therein. For instance, a threaded socket may be provided and the inserter device may have a threaded portion received by the socket to retain the VBR 400 on the inserter device.

Figure 32:
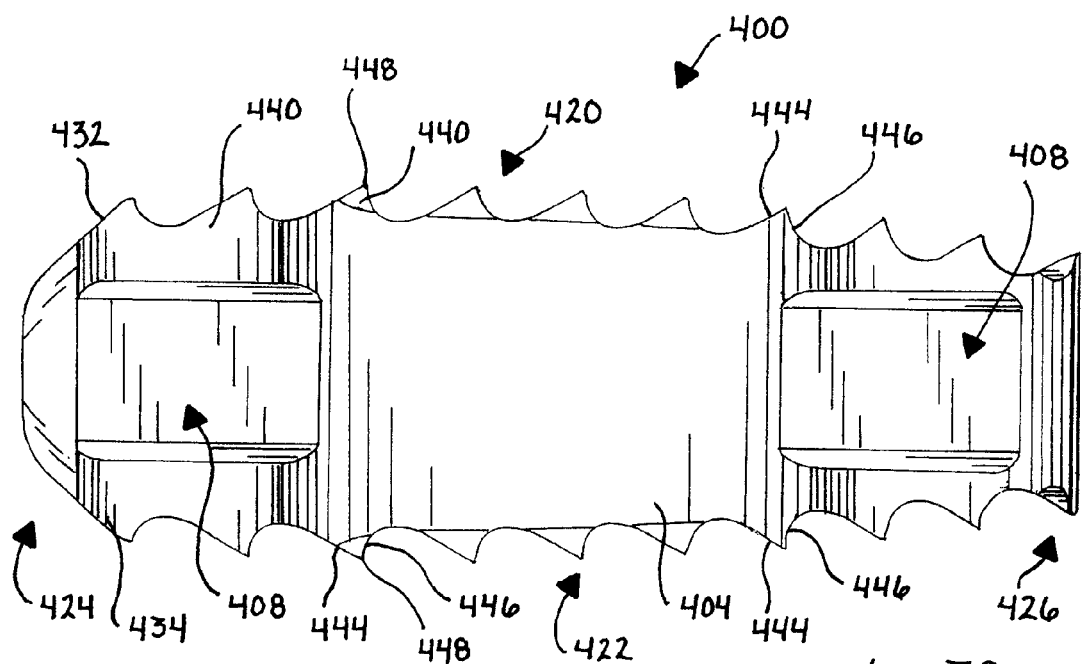
FIGS. 32 and 33 are side elevation views of the VBR device of FIG. 29 showing the channels, an insertion end having upper and lower slanted surfaces for promoting insertion within the intervertebral space, and gripping members on the upper and lower gripping surfaces, the gripping surfaces being arcuate to follow a curve of the endplates of the adjacent vertebrae.
Figure 33:
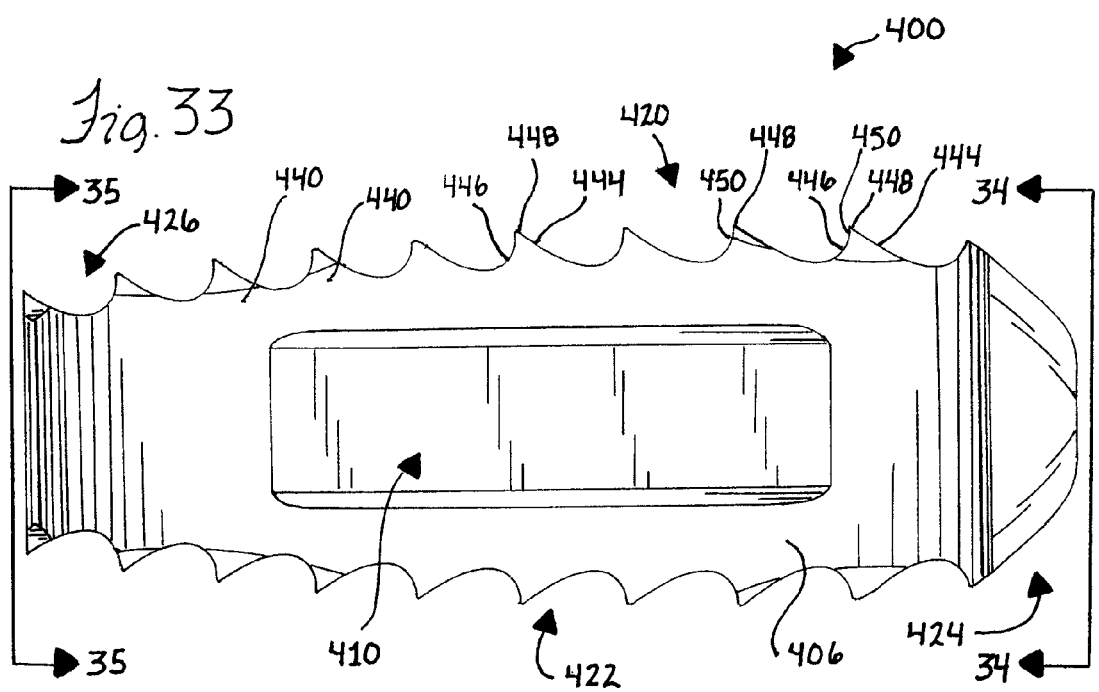

The VBR 400 has upper and lower gripping surfaces 420 and 422 for engaging with the vertebral surfaces. With reference to FIGS. 32 and 33, the VBR 400 has an insertion end 424 and a trailing end 426. In a form extending generally laterally within the intervertebral space, the upper and lower gripping surfaces 404, 406 are generally planar, like the upper and lower gripping surfaces 12 and 14 of the VBR 10. In the illustrated embodiment, the VBR 400 has a larger vertical dimension proximate the insertion end 424 than proximate the trailing end 426. This is desirable in the case where a vertebra is damaged and a portion thereof is removed.

Additionally, a pair of the VBRs 400 may be implanted in a single intervertebral space so that the VBRs 400 extend generally along the anterior-posterior axis of the patient's spine such that the trailing end 426 is in a rear lateral position and VBR curves around toward the middle of the intervertebral space. A space is thereby provided for packing bone graft material therebetween. The intervertebral space may be prepared prior to implantation so that the contour of the vertebral surfaces generally matches that of the gripping surfaces 420, 422 to improve purchase by the gripping surfaces 420, 422 and to reduce the likelihood of subsidence, as discussed above. The paired VBRs are oriented within the intervertebral space so that the concave sides 404 of each VBR 400 are oriented towards each other. The concave sides 404 impede explantation of the graft material therefrom and provide constraint towards the insertion end 424 for packing of the graft material therebetween. The pair of VBRs are implanted in a somewhat U-shape that allows easy access for packing of the graft material therebetween.

Figure 29:
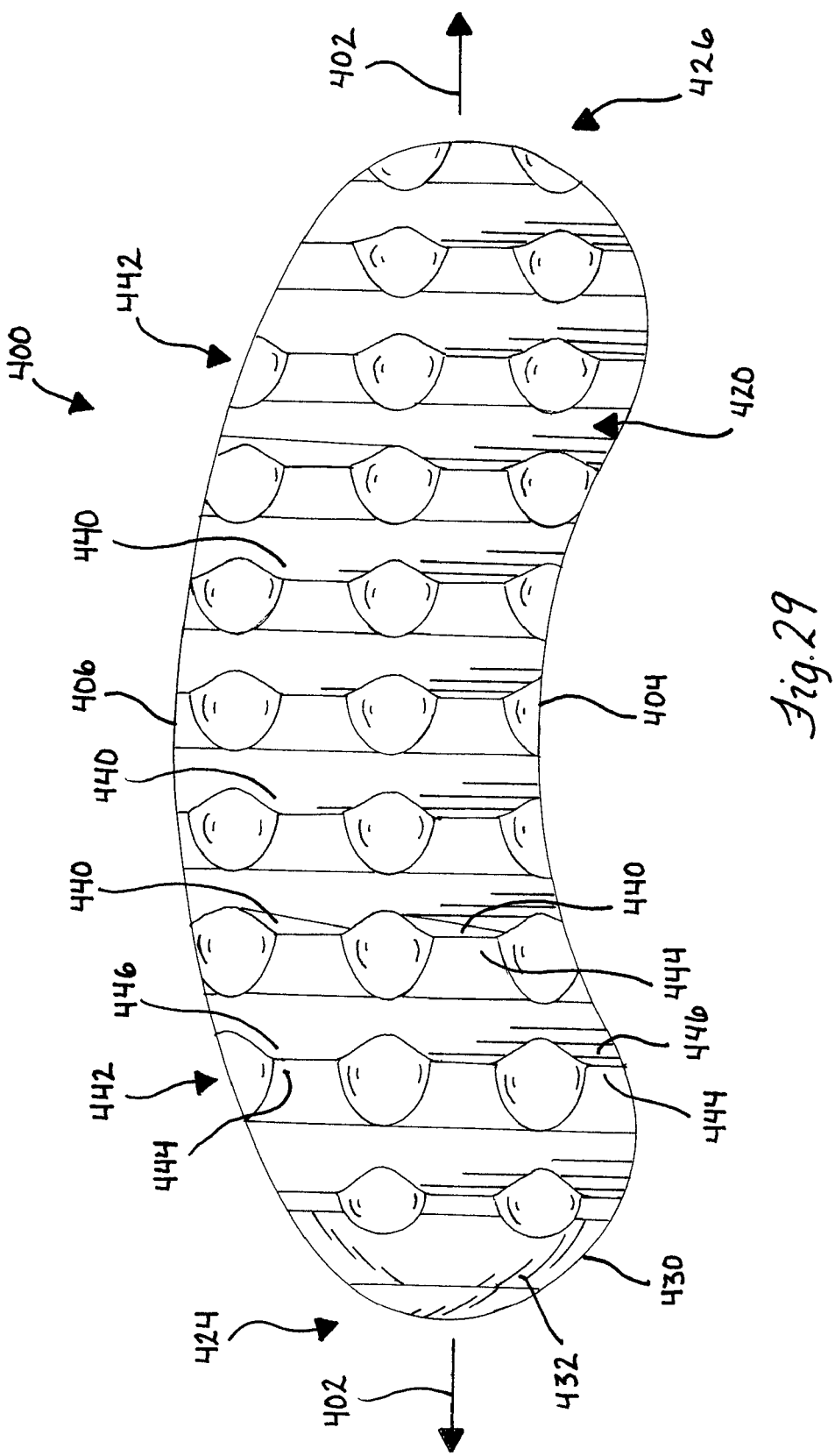
FIG. 29 is a plan view of an alternative form of a VBR device having gripping members aligned in rows generally transverse to a longitudinal axis of the VBR device, a generally solid body, and a curved shape similar to the shape of the VBR device of FIG. 1.

The insertion end 424 is shaped to facilitate the insertion of the VBR 400 in the intervertebral space. As can be seen in FIG. 29, the insertion end 424 includes a generally vertical rounded surface 430. Additionally, the top gripping surface 420 has a downward slanted portion 432 proximate the insertion end 424 while the bottom gripping surface 422 has an upward slanted portion 434 proximate the insertion end 424. In combination, the rounded surface 430 and the slanted portions 432, 434 assist insertion and implantation of the VBR 400 by allowing the VBR 400 to be wedged into the intervertebral space.

The gripping surfaces 420, 422 of the VBR 400 have gripping members for embedding and securing with the vertebral surfaces. More specifically, the gripping surfaces 420, 422 include a plurality of teeth 440 arrayed in rows 442 (FIG. 29) oriented generally perpendicular to the longitudinal axis 402 of the VBR 400.

In the illustrated form, the teeth 440 are uni-directional so that they resist explantation of the VBR 400. Specifically, each tooth 440 has a leading surface 444 facing the direction of insertion of the VBR 400, and a trailing surface 446 opposite the leading surface 444. The tooth surfaces 444, 446 extend from the gripping surfaces 420, 422 to meet at a peak 448 forming a line. As can be seen in FIGS. 32 and 33, the trailing surface 446 extends at a steeper angle than the leading surface 444 does. More precisely, the trailing surface 446 curves outward from the gripping surfaces 420, 422 such that a terminal portion 450 located proximate to the peak 448 is approximately orthogonal to the gripping surfaces 420, 422. In contrast, the leading surface 444 is generally flat with a relatively shallow angle relative to the gripping surfaces 420, 422. This configuration for the teeth 440 allows the leading surface 444 to act as a wedge to assist with insertion of the VBR 400, while the trailing surface 446 acts as a barb to impede movement of the VBR 400 in a direction opposite the insertion direction.

Like the VBR 10, implantation of the VBR 400 may be preceded by use of the trial spacer device 360. In addition, once the VBR 400 is located in the intervertebral space, tamp devices such as those discussed above may be used for packing bone graft material in the intervertebral space or for adjusting the position of the VBR 400.

Referring now to FIGS. 36-43, another form of an implant device in the form of a vertebral body replacement (VBR) 500 is illustrated. The VBR 500 is directed into the intervertebral space in a first, insertion orientation and is then rotated to a second, implantation orientation once in a selected position. Additionally, the VBRs 500 are preferably implanted as an opposed pair to define a region therebetween for receiving bone graft material. Like the VBR 400, the VBR 500 is generally solid and free of cavities or throughbores for permitting bone ingrowth therein.

The VBR 500 has an insertion end 502 and a trailing end 504 oriented along a longitudinal axis 506. The VBR 500 has upper and lower gripping surfaces 510, 512 for engaging and embedding with the superior and inferior vertebral surfaces. The VBR 500 further has an inner side surface 520 and an outer side surface 522, each of which is described in greater detail below. In the insertion orientation, the VBR 500 is oriented so that, upon initial insertion, the side surfaces 520, 522 are facing the vertebral surfaces and slide thereagainst. Thus, the gripping surfaces 510, 512 are initially positioned on the sides of the VBR and generally do not engage the vertebral surfaces. Once located generally in a desired position within the intervertebral space, the VBR 500 is rotated so that gripping surfaces 510, 512 engage with and embed into the vertebral surfaces. As the VBR 500 is used in pairs, the desired position of each VBR 500 within the intervertebral space is to one lateral side of the vertebrae. When the pair of VBRs 500 is implanted, each is positioned with its longitudinal axis 506 generally oriented along the anterior-posterior axis of the patient's spine. When rotated, the outer side surface 522 of each VBR 500 generally faces outwardly toward the side of the intervertebral space, while the inner side surface 520 of each VBR 500 generally faces inwardly toward the center of the intervertebral space.

Figure 37:
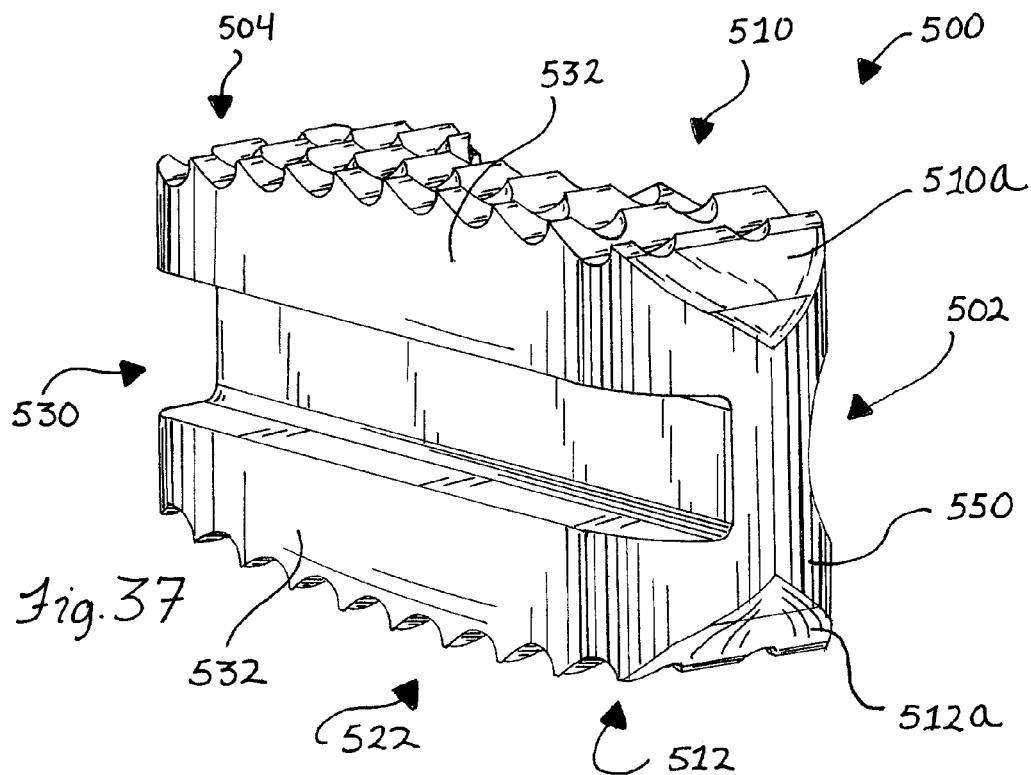
FIGS. 37 and 38 are perspective views of the VBR device of FIG. 36 showing the insertion end and lateral side surfaces having channels extending therealong and to the insertion end for engaging with an insertion tool and for receiving bone graft therein.

In greater detail, the outer side surface 522 is generally flat. As can be seen in FIG. 37, for instance, the outer side surface 522 includes a recessed channel 530 for receiving a portion of an inserter device (such as, for example, the insertion tool 1000 shown in FIGS. 63 and 64). Preferably, the inserter device and the channel 530 are closely sized and shaped so that the VBR 500 is tightly and rigidly held by the inserter device. The channel 530 is flanked by upper and lower generally flat surfaces 532 which slide along the vertebral surfaces during insertion.

Figure 38:
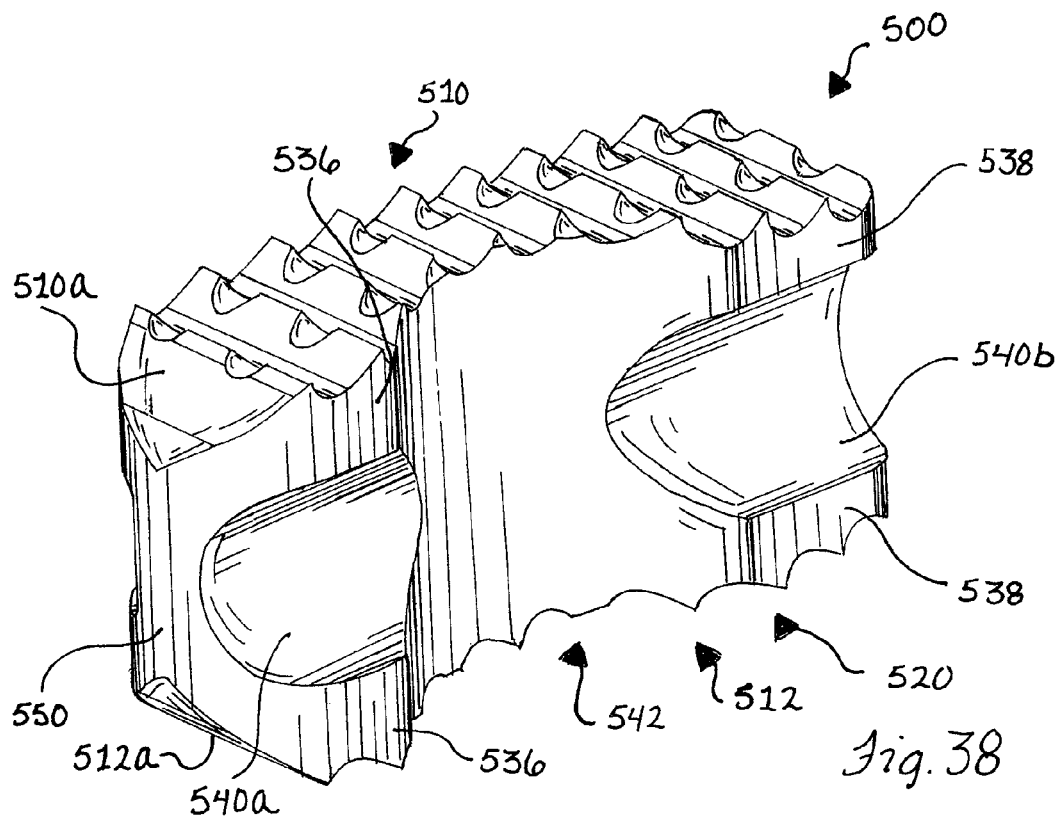

As can be seen in FIG. 38, the inner side surface 520 includes forward side surface portions 536 and rearward side surface portions 538 which are generally flat and, during insertion, slide against the vertebral surfaces. Extending parallel to the longitudinal axis 506 is a pair of recessed portions 540 for receiving a portion of the inserter device. A first recessed portion 540a is positioned near the insertion end between the forward side surface portions 536, and a second recessed portion 540b is located near the trailing end between the rearward side surface portions 538.

Each of the recessed portions 540 is preferably curved in shape and wider and deeper than the recessed channel 530, as can be seen in FIGS. 40 and 41. The shape of the recessed portions 540 allows the inserter portion engaged therewith to distribute forces over a greater area and more evenly. As a result, a wider selection of materials may be used for the VBR 500 than with other implant devices.

A common material for implant devices is a polymeric material known as PEEK. Beneficially, PEEK is a strong material. However, PEEK is not bio-resorbable. Available bio-resorbable materials tend to be brittle or at least not as strong as PEEK. Were a typical implant formed of a bio-resorbable material such as allograft or hydroxyapatite, the stress involved with rotation of the implant within the intervertebral space typically causes the implant to break.

It is believed that the principal reason the implants formed of a bio-resorbable material fail is because of concentrated stresses on the implant by the inserter device used for rotating the implant. By providing the recessed portions 540 with the curved shape and enlarging these relative to the overall size of the VBR 500, the stresses are significantly reduced. As a result, the VBR 500 may be formed of a bio-resorbable material which promotes bone ingrowth and fusion by transubstantiating into solid bone along with graft material packed between and around the pair of VBRs 500. Nonetheless, the VBR 500 may be made of any biocompatible material such as a polymer, metal, metal alloy, or other compatible material.

Figure 36:
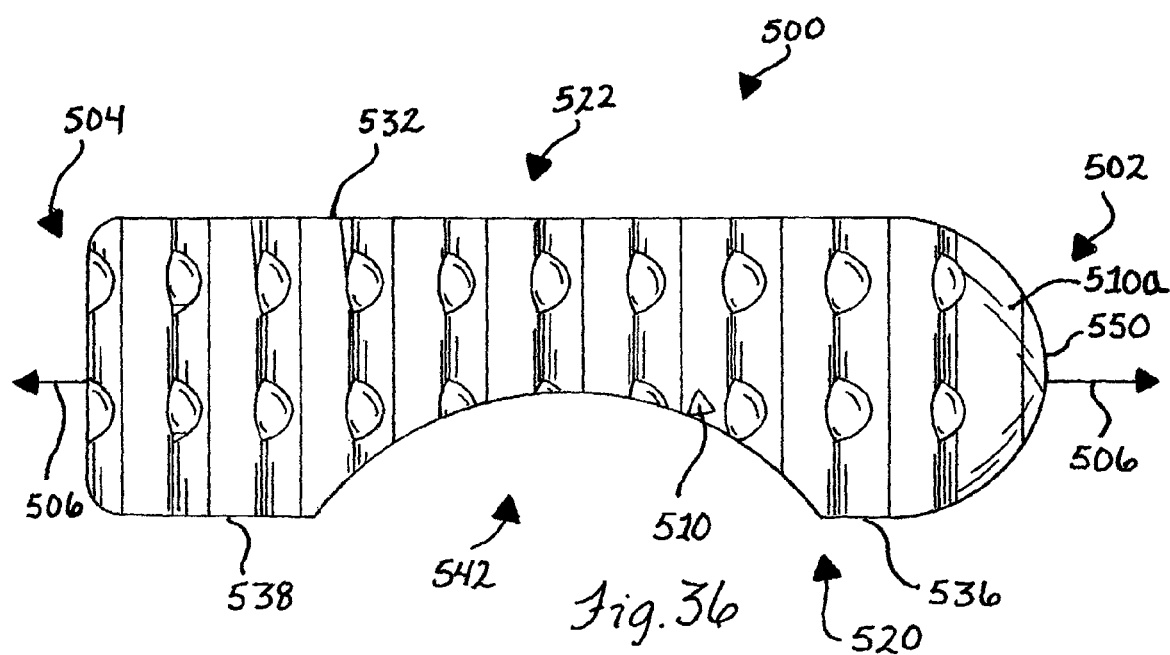
FIG. 36 is a plan view of a further form of a VBR device having a rounded insertion end, a generally flat trailing end, and an intermediate concave surface portion along one side to provide space for additional bone graft material to be packed within the intervertebral space.
Figure 39:
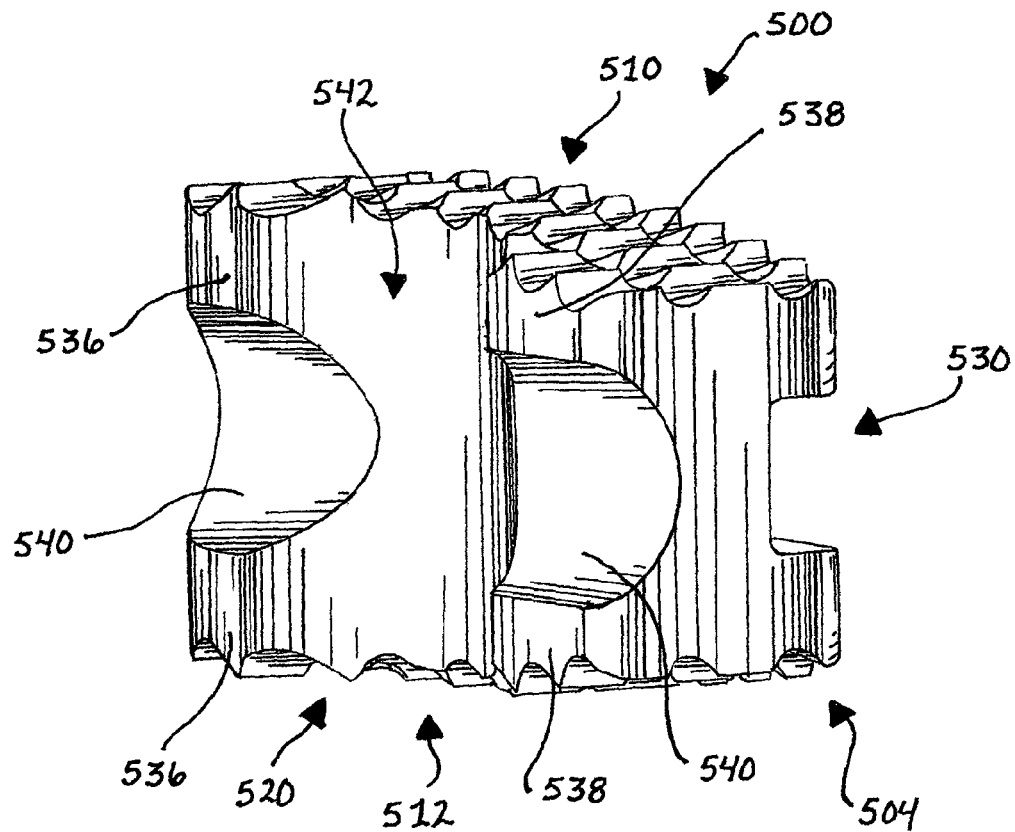
FIG. 39 is a perspective view of the VBR device of FIG. 36 showing the channels extending to the trailing end.

The inner side surface 520 provides a region for receiving bone graft material. The inner side surface 520 includes an intermediate concave surface portion 542, as can be seen in FIG. 36. When a pair of VBRs 500 are implanted in the intervertebral space, the inner side surfaces 520 of each VBR 500 are in facing relationship. The pair of implanted VBRs 500 define a region therebetween for receiving bone graft material. The concave surface portions 542 and the region between the VBRs 500 are packed with bone graft material to promote bone growth between the VBRs 500, as well as between and with the superior and inferior vertebrae. Thus, the concave surface portions 542 provide additional volume for receiving the bone graft material. As the implanted VBRs 500 are generally immobile, the concave surface portions 542 beneficially retain the graft material therebetween.

It should be noted that the previously discussed recessed portions 540, being concave and opening onto the inner side surfaces 520, also provide a region for packing and retaining bone graft material. Moreover, the recessed portions 540 provide access to the concave surface portion 542 so that graft material may easily be packed therein after the VBR 500 has been secured within the intervertebral space. In this manner, the concave surface portions 542 of an opposed pair of VBRs 500 impede explantation of the graft material and provide constraint for packing the graft material therebetween, while the recessed portions 540 allow the access to the concave surface portions 542 after implantation of the VBR 500. While securement of the VBR 500 in the intervertebral space substantially immobilizes the VBR 500 and the vertebrae, the bone ingrowth allows the adjacent vertebrae 14 to become a single, generally rigid structure with increased strength for supporting the spinal column 12 and the rest of the patient's body, such as their torso.

The insertion end 502 is shaped to facilitate insertion in a manner similar to that described above. As can be seen in FIG. 37, the insertion end 502 has a rounded generally vertical surface 550. Additionally, the gripping surfaces 510, 512 include respective slanted portions 510a and 512a which angle downward and upward respectively so that the insertion end 502 tapered inward. This shape for the insertion end 502 allows the VBR 500 to be wedged into the intervertebral space, as has been described above.

Turning now to FIGS. 42 and 43, the upper and lower gripping surfaces 510, 512 are contoured to closely match the concavity of the vertebral surfaces, as has been described above for VBR 400. Furthermore, the gripping surfaces 510 include gripping members, such as uni-direction teeth 560 substantially identical to the teeth 440 of the VBR 400, also described above.

Again, implantation of the VBR 500 may be preceded by use of one or more trial spacer devices (not shown) with a size and shape corresponding to various sizes of the VBR 500. Additionally, tamp devices may be utilized for packing bone graft material or adjusting the position of the VBR 500.

Another form of implant device in the form of a vertebral replacement body (VBR) 600 for spinal fusion surgery is illustrated in FIGS. 44-50. The VBR 600 is directed to the desired position in the intervertebral space in a first, insertion orientation and is then rotated to a second, implantation orientation. Additionally, in one form, a pair of VBRs 600 is implanted in the intervertebral space.

The VBR 600 includes a number of features described above with respect to the other VBRs. The VBR 600 has a body 626 with an insertion, end portion 602 and a trailing end portion 604 oriented along a longitudinal axis 606 that, when implanted, is generally oriented along the anterior-posterior axis of the patient or at an angle slightly offset therefrom.

The VBR 600 has upper and lower gripping surfaces 610, 612 for engaging and embedding with the adjacent superior and inferior vertebral surfaces. The gripping surfaces 610, 612 are contoured to closely match the concavity of the vertebral surfaces, as has been described above. In one form, illustrated in FIGS. 44-48, the gripping surfaces 610, 612 include rows of unidirectional teeth 660 substantially embodying the features of the uni-directional teeth described above. In another form, illustrated in FIGS. 49 and 50, for example, the upper and lower gripping surfaces 610, 612 include an alternative form of gripping members. Gripping members 661 also substantially embody the features of the uni-directional teeth described above, with the exception that the rows do not include depressions separating individual adjacent teeth. Both configurations of gripping surfaces 610, 612 advantageously minimize bone subsidence and maximize purchase by the teeth within the vertebral surfaces as described above.

Figure 45:
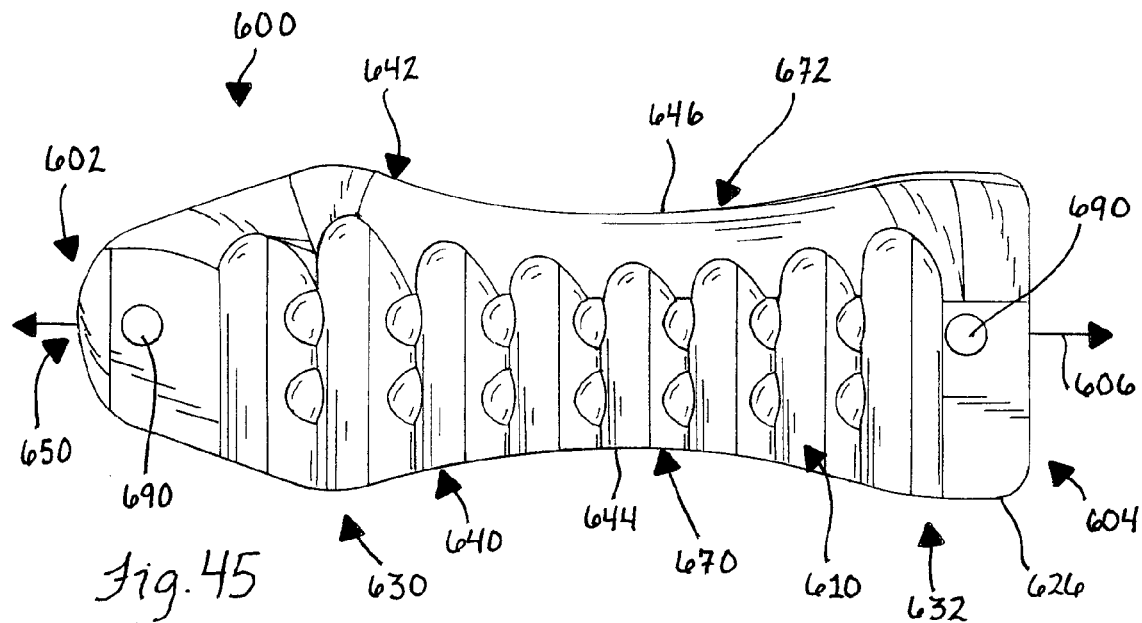
FIG. 45 is a plan view of the VBR device of FIG. 44.
Figure 47:
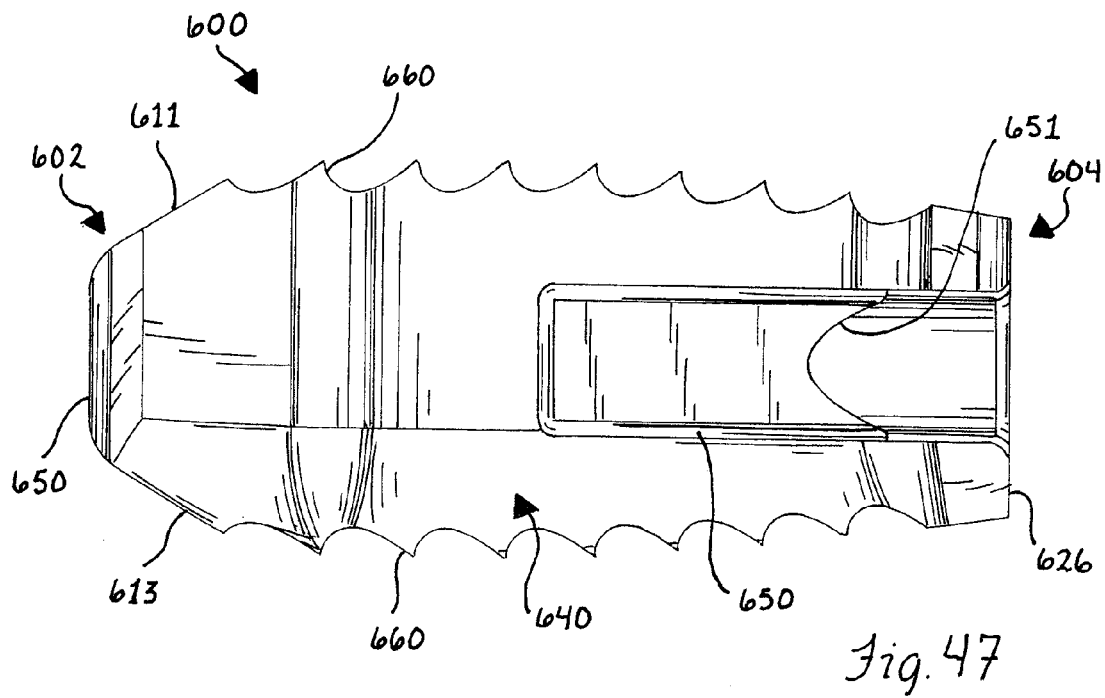
FIG. 47 is a side elevation view of the VBR device of FIG. 44 showing gripping members formed on the upper and lower surfaces of the VBR device, the upper and lower surfaces being arcuate to follow the contour of the vertebral endplates.
Figure 48:
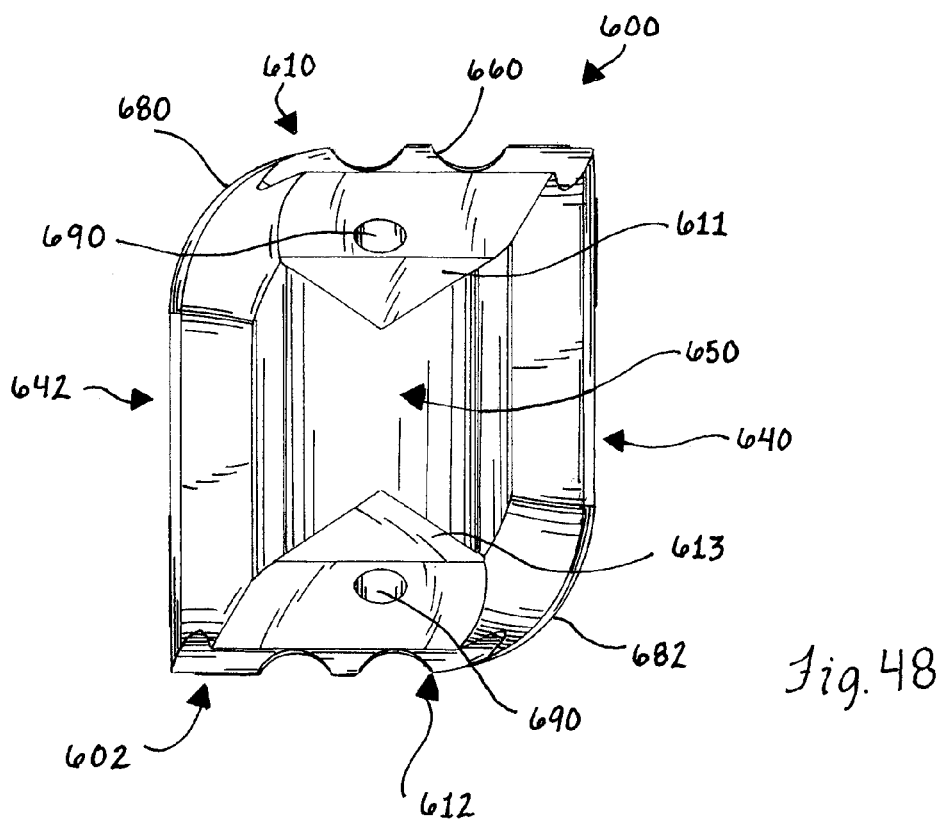
FIG. 48 is an end elevation view of the insertion end of the VBR device of FIG. 44.

The insertion end portion 602 is shaped to facilitate insertion in a manner similar to that described above. As can be seen in FIGS. 45 and 47, the insertion end has a rounded, generally vertical surface 650. Additionally, gripping surfaces 610, 612 include respective slanted portions 611 and 613 which angle downward and upward respectively so that the insertion end portion 602 is generally tapered inward. Again, the shape of insertion end portion 602 permits the VBR 600 to be wedged into the intervertebral space, as described above.

Figure 50:
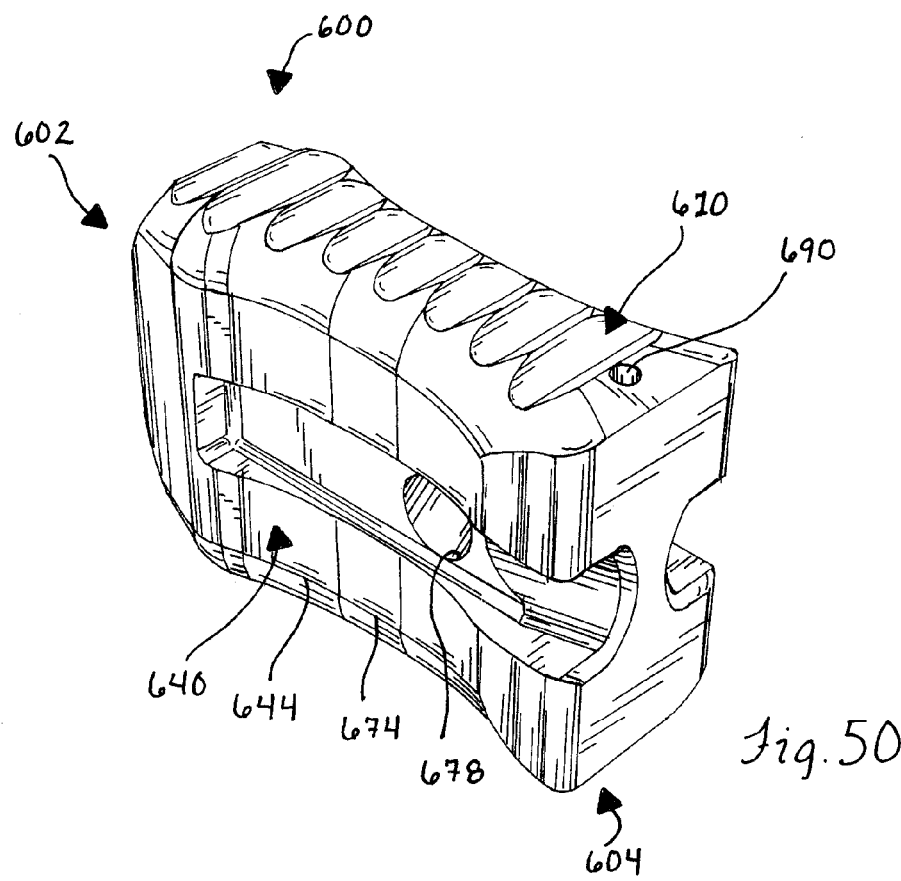
FIG. 50 is a perspective view of the VBR device of FIG. 49 showing a throughbore for receiving a hook or other tool to easily remove the VBR device from the intervertebral space.
Figure 53:
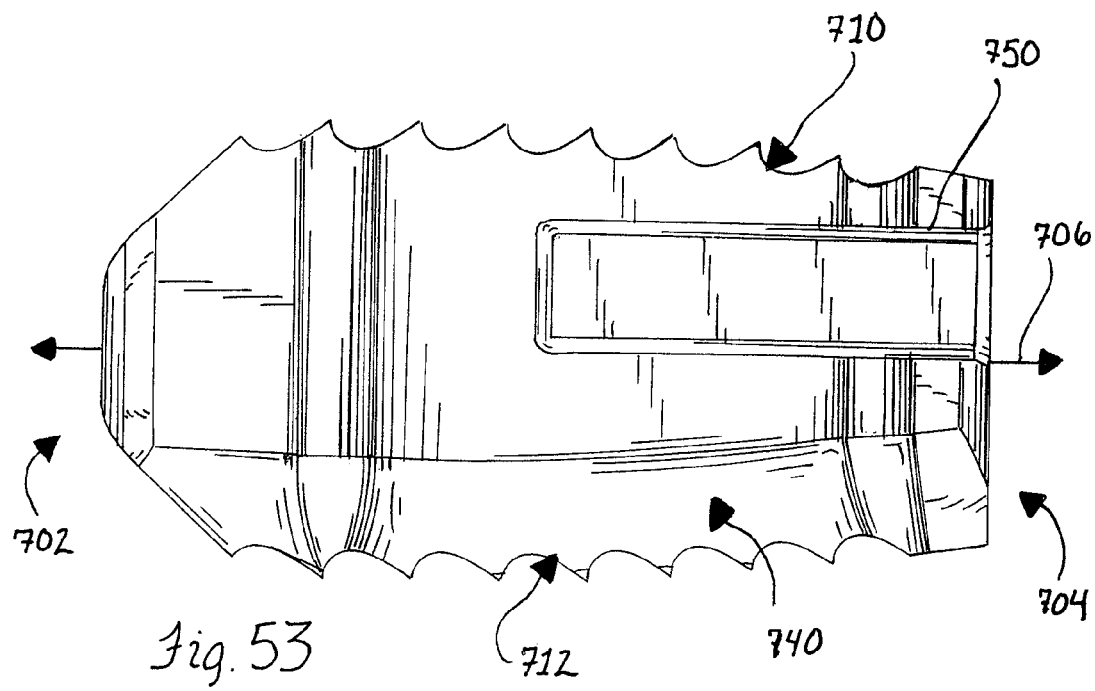
FIGS. 53 and 54 are side elevation views of the VBR device of FIG. 51.
Figure 54:
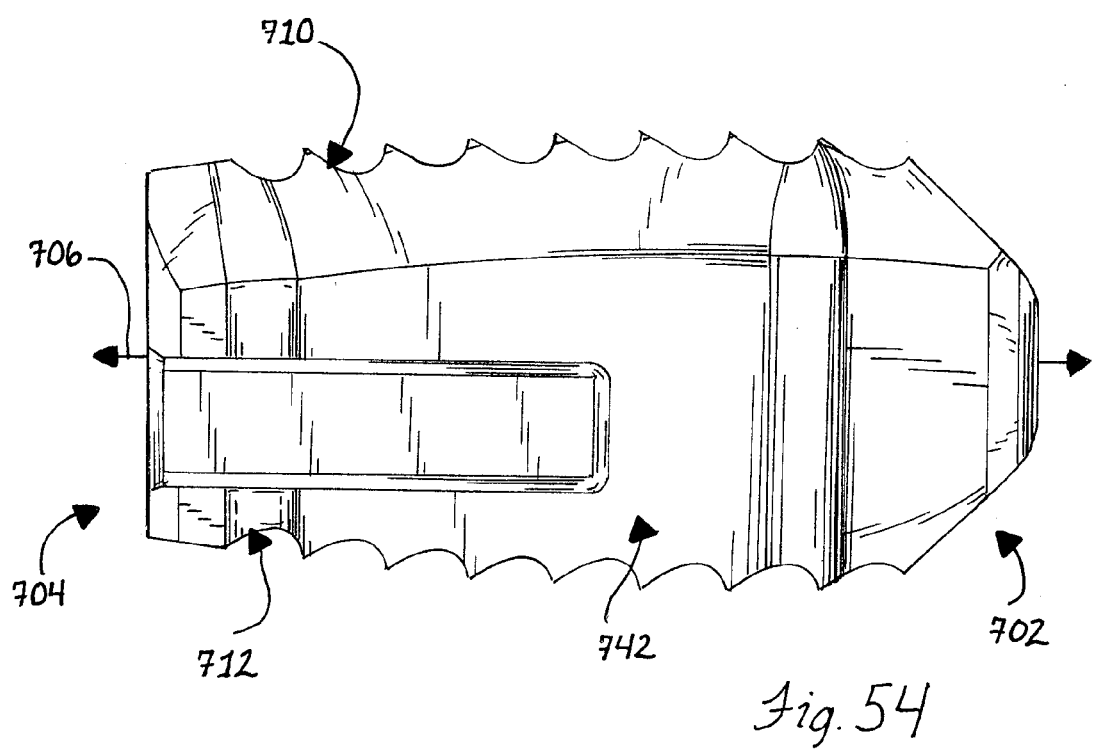

The VBR 600 is generally solid and free of cavities or throughbores for permitting bone growth therein. As shown in FIG. 50, the VBR 600 may optionally include a throughbore 678 for permitting the VBR 600 to be grabbed by a hook or other tool (not shown) to easily remove the VBR 600 from the intervertebral space if necessary. The VBR 600 may also include radiographic markers 690, as shown in FIG. 44, embedded in the body 626 to allow a surgeon to use radiographic equipment to identify the location and orientation of the VBR 600 within the intervertebral space.

Figure 44:
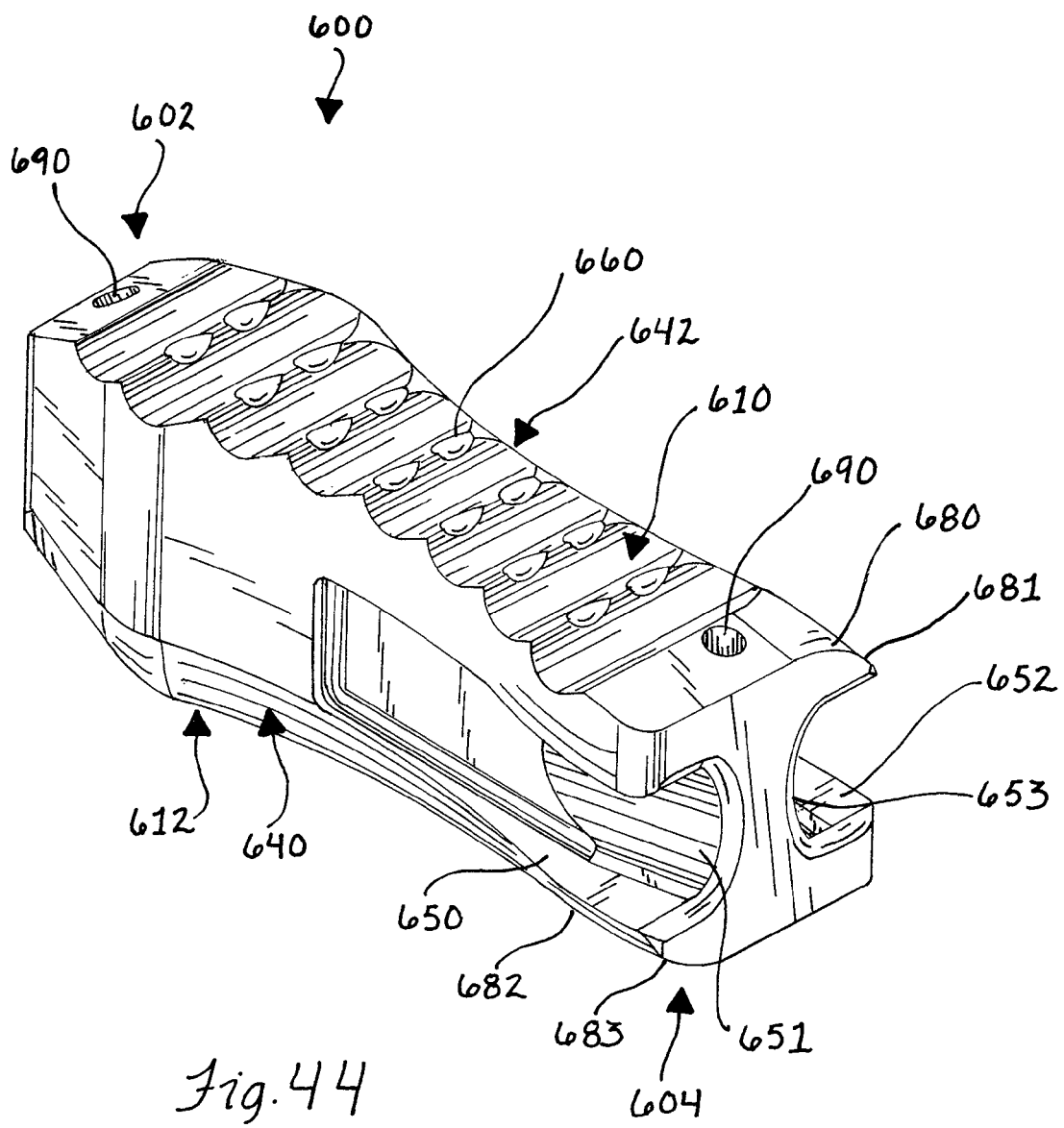
FIG. 44 is a perspective view of a further form of a VBR device having an implant body including diagonally-opposed, elongate curved corner portions and slots formed on the lateral side surfaces and extending to the trailing end for engaging an insertion tool and for receiving bone graft therein.
Figure 49:
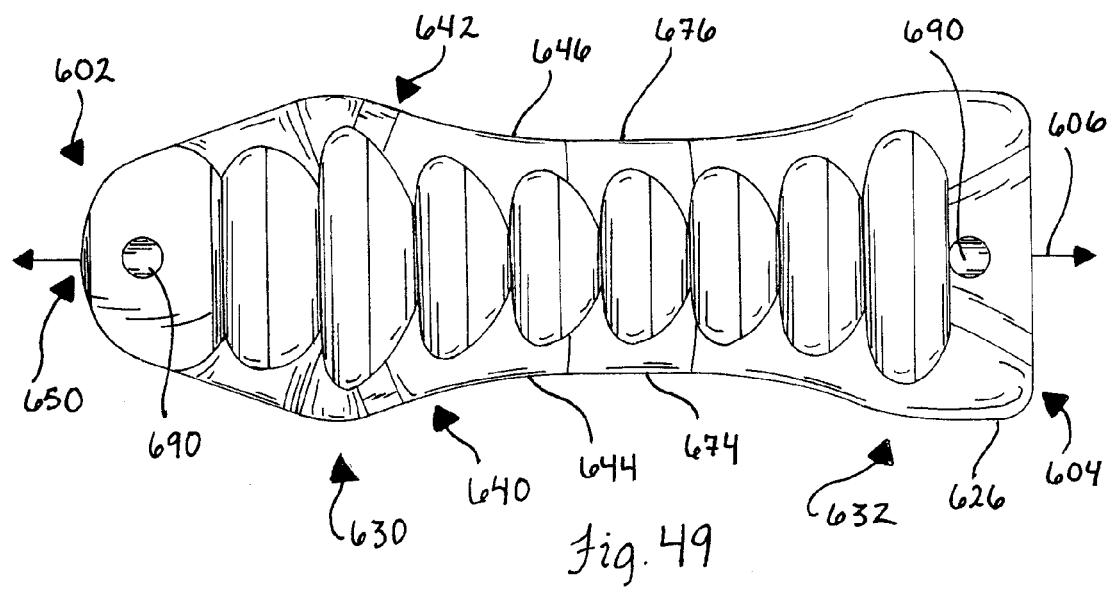
FIG. 49 is a plan view of the VBR device of FIG. 44 having an alternative configuration for the lateral side surfaces and gripping members.

With reference to FIGS. 44 and 45, the body 626 has an enlarged portion 630 proximate the insertion end portion 602 and an enlarged portion 632 proximate the trailing end portion 604. When implanted, the enlarged portion 630 is positioned towards the anterior portion of the intervertebral space. Lateral side surfaces 640, 642 extend between the upper and lower gripping surfaces 610, 612. The lateral side surfaces 640, 642 include concave portions 644, 646 between the enlarged portions 630 and 632 of the VBR 600. As best seen in FIGS. 45 and 49, the concave portions 644, 646 may form a smooth, continuously curved surface 670, 672, or may alternatively include flat portions 674, 676 at the inner most portion of the concave portions 640, 642.

When a pair of VBRs 600 is implanted, the respective bodies 626, and particularly the concave portions 644, 646, define a space therebetween for receipt of bone graft material. The enlarged portions 630 and 632 and the lateral side surfaces 640, 642 provide constraint for packing of graft material between the VBRs 600 and for resisting migration or explantation of the graft material.

Figure 46:
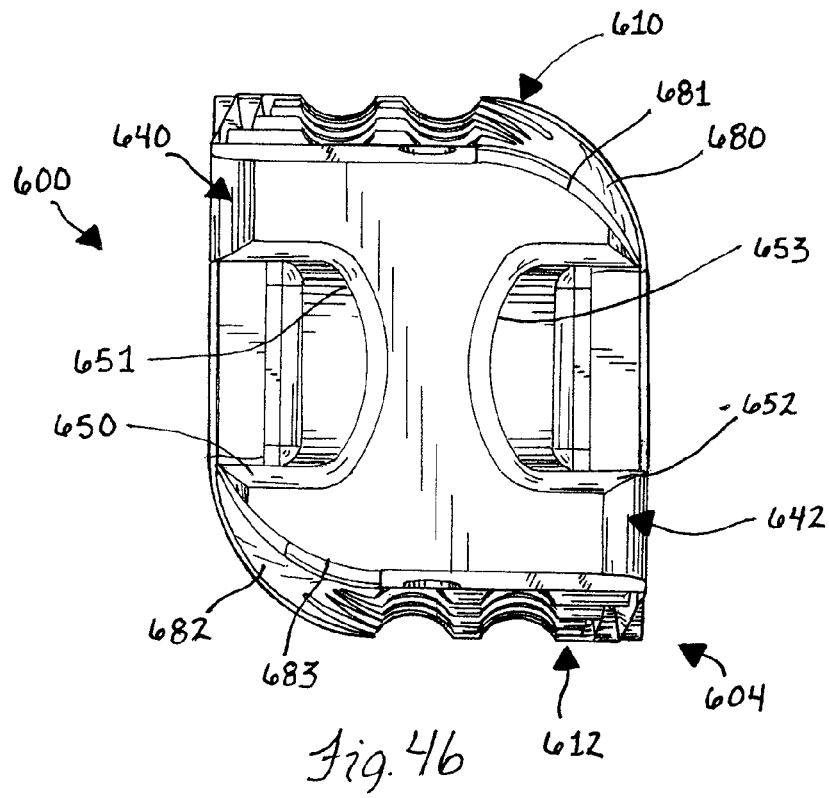
FIG. 46 is an end elevation view of the trailing end of the VBR device of FIG. 44 showing the slots being aligned with each other across the implant body.

With reference to FIGS. 44 and 46, the lateral side surface 642 meets the upper gripping surface 610 at elongate curved corner portion 680. Likewise, the lateral side surface 640 meets the lower gripping surface 612 at elongate curved corner portion 682. Elongate curved corner portions 680, 682 preferably extend along the length of the body 626 and include curved corner portions 681, 683 at the trailing end portion 604. The configuration of diagonally-opposed elongate curved corner portions 680, 682 allows the VBR 600 to be easily rotated from the insertion orientation to the implantation orientation (FIG. 46) by mitigating the stress upon VBR 600 and reducing the amount of force required to rotate the VBR. For example, the VBR may be rotated clockwise 90° from its insertion orientation to its implanted orientation. In the insertion orientation, the VBR 600 is oriented so that the lateral side surfaces 640, 642 are facing the adjacent vertebral surfaces and slide thereagainst. More specifically, in the insertion orientation the lateral side surface 642 is adjacent the superior vertebral surface, the lateral side surface 640 is adjacent the inferior vertebral surface, the elongate curved corner portion 680 is at the top left corner of the VBR 600, and the elongate curved corner portion 682 is at the bottom right corner of the VBR 600. As the VBR 600 is rotated clockwise 90° to its implantation orientation, the elongate curved corner portion 680 may roll laterally inwardly against the superior vertebral surface, and the elongate curved corner portion 682 may roll laterally inwardly against the inferior vertebral surface and thereby assist in the rotation of the VBR 600 by reducing the amount of force required from the surgeon and the amount of stress applied to the surfaces of the VBR 600. The elongate curved corner portions 680, 682 also avoid cutting unnecessary grooves in or damaging the vertebral surfaces as the VBR 600 is rotated.

Figure 70:
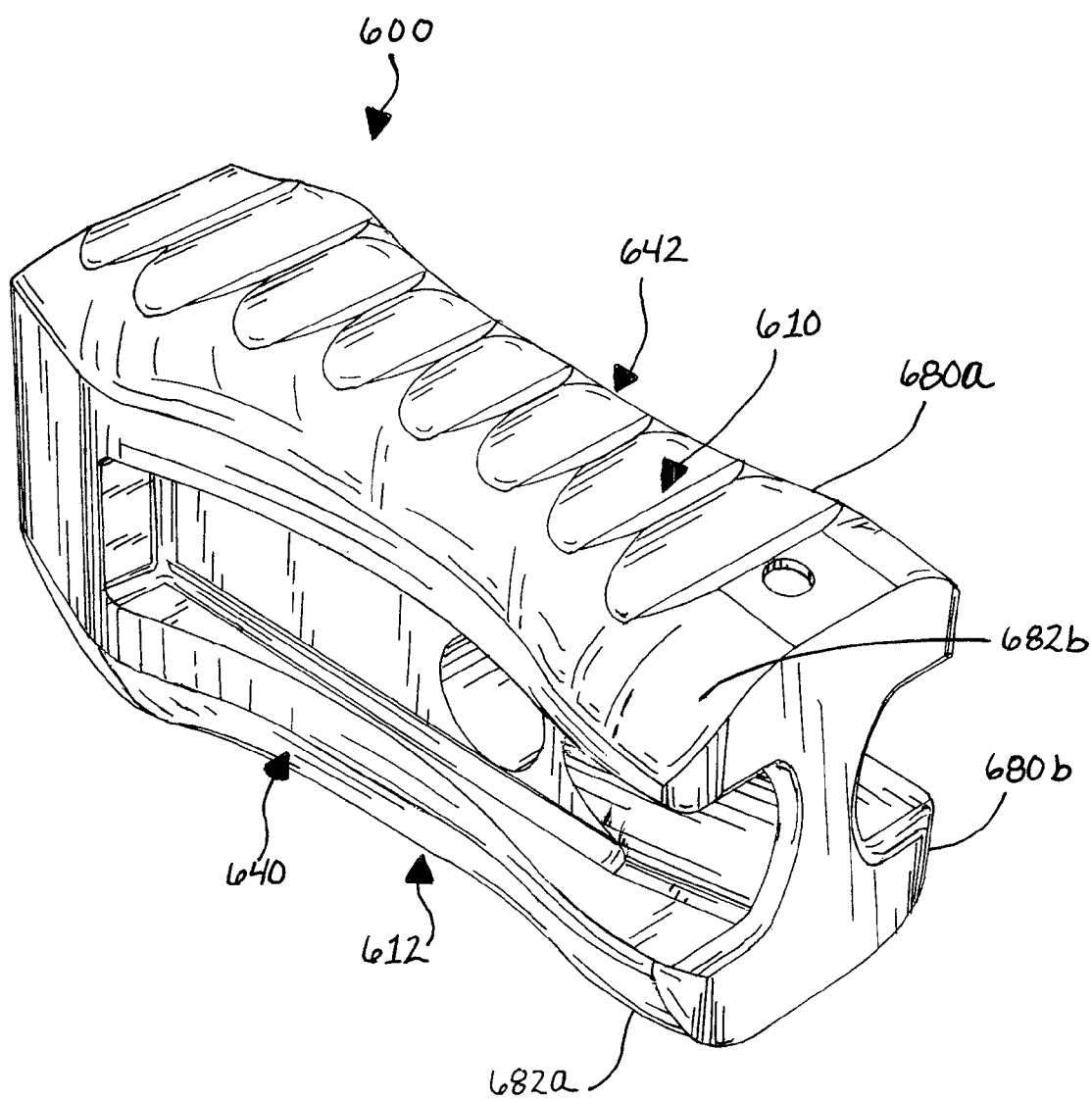
FIG. 70 is a perspective view of an alternative configuration of the VBR device of FIG. 44 having an implant body including four elongate curved corner portions and an alternative configuration for the gripping members.
Figure 71:
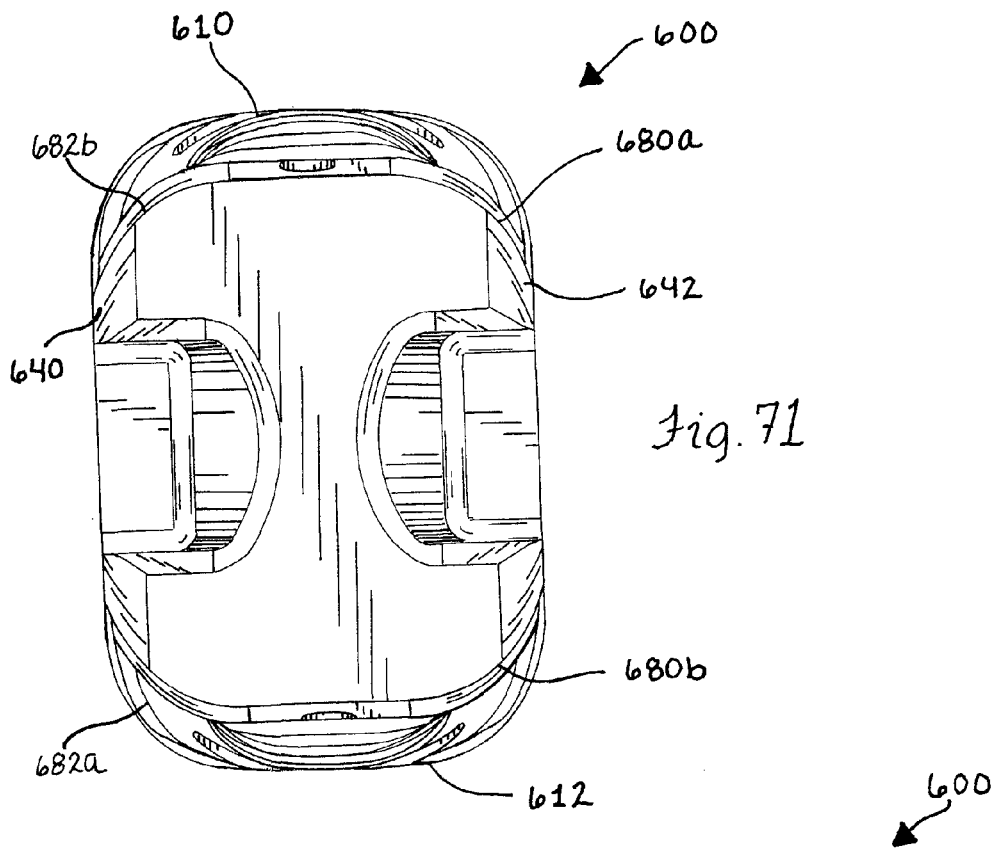
FIG. 71 is an end elevation view of the trailing end of the VBR device of FIG. 70.
Figure 72:
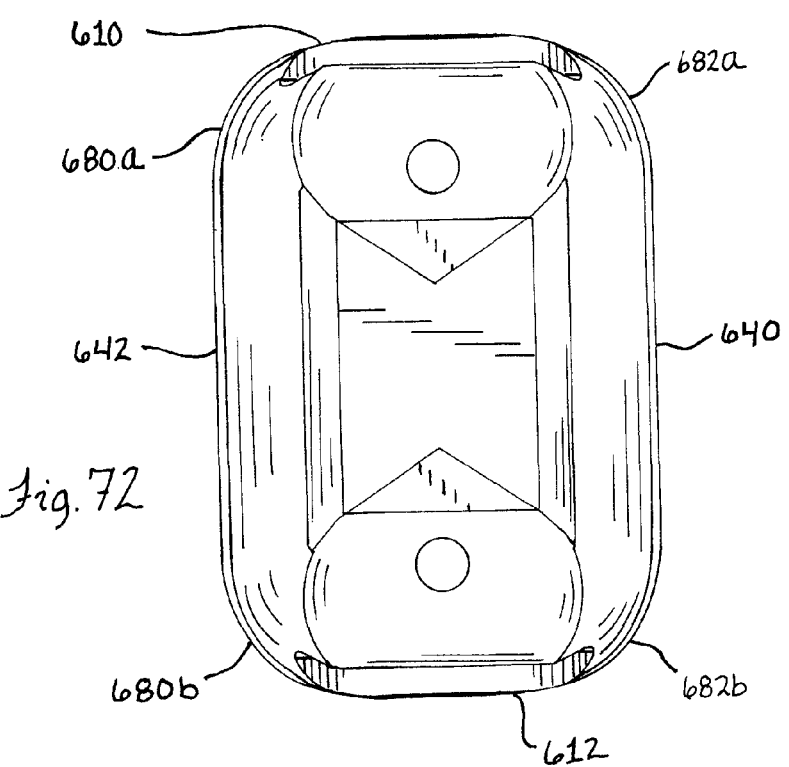
FIG. 72 is an end elevation view of the insertion end of the VBR device of FIG. 70.
Figure 73:
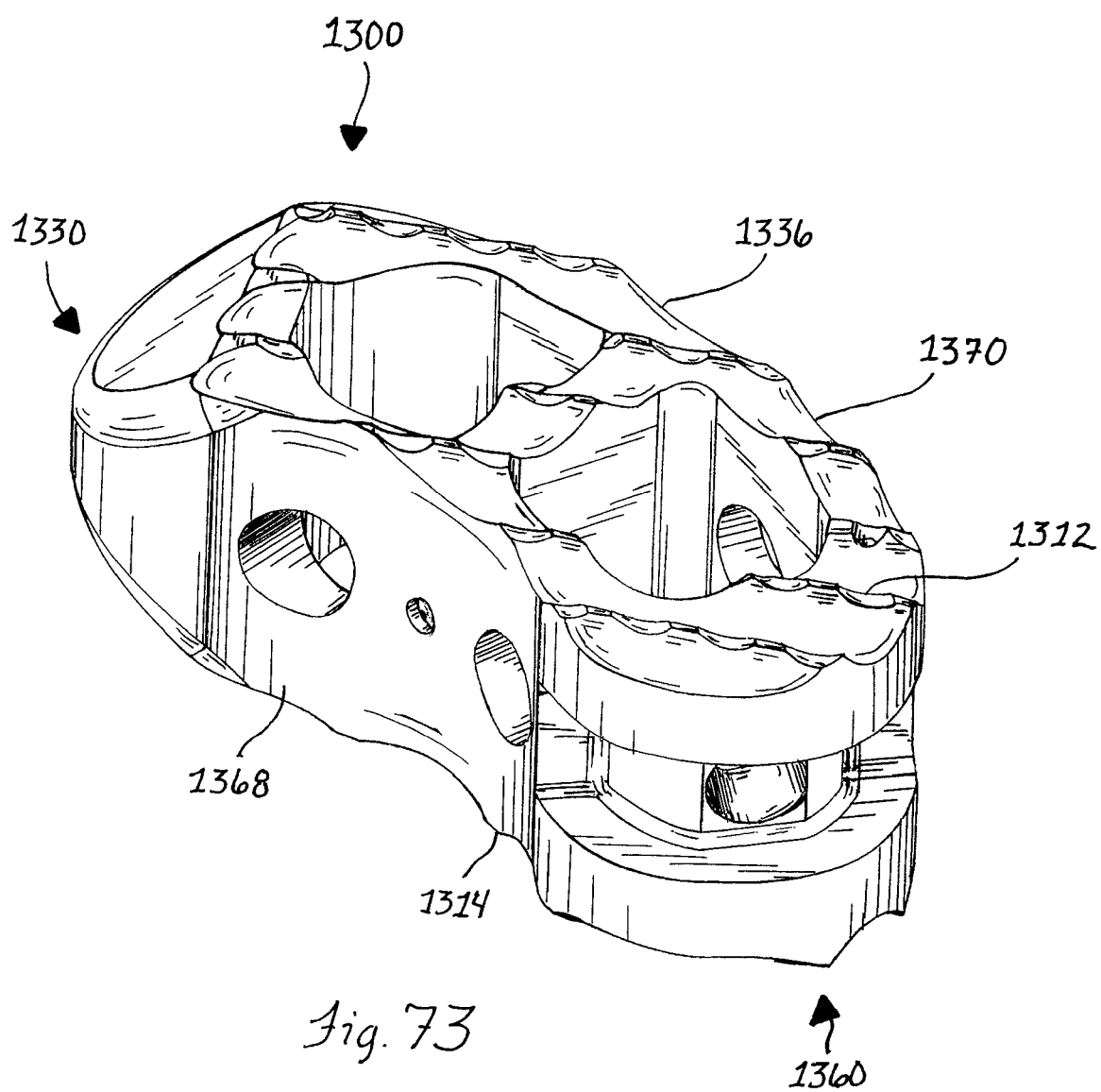
FIG. 73 is a perspective view of another alternative configuration of the VBR device of FIG. 1 having upper and lower surfaces that are angled with respect to one another.
Figure 74:
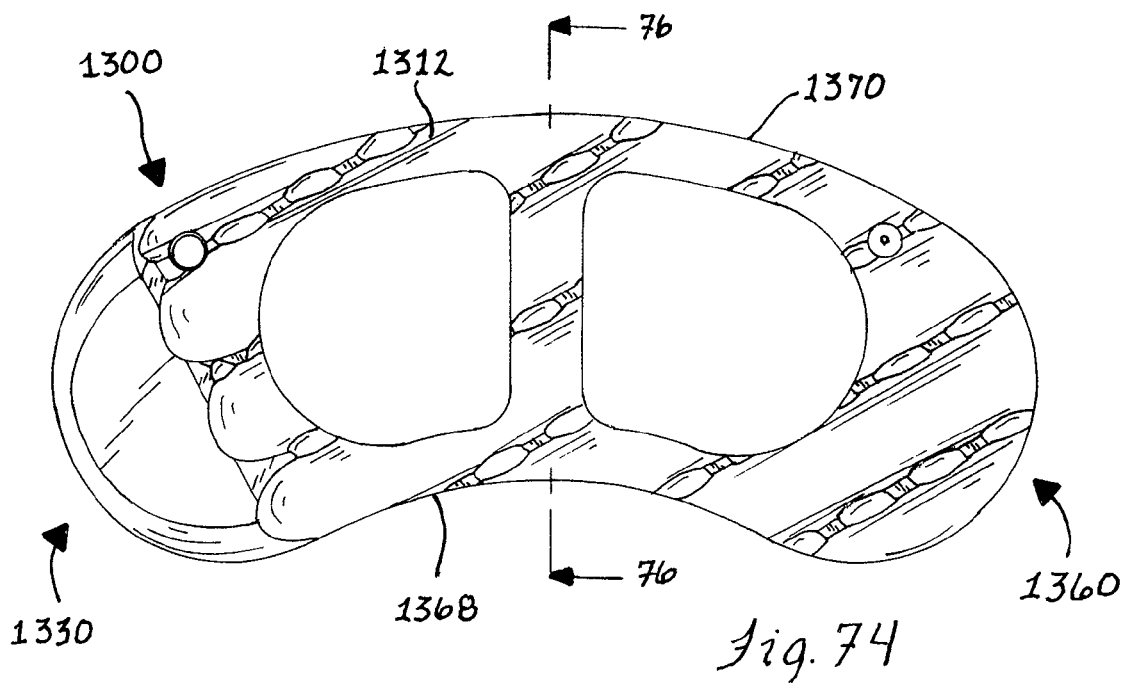
FIG. 74 is a top plan view of the VBR device of FIG. 73.

In another form, illustrated in FIGS. 70-72, the VBR 600 includes four such elongate curved corner portions. More specifically, the lateral side surface 642 meets the upper gripping surface 610 at elongate curved corner portion 680a and the lower gripping surface 612 at elongate curved corner portion 680b. Likewise, the lateral side surface 640 meets the lower gripping surface 612 at elongate curved corner portion 682a and the upper gripping surface 610 at elongate curved corner portion 682b.

In one form, the lateral side surfaces 640, 642 include slots 650, 652 opening laterally outward thereon. The slots 650, 652 are generally aligned with one another across the implant body and with the center of the VBR 600. The slots 650, 652 extend generally parallel to the longitudinal axis 602 of the VBR 600 along at least a portion of the lateral side surfaces 640, 642 and to the trailing end portion 604 of the VBR 600. The slots 650, 652 are cooperable with an inserter device, such as, for example, the insertion tool 1000 shown in FIGS. 63 and 64, which includes a pair of arms 1036, 1038 for being received in the slots 650, 652.

The slots 650, 652 may include concave recesses 651, 653 proximate the trailing end portion 604 of the VBR 600. The concave recesses 651, 653 are also cooperable with the insertion tool 1000. The configuration of the concave recesses 651, 653 assist the rotation of the VBR 600 from the insertion orientation to the implantation orientation. The shape of the concave recesses 651, 653 allows the pair of arms 1036, 1038 engaged therewith to distribute forces over a greater area and more evenly. As a result of the diagonally-opposed, curved portions 680, 682 and the specifically configured slots 650, 652, a wider selection of materials may be used for the VBR 600 than with other implant devices.

Referring now to FIGS. 51-54, an alternative configuration of the VBR 600 is shown. The VBR 700 includes the features described herein with respect to the VBR 600, but includes an alternative configuration for the slots 650, 652. Like the VBR 600, the VBR 700 includes a body 726 including an insertion end portion 702 and a trailing end portion 704 oriented along a longitudinal axis 706, upper and lower gripping surfaces 710, 712, and lateral side surfaces 740, 742 extending therebetween. Also like the VBR 600, the VBR 700 includes slots 750, 752 opening laterally outward onto the lateral side surfaces 740, 742 and extending generally parallel to the longitudinal axis 706 to the trailing end portion 704 of the VBR 700. However, as best seen in FIGS. 51 and 52, rather than being aligned with one another across the implant body, the slots 750, 752 are offset from one another. For example, the slot 750 may be positioned slightly above the center of the VBR 700, while the slot 752 may be positioned slightly below the center of the VBR 700. This positioning of the slots 750, 752 assists in rotation of the VBR 700 from the insertion orientation to the implantation orientation. As the VBR 700 is rotated about its longitudinal axis 706, offsetting the slots 750, 752 from the center of the VBR 700 increases their distance from the axis of rotation. This increased distance in effect provides a larger lever arm so that the amount of force necessary to rotate the VBR 700 with the insertion tool is reduces.

As shown in FIGS. 51 and 52, the VBR 700 also includes diagonally-opposed, curved portions 780, 782 that preferably extend along the length of the body 726 and include curved corner portions 781, 783. Additionally, diagonally-opposed corner flanges 785, 787 are disposed between the slots 750, 752 and the upper and lower gripping surfaces 710, 712. As a result of the offset positioning of the slots 750, 752, the corner flanges 785, 787 are substantially narrower than the curved corner portions 781, 783. When the curved corner portions 781, 783 roll laterally inwardly against the superior and inferior vertebral surfaces, the corner flanges 785, 787 move laterally outwardly away from the superior and inferior vertebral surfaces and, therefore, do not contact the vertebral surfaces during rotation of the body 726. Moreover, the body 726 has an increased cross-sectional area relative to an implant body having aligned slots. As a result of the diagonally-opposed, curved portions 780, 782 and the offset slots 750, 752, a wider selection of materials may be used for the VBR 700 than with other implant devices. Like the VBR 600, the VBR 700 may alternatively include four of such curved portions.

Again, implantation of either the VBR 600 or the VBR 700 may be preceded by use of one or more trial spacer devices (not shown) with a size and shape corresponding to various sizes of the VBRs 600 and 700. Additionally, tamp devices may be used for packing bone graft material or adjusting the position of the VBR 600 or the VBR 700.

Figure 55:
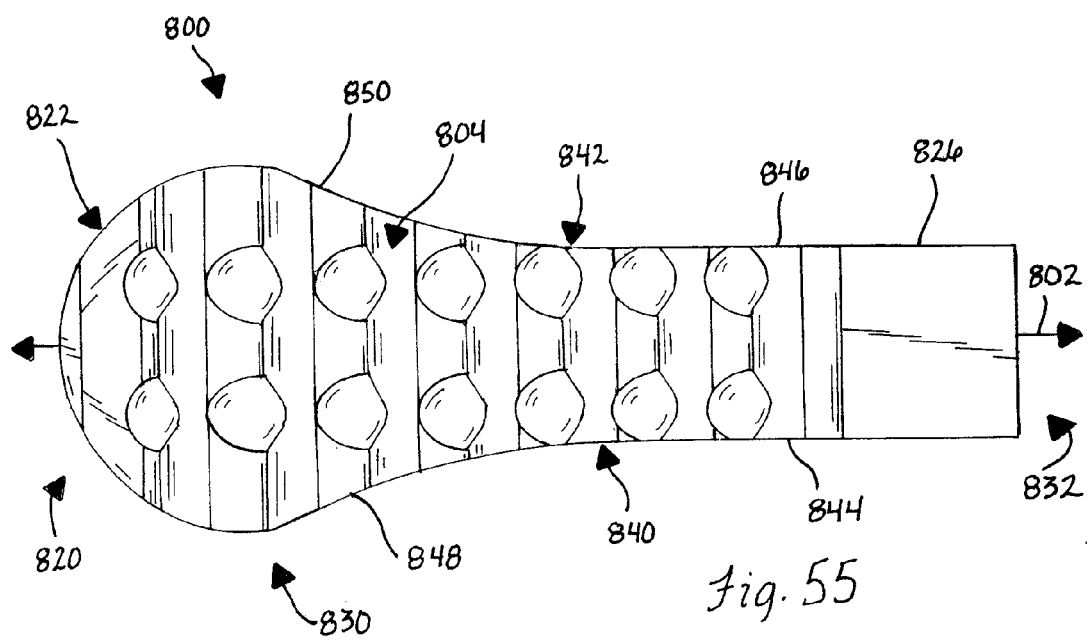
FIG. 55 is a plan view of a further form of a VBR device having an enlarged and rounded insertion end and a narrow trailing end.
Figure 56:
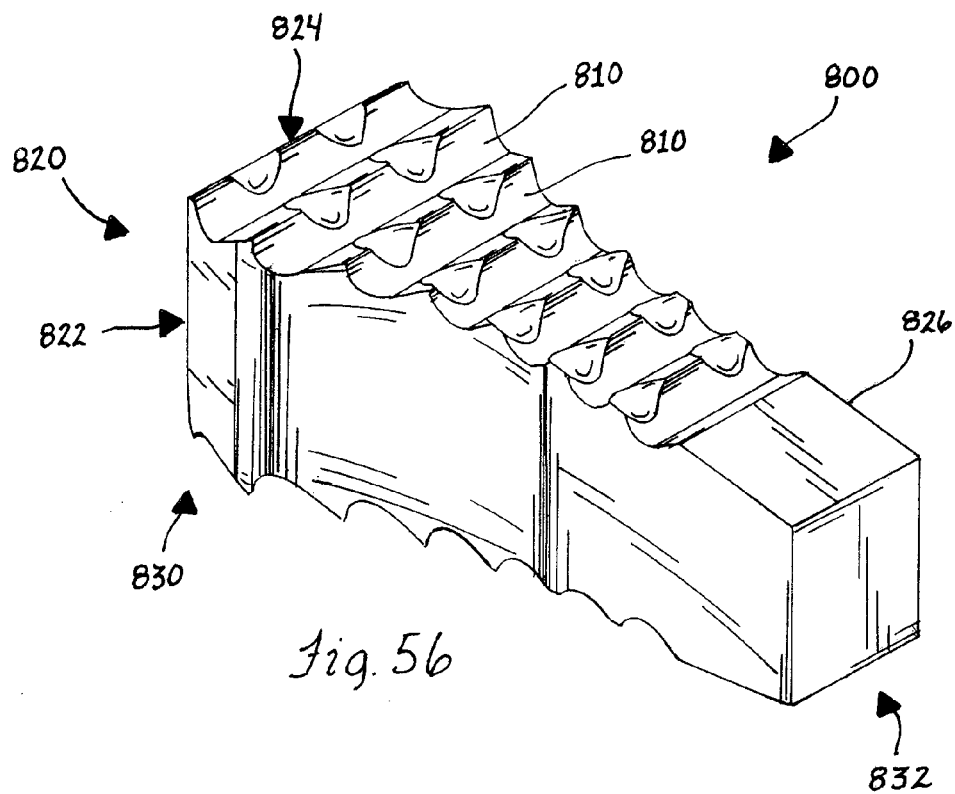
FIG. 56 is a perspective view of the VBR device of FIG. 55.
Figure 57:
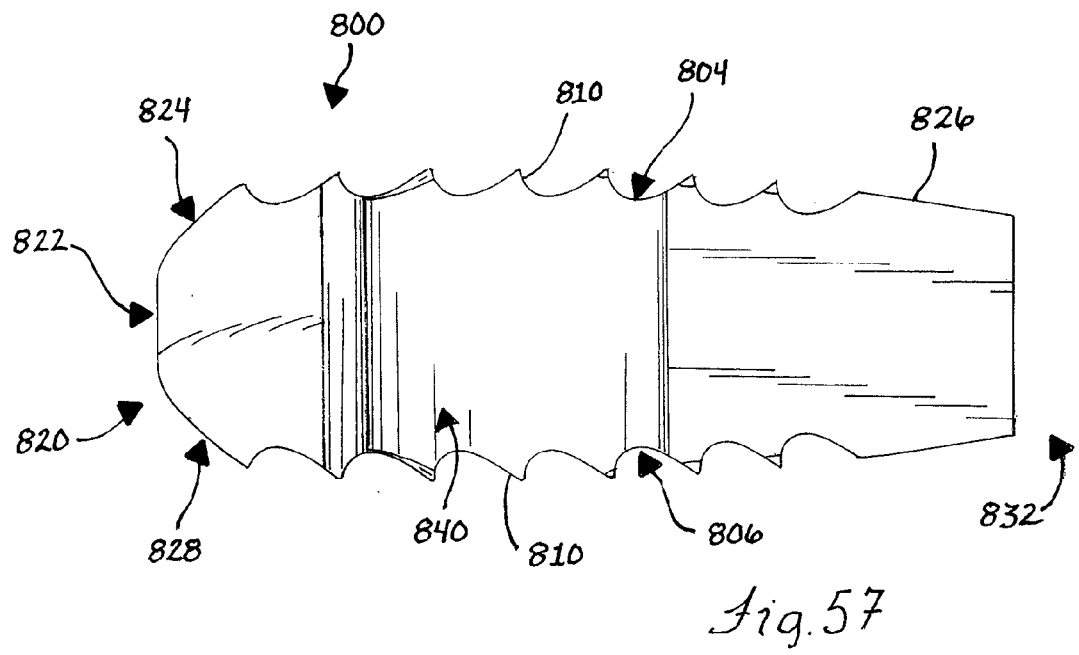
FIG. 57 is a side elevation view of the VBR device of FIG. 55 showing arcuate upper and lower surfaces with gripping members thereon, and showing the insertion end having upper and lower slanted surfaces.

Another form of implant device in the form of a vertebral replacement body (VBR) 800 for spinal fusion surgery is illustrated in FIGS. 55-57. In a preferred form, a pair of VBRs 800 is implanted in the intervertebral space. The VBR 800 has a longitudinal axis 802 that, when implanted, is generally oriented in the anterior-posterior direction, or at a slight angle thereto.

Again, the VBR 800 includes a number of features described above in relation to the other VBRs. The VBR 800 has upper and lower gripping surfaces 804, 806 including rows of uni-directional teeth 810 substantially embodying the features of the uni-directional teeth described above. An insertion end 820 has a tapered shape formed by a rounded vertical surface 822, a slanted surface 824 angled downward from the upper gripping surface 804 and intersecting with the rounded vertical surface 822, and a slanted surface 828 angled upward from the lower gripping surface 806 and also intersecting with the rounded vertical surface 822. The upper and lower gripping surfaces 804, 806 have an arcuate profile to mate with the concavity of the vertebral surfaces to minimize bone subsidence and maximize purchase by the teeth 810 within the vertebral surfaces. The VBR 800 is generally solid and free of throughbores or cavities for receiving graft material or allowing bone growth through the VBR 800.

With reference to FIG. 55, the VBR 800 is generally symmetrical in a direction transverse and lateral to the longitudinal axis 802. As such, each VBR 800 may be implanted on either lateral side of the intervertebral space. This is in contrast to the VBRs 400 and 500 which are not symmetrical and require a mirror-imaged VBR to be implanted in the intervertebral space so that the inner sides 520 and the vertical cut-outs 542 of each face each other.

The VBR 800 has a body 826 with an enlarged portion 830 proximate the insertion end 820. When implanted, the enlarged portion 830 is towards the anterior portion of the intervertebral space. The VBR 800 has a trailing end 832 opposite the insertion end 820. Other than the enlarged portion 830, the body 826 generally has a constant lateral width.

The enlarged portion 830 is generally defined by the rounded vertical surface 822 of the insertion end 820 and the upper and lower gripping surfaces 804, 806. More specifically, the rounded vertical surface 822 wraps around the insertion end 820, extends rearwardly towards the trailing end 832, and then curves inwardly towards the longitudinal axis 802. The VBR 800 includes lateral side surfaces 840, 842 extending between the upper and lower gripping surfaces 804, 806. The lateral side surfaces 840, 842 include generally planar portions 844, 846 extending from the trailing end 832. Proximate the enlarged portion 830, the lateral side surfaces 840, 842 include outwardly curving portions 848, 850, which merge with the inwardly curving portion of the vertical surface 822 such that the VBR body flares laterally outward from the longitudinal axis 802. The lateral side surfaces 840, 842 may include slots (not shown) similar to the slots 650, 652 described above with respect to the VBR 600 or the channels 750, 752 described above with respect to the VBR 700 for coupling with an inserter device (such as, for example, the insertion tool 1000 shown in FIGS. 63 and 64).

The VBR 800 is implanted in a lateral or posterior-lateral direction. When a pair of VBRs 800 is implanted, the respective bodies 826 define a space or volume therebetween for receipt of bone graft material. For a pair, the enlarged portions 830 positioned towards the anterior portion of the intervertebral space provide a retention region for the graft material in a manner similar to the vertical cut-outs 542 of the VBR 500. The enlarged portions 830 and the lateral side surfaces 840, 842 provide constraint for packing of graft material between the VBRs 800 and for resisting migration or explantation of the graft material. The relatively narrow trailing ends 832 of the pair of VBRs 800 also allow easy access for packing material therebetween.

Again, implantation of either the VBR 800 may be preceded by use of one or more trial spacer devices (not shown) with a size and shape corresponding to various sizes of the VBR 800, and tamp devices may be used for packing bone graft material or adjusting the position of the VBR 800.

The VBRs 400, 500, 600, 700, 800, 900, and 1300 described herein may be formed of any suitable biocompatible material, though a polymer such as PEEK, a ceramic such as hydroxyapatite or tricalcium phosphate, or a combination thereof is particularly preferred.

With reference now to FIGS. 63 and 64, the insertion tool 1000 is shown. As noted above, the insertion tool 1000 may be used to insert any of the VBRs 400, 500, 600, 700, or 800. Insertion tool 1000 has a handle portion 1002 allowing the surgeon to grip the insertion tool and manipulate the coupled VBR into the desired position and orientation within the intervertebral space. Extending from the handle portion 1002 is a shaft portion 1004 including an outer shaft portion 1006 and an inner shaft portion 1008.

The outer shaft portion 1006 includes a longitudinal throughbore 1010 in which the inner shaft 1008 is slidably received. The proximal end 1012 of the outer shaft portion 1006 includes a first camming surface 1014. The distal end 1016 of the outer shaft portion 1006 includes a distal surface 1018. Disposed between the outer shaft portion 1006 and the handle portion 1002 is a housing 1020 and a cam trigger 1022 coupled to the housing by a rivet 1024. The cam trigger 1022 includes a second camming surface 1026 in communication with the first camming surface 1014 of the outer shaft portion 1006 and a lever portion 1028 operable to cause the second camming surface 1026 to cam against the first camming surface 1014 and move the outer shaft portion 1006 translationally downward along its longitudinal axis.

The inner shaft portion 1008 extends through the longitudinal throughbore 1010 of outer shaft portion 1006. An engagement portion 1030 at the distal end of the inner shaft portion 1008 extends past the distal surface 1018 of the outer shaft portion 1006. The engagement portion 1030 includes a pair of abutment surfaces 1032 and 1034 facing the distal surface 1018 of the outer shaft portion 1006. Arms 1036 and 1038 extend distally from the pair of abutment surfaces 1032, 1034. Arms 1036 and 1038 are sized to be received in channels formed in the VBR, for example, the slots 650, 652 formed in the lateral side surfaces 640, 642 of the VBR 600. Arms 1036 and 1038 are separated by a channel 1040 sized to receive the VBR therein. A slot 1042 in the inner shaft 1008 is in communication with the channel 1040.

When the lever portion 1028 of the cam trigger 1022 is depressed, the second camming surface 1026 cams against the first camming surface 1014 of the outer shaft portion 1006, causing the outer shaft portion 1006 to move along its longitudinal axis toward the engagement portion 1030 of the inner shaft 1008. As a result, the distal surface 1018 of the outer shaft portion 1006 engages the abutment surfaces 1032, 1034 of the engagement portion 1030, thereby pinching arms 1036, 1038 together to securely engage the coupled VBR. The surgeon can then insert and manipulate the coupled VBR into the desired position and orientation within the intervertebral space.

Figure 65:
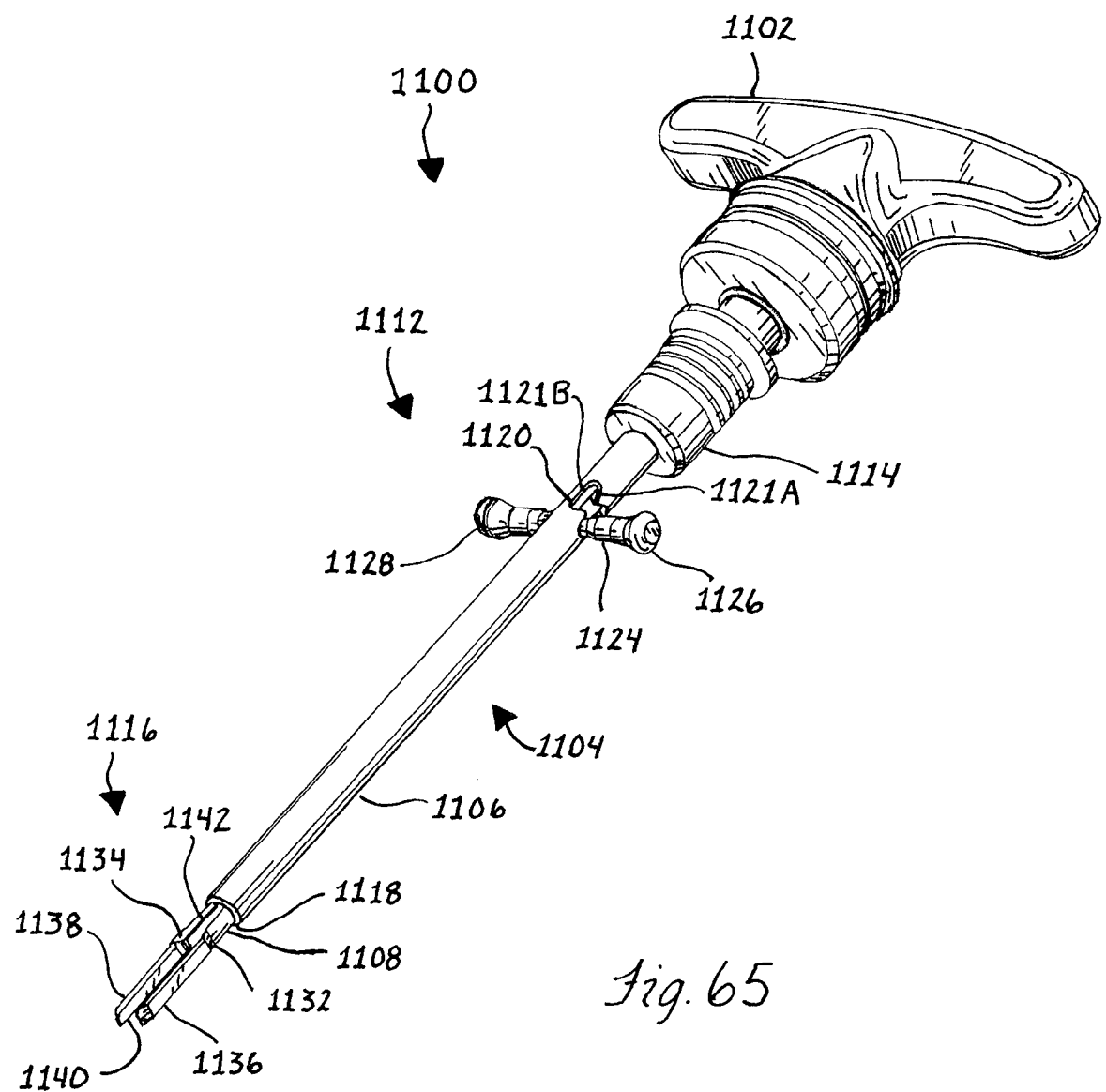
FIGS. 65 and 66 are perspective views of an alternative insertion tool for implanting any of the VBR devices shown in FIGS. 29, 36, 44, 51, 55, and 68.
Figure 66:
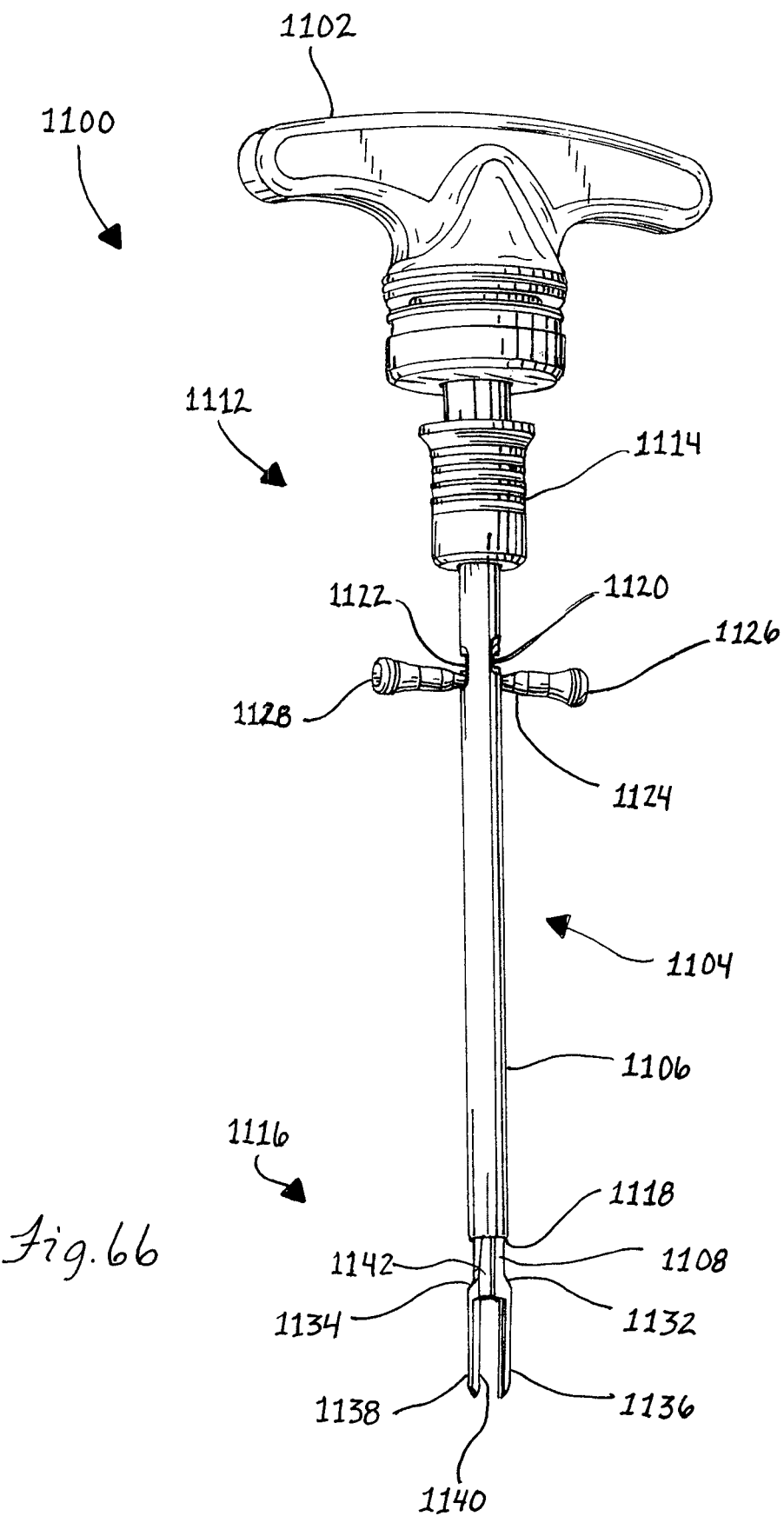
Figure 67:
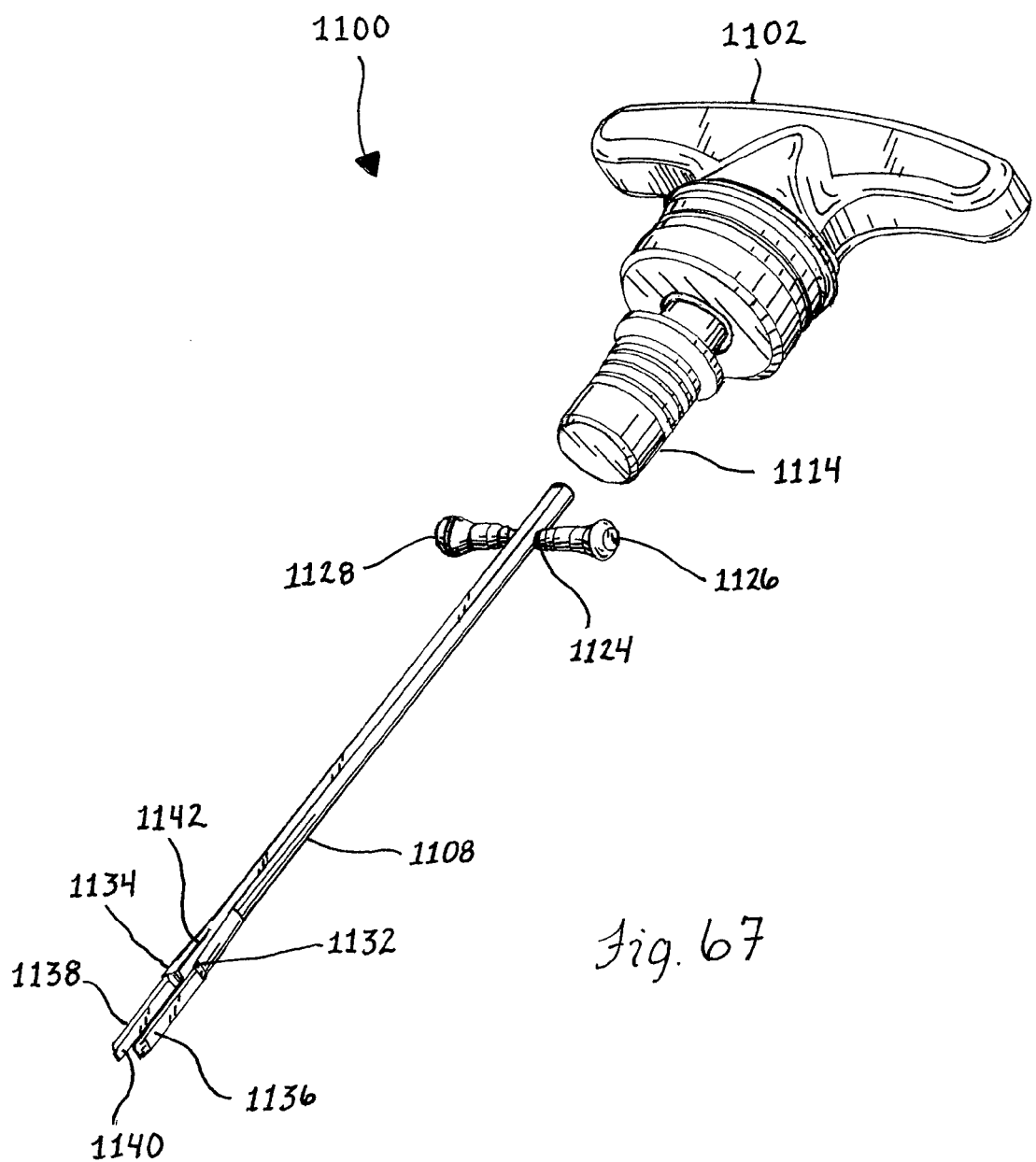
FIG. 67 is a perspective view of the insertion tool of FIGS. 65 and 66 shown with the outer shaft removed.

With reference now to FIGS. 65-67, an insertion tool 1100 is shown. As with the insertion tool 1000, the insertion tool 1100 may be used to insert any of the VBRs 400, 500, 600, 700, or 800. Insertion tool 1100 has a handle portion 1102 allowing the surgeon to grip the insertion tool and manipulate the coupled VBR into the desired position and orientation within the intervertebral space. Extending from the handle portion 1102 is a shaft portion 1104 including an outer shaft portion 1106 and an inner shaft portion 1108.

The outer shaft portion 1106 includes a longitudinal throughbore 1110 in which the inner shaft 1108 is slidably received. The proximal end 1112 of the outer shaft portion 1106 is coupled to the handle portion 1102 by a collar 1114. The distal end 1116 of the outer shaft portion 1106 includes a distal surface 1118.

First and second apertures 1120 and 1122 are disposed in the outer shaft portion 1106 radially opposed to one another. The apertures 1120, 1122 each include a distal portion 1121A, 1123A and a proximal portion 1121B, 1123B. Each of the proximal portions 1121B, 1123B is radially offset from the respective distal portion 1121A, 1123A.

The inner shaft portion 1108 extends through the longitudinal throughbore 1110 of outer shaft portion 1106 and is moveable both rotationally and translationally within the outer shaft portion 1106. An engagement portion 1130 at the distal end of the inner shaft portion 1108 is similar to the engagement portion 1030 described above with respect to the insertion tool 1000. The engagement portion 1130 extends past the distal surface 1118 of the outer shaft portion 1106 and includes a pair of abutment surfaces 1132 and 1134 facing the distal surface 1118 of the outer shaft portion 1106. Arms 1136 and 1138 extend distally from the pair of abutment surfaces 1132, 1134. Arms 1136 and 1138 are sized to be received in channels formed in the VBR, for example, the slots 650, 652 formed in the lateral side surfaces 640, 642 of the VBR 600. Arms 1136 and 1138 are separated by a channel 1140 sized to receive the VBR therein. A slot 1142 in the inner shaft 1108 is in communication with the channel 1140.

A handle 1124 including pins 1126 and 1128 is coupled to the inner shaft portion 1108. Pins 1126 and 1128 are received in apertures 1120 and 1122 to secure the inner shaft portion 1108 relative to the outer shaft portion 1106. For example, pin 1126 may be initially received in distal portion 1121A of aperture 1120, while pin 1128 may be initially received in distal portion 1123A of aperture 1122. In such a position, the engagement portion 1130 of the inner shaft portion 1106 extends past the distal surface 1118 of the outer shaft portion 1106 and the abutment surfaces 1132 and 1134 of the inner shaft portion 1108 do not engage the distal surface 1118 of the outer shaft portion 1106.

When an upward force is applied to the handle 1124, the inner shaft 1108 moves translationally within the outer shaft 1108 such that the abutment surfaces 1132 and 1134 come into engagement with the distal surface 1118, thereby pinching arms 1136, 1138 together to securely engage the coupled VBR. A rotational force may then be applied to the handle to move pin 1126 from the distal portion 1121A to the proximal portion 1121B of aperture 1120 to pin 1128 from the distal portion 1123A to the proximal portion 1123B of aperture 1122. The inner shaft portion 1108 is thereby secured in position relative to the outer shaft portion 1106 and securely engaging the coupled VBR. The surgeon can then insert and manipulate the coupled VBR into the desired position and orientation within the intervertebral space.

Figure 68B:
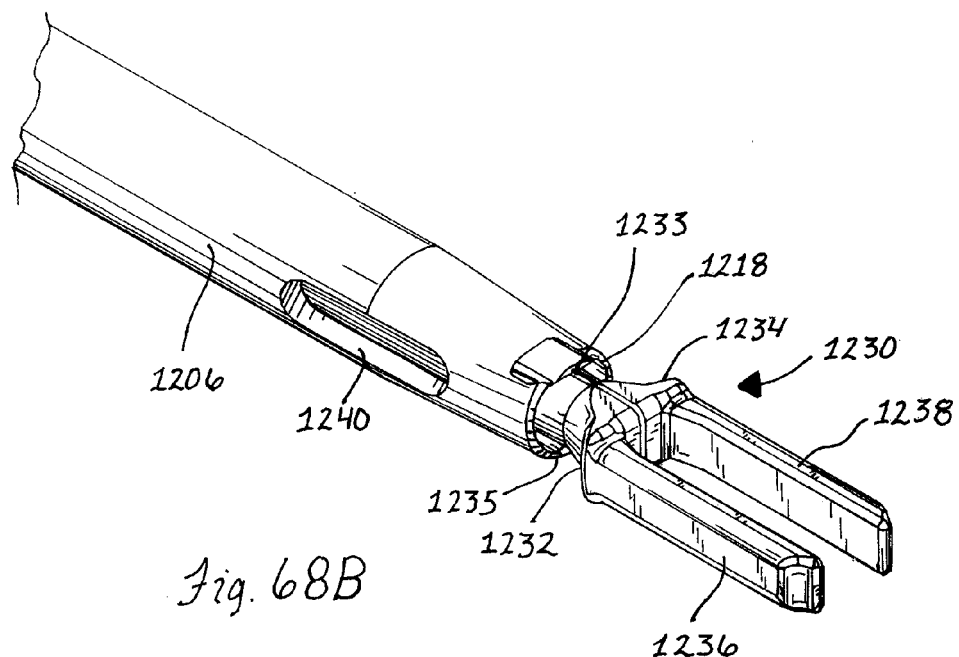
FIG. 68B is an enlarged perspective view of the insertion tool of FIG. 68A.
Figure 68A:
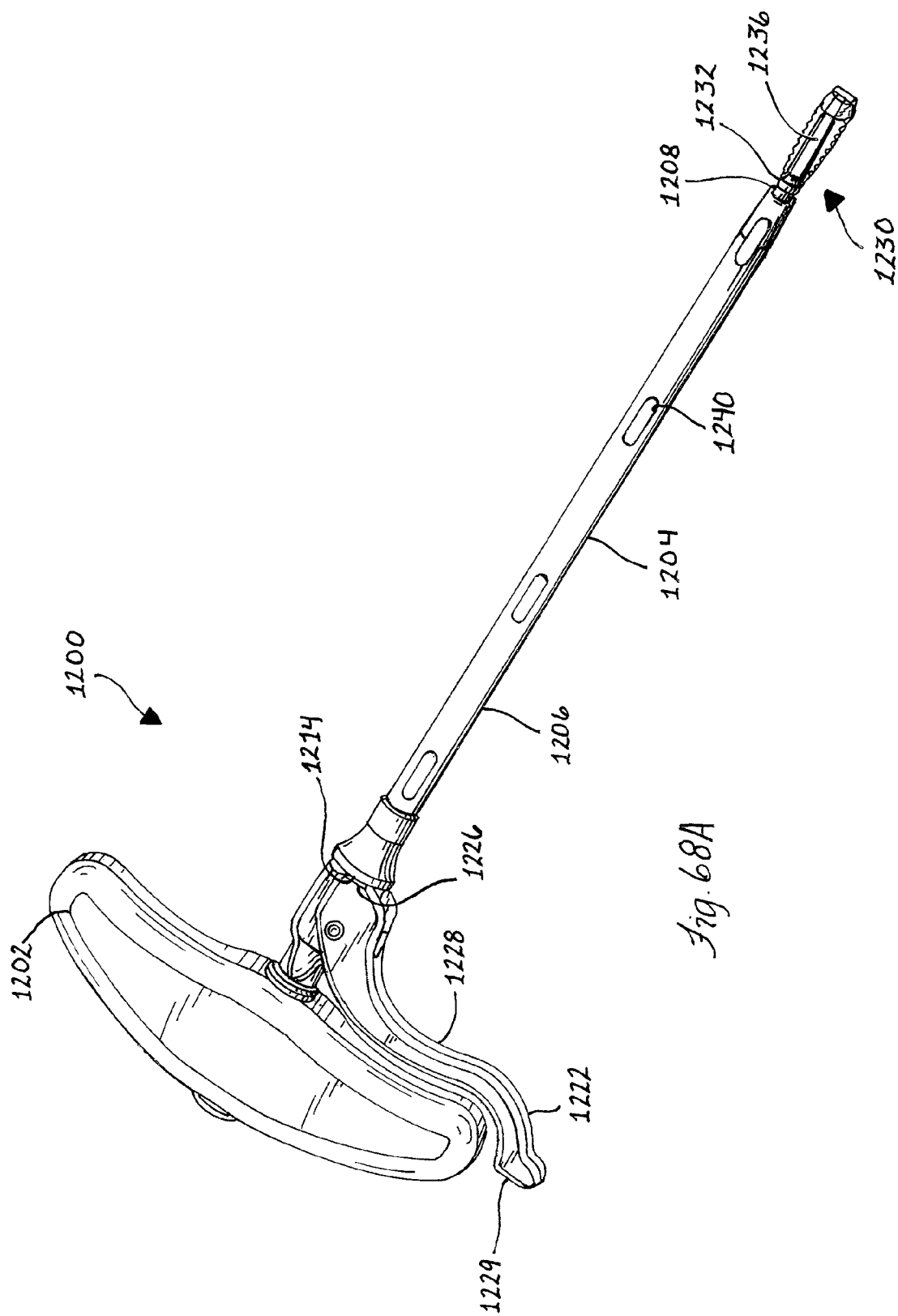
FIG. 68A is a perspective view of an alternative configuration of the insertion tool of FIG. 63.
Figure 69:
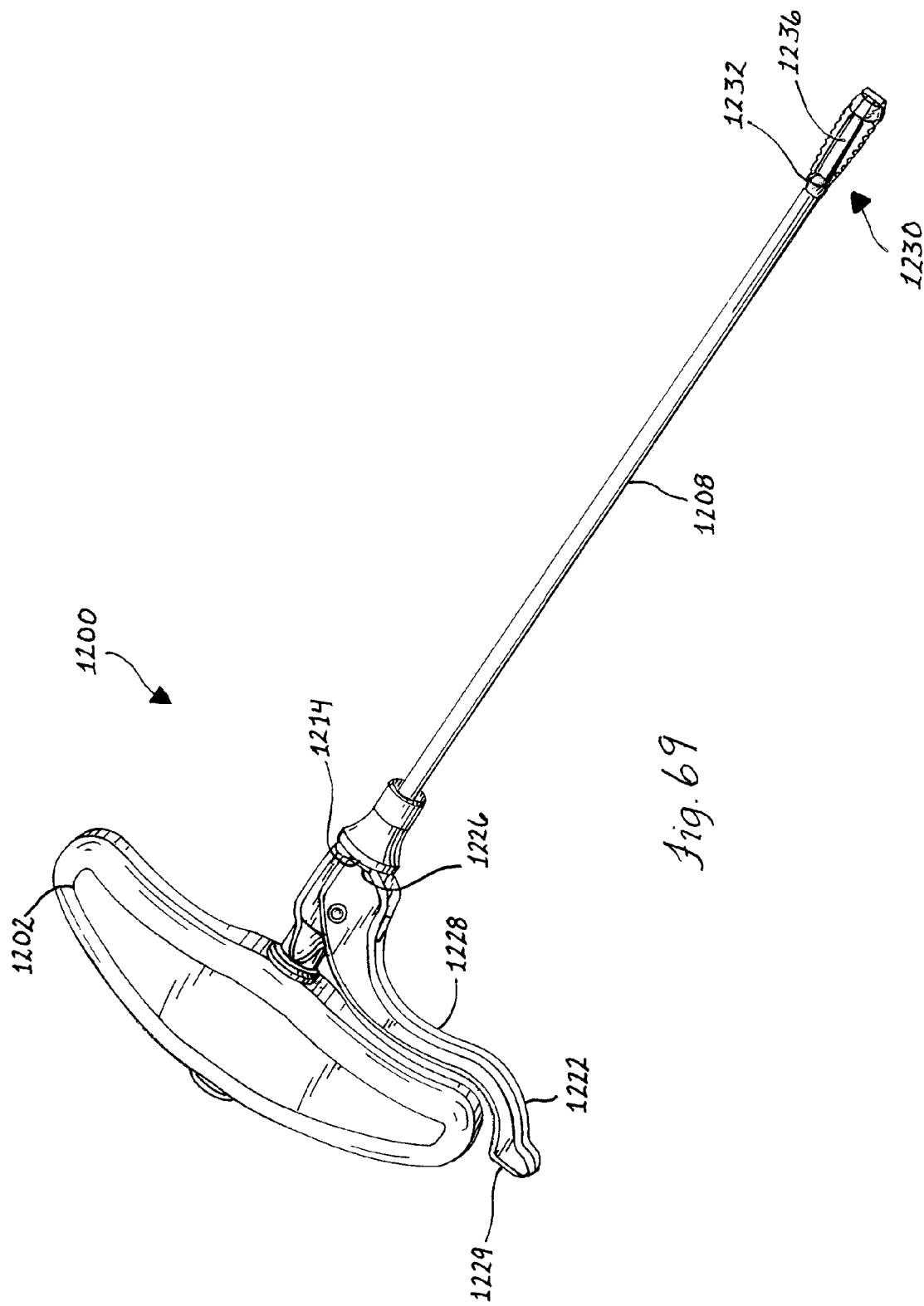
FIG. 69 is a perspective view of the insertion tool of FIG. 68A shown with the outer shaft removed.

With reference now to FIGS. 68 and 69, an insertion tool 1200 is shown. Insertion tool 1200 includes the features described above with respect to insertion tool 1000, including a handle portion 1202 and a shaft portion 1204 including an outer shaft portion 1206 and an inner shaft portion 1208. A cam trigger 1222, in communication with the outer shaft portion 1206, causes the outer shaft portion 1206 to move translationally downward along its longitudinal axis thereby pinching together a pair of arms 1236, 1238 at the distal end of the inner shaft portion 1208 to securely engage a coupled VBR.

Like the cam trigger 1022, the cam trigger 1222 includes a second camming surface 1226 in communication with a first camming surface 1214 of the outer shaft portion 1206 and a lever portion 1228, which, when depressed, causes the second camming surface 1226 to cam against the first camming surface 1214 and move the outer shaft portion 1206 downward. The lever portion 1228 also includes a release portion 1229, which can be pushed in the opposite direction to release the lever portion 1228 thereby disengaging the second camming surface 1226 from the first camming surface 1214 and allowing the outer shaft to move upward translationally along its longitudinal axis and the arms 1236, 1238 to move apart and release the VBR.

As described above with respect to insertion tool 1000, an engagement portion 1230 at the distal end of the inner shaft portion 1208 extends past a distal surface 1218 of the outer shaft portion 1206. The engagement portion 1230 includes a pair of abutment surfaces 1232 and 1234 facing the distal surface 1218 of the outer shaft portion 1206. Arms 1236 and 1238 extend distally from the pair of abutment surfaces 1232, 1234. The distal surface 1218 of the outer shaft portion 1206 includes flats 1233, 1235 that engage the abutment surfaces 1232, 1234 when the cam trigger is depressed thereby providing additional force to pinch the arms 1236, 1238 together.

In the illustrated embodiment, the outer shaft portion 1206 additionally includes a plurality of openings 1240 that allow for ease of cleaning the insertion tool 1200.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

What is claimed is:

1. An implant device for implantation within an intervertebral space between adjacent vertebrae, the implant device comprising:

an implant body having an insertion end, a trailing end, and a longitudinal axis extending generally between the insertion end and the trailing end;

an upper surface and a lower surface of the body; and one or more first rows of gripping members formed on at least a portion of both the upper and lower surfaces for engaging the adjacent vertebrae, the one or more first rows of gripping members being spaced apart by a channel having a first width and a first depth, and the gripping members including peaks that are spaced apart by a depression having a second width and a second depth, the first width being greater than the second width and the first depth being greater than the second depth, with each row having a leading inclined surface, the first rows having a predetermined orientation relative to the longitudinal axis such that the leading inclined surfaces extend transverse thereto at an angle of less than 90° and thereby turn the implant body during insertion about an axis generally parallel to the superior-inferior axis of the spine from an insertion orientation with the longitudinal axis extending in a generally anterior-posterior direction toward an implantation orientation in the intervertebral space via the rows of gripping members engaging the adjacent vertebrae and the predetermined orientation of the rows thereof causing the implant body to be frictionally biased toward the implantation orientation from the insertion orientation, wherein the implant body has one or more second rows of gripping members, the one or more second rows each having a second inclined surface that extend generally transverse to the leading inclined surfaces of the one or more first rows so as to engage the adjacent vertebrae frictionally biasing the implant body to be turned about the axis generally parallel to the superior-inferior axis of the spine toward the implantation orientation in the intervertebral space.

2. The implant device of claim 1 wherein the body has at least one cavity opening to the upper and lower surfaces for receipt of graft material therein, and at least one of the first rows being a split row with gripping members on either side of the cavity and aligned with each other across the cavity.

3. The implant device of claim 2 wherein the one or more first rows include adjacent first rows with at least one of the adjacent first rows being the split row, the adjacent first rows spaced apart by a first distance and the adjacent gripping members of the split row on one side or the other of the cavity are spaced apart by a second distance less than the first distance.

4. The implant device of claim 1 wherein the one or more first rows include adjacent first rows spaced apart by a first distance, and the adjacent gripping members in the rows being generally spaced apart by a second distance less that the first distance.

5. The implant device of claim 1 wherein the gripping members are spaced teeth.

6. The implant device of claim 1 wherein the first rows are linear rows and the predetermined orientation of the linear rows such that the leading inclined surfaces have a predetermined angle of approximately 30° to the longitudinal axis.

7. The implant device of claim 1 wherein the implant body includes one or more cavities for receiving bone graft material therein.

8. The implant device of claim 1 wherein the second inclined surfaces of the one or more second rows have an arcuate configuration.

9. The implant device of claim 1 wherein the upper surface and lower surface define a variable height of the body and the upper surface and lower surface are angled with respect to one another such that the height increases in a direction generally perpendicular to the longitudinal axis.

* * * * *